US006607884B1

(12) United States Patent
Lee et al.

(10) Patent No.: US 6,607,884 B1
(45) Date of Patent: Aug. 19, 2003

(54) METHODS OF DETECTING GROWTH DIFFERENTIATION FACTOR-8

(75) Inventors: Se-Jin Lee, Baltimore, MD (US); Alexandra C. McPherron, Baltimore, MD (US)

(73) Assignee: The Johns Hopkins University School of Medicine, Baltimore, MD (US)

(*) Notice: Subject to any disclaimer, the term of this patent is extended or adjusted under 35 U.S.C. 154(b) by 0 days.

(21) Appl. No.: 09/686,344

(22) Filed: Oct. 10, 2000

Related U.S. Application Data

(63) Continuation of application No. 09/019,070, filed on Feb. 5, 1998, now abandoned, which is a continuation-in-part of application No. 08/862,445, filed on May 23, 1997, now abandoned, which is a continuation-in-part of application No. 08/847,910, filed on Apr. 28, 1997, now abandoned, which is a continuation-in-part of application No. 08/795, 071, filed on Feb. 5, 1997, now Pat. No. 5,994,618, which is a continuation-in-part of application No. 08/525,596, filed as application No. PCT/US94/03019 on Mar. 18, 1994, now Pat. No. 5,827,733, said application No. 09/019,070, is a continuation-in-part of application No. 08/033,923, filed on Mar. 19, 1993, now abandoned.

(51) Int. Cl.[7] .................................................. C12Q 1/68
(52) U.S. Cl. ............................................... 435/6; 435/4
(58) Field of Search ......................................... 435/6, 4

(56) References Cited

U.S. PATENT DOCUMENTS

| | | | |
|---|---|---|---|
| 5,616,561 A | | 4/1997 | Barcellos-Hoff |
| 5,827,733 A | | 10/1998 | Lee et al. |
| 5,994,618 A | * | 11/1999 | Lee et al. |
| 6,096,506 A | * | 8/2000 | Lee et al. |
| 6,103,466 A | | 8/2000 | Grobet et al. |

FOREIGN PATENT DOCUMENTS

| | | |
|---|---|---|
| WO | WO 91/08291 | 6/1991 |
| WO | WO 94/21681 | 9/1994 |
| WO | WO 96/01845 | 1/1996 |
| WO | WO 98/33887 | 8/1998 |

OTHER PUBLICATIONS

Grobet et al., "Molecular definition of an allelic series of mutations disrupting the myostatin function and causing double–muscling in cattle," *Mammalian Genome*, 9, 210–213 (1998).
McPherron and Lee, "Double muscling in cattle due to mutations in the myostatin gene," *Proc. Natl. Acad. Sci. USA*, 94:12457–12461 (Nov. 1997).
Westhusin, "From mighty mice to mighty cows," *Nature Genetics*, 17:4–5 (Sep. 1997).
Grobet et al., "A deletion in the bovine myostatin gene causes the double–muscled phenotype in cattle," *Nature Genetics*, 17:71–74 (Sep. 1997).
McPherron et al., "Regulation of skeletal muscle mass in mice by a new TGF–β superfamily member," *Letters to Nature*, 387:83–90 (May 1997).
Kambadur et al., "Mutations in *myostatin* (*GDF8*) in Double–Muscled Belgian Blue and Piedmontese Cattle," *Genome Research* 7:910–915 (1997).
Slack, J.M.W., "Growth Contro: action mouse," *Current Biology*. Aug. 1, 1997, vol. 7, No. 8, pp. R467–R469.
Love et al., "Transgenic birds by DNA microinjection", *Bio/Technology*, 1/94, vol. 12, No. 1, pp. 60–63.
Callard et al., The Cytokine FactsBook, Academic Press, London, p. 31, 1994.*
Callard et al., The Cytokine FactsBook, Academic Press, London, p. 31, 1987.*
McDowell et al. Effects of Exogenous Growth Hormone on Milk Production and Nutrient Uptake by Muscle and Mammary Tissues of Dairy Cows in Mid–Lactation. Australian Journal of Biological Sciences, vol. 40, No. 3 pp. 295–306.
Evock et al. Pituitary Porcine Growth Hormone (pGH) and a Recombinant pGH Analog Stimulate Pig Growth performance in a Similar Manner. Journal of amiomal Science, vol. 66, No. 8 pp. 1928–1941.
Flakoll et al. Influence of Alpha Ketoisocaproate on Lamb Growthh, Feed, Conversion, and Carcass Cpompostion. Journal of Animal Science, vol. 69, No. 4, pp. 1461–1467.
Deli et al. Biochemical Study of Muscle Samples from chicken Embryos Affected by Wofatox 50 EC. Archives of Toxicology, vol. 8, pp. 277–279.
Faulkner et al. Effect of Testosterone Propionate on Performance and Carcass Characteristics of Heifers and Cows, Journal of Animal Science, vol. 67, No. 8, pp. 1907–1915.
Zhu et al. Survey of Major Histocompatibility Complex Class II Haplotypes in Four Turkey Lines Using Restriction Fragment Length Polymorphism Analysis with Nonradioactive DNA Detection. Poultry Science, vol. 74, No. 7, pp. 1067–1073.
Constam and Robertson, "Regulation of Bone Morphogenetic Protein Activity by Pro Domains and Proprotein Convertases," J. Cell. Biol., vol. 144, No. 1, Jan. 1999, pp. 139–149.

* cited by examiner

*Primary Examiner*—Elizabeth Kemmerer
(74) *Attorney, Agent, or Firm*—Gray Cary Ware & Freidenrich, LLP; Lisa A. Haile; Richard J. Imbra

(57) ABSTRACT

The present invention relates to a method for detecting a polynucleotide encoding GDF-8 in a sample by contacting the sample with an oligonucleotide probe that hybridizes specifically with a polynucleotide encoding GDF-8; and detecting specific hybridization of the oligonucleotide probe to a polynucleotide in the sample, thereby detecting a polynucleotide encoding GDF-8 in the sample. The sample can be a tissue sample or a cell sample, for example, a muscle cell sample, which can be obtained, for example, from a mammal such as a bovine, ovine or porcine mammal, or a human.

33 Claims, 31 Drawing Sheets

HEART
LUNG
THYMUS
BRAIN
KIDNEY
SEMINAL VESICLE
PANCREAS
INTESTINE
SPLEEN
TESTIS
FAT
UTERUS
OVARY
LIVER
MUSCLE

```
  1 TTAAGGTAGGAAGGATTTCAGGCTCTATTTACATAATTGTTCTTTCCTTTTCACACAGAA  60
                                                              N
 61 TCCCTTTTTAGAAGTCAAGGTGACAGACACACCCAAGAGGTCCCGGAGAGACTTTGGGCT 120
      P  F  L  E  V  K  V  T  D  T  P │K  R│ S │R  R│ D  F  G  L
121 TGACTGCGATGAGCACTCCACGGAATCCCGGTGCTGCCGCTACCCCCTCACGGTCGATTT 180
      D  C  D  E  H  S  T  E  S  R  C  C  R  Y  P  L  T  V  D  F
181 TGAAGCCTTTGGATGGACTGGATTATCGCACCCAAAAGATATAAGGCCAATTACTGCTC 240
      E  A  F  G  W  D  W  I  I  A  P  K  R  Y  K  A  N  Y  C  S
241 AGGAGAGTGTGAATTTGTGTTTTTACAAAAATATCCGCATACTCATCTTGTGCACCAAGC 300
      G  E  C  E  F  V  F  L  Q  K  Y  P  H  T  H  L  V  H  Q  A
301 AAACCCCAGAGGCTCAGCAGGCCCTTGCTGCACTCCGACAAAAATGTCTCCCATTAATAT 360
      N  P  R  G  S  A  G  P  C  C  T  P  T  K  M  S  P  I  N  M
361 GCTATATTTTAATGGCAAAGAACAAATAATATATGGGAAAATTCCAGCCATGGTAGTAGA 420
      L  Y  F  N  G  K  E  Q  I  I  Y  G  K  I  P  A  M  V  V  D
421 CCGCTGTGGGTGCTCATGAGCTTTGCATTAGGTTAGAAACTTCCCAAGTCATGGAAGGTC 480
      R  C  G  C  S  *
481 TTCCCCTCAATTTCGAAACTGTGAATTCCTGCAGCCCGGGGGATCCACTAGTTCTAGAGC 540
541 GGCCGCCACC  550
```

FIG. 2A

```
  1 CAAAAAGATCCAGAAGGGATTTTGGTCTTGACTGTGATGAGCACTCAACAGAATCACGAT  60
     │K  R│ S │R  R│ D  F  G  L  D  C  D  E  H  S  T  E  S  R  C
 61 GCTGTCGTTACCCTCTAACTGTGGATTTTGAAGCTTTTGGATGGGATTGGATTATCGCTC 120
      C  R  Y  P  L  T  V  D  F  E  A  F  G  W  D  W  I  I  A  P
121 CTAAAAGATATAAGGCCAATTACTGCTCTGGAGAGTGTGAATTTGTATTTTTACAAAAAT 180
      K  R  Y  K  A  N  Y  C  S  G  E  C  E  F  V  F  L  Q  K  Y
181 ATCCTCATACTCATCTGGTACACCAAGCAAACCCCAGAGGTTCAGCAGGCCCTTGCTGTA 240
      P  H  T  H  L  V  H  Q  A  N  P  R  G  S  A  G  P  C  C  T
241 CTCCCACAAAGATGTCTCCAATTAATATGCTATATTTTAATGGCAAAGAACAAATAATAT 300
      P  T  K  M  S  P  I  N  M  L  Y  F  N  G  K  E  Q  I  I  Y
301 ATGGGAAAATTCCAGCGATGGTAGTA  326
      G  K  I  P  A  M  V  V
```

FIG. 2B

```
GAA GAT GGG CTG AAT CCC TTT TTA GAA GTC AAA GTA ACA GAC ACA CCC AAG AGG TCC CGG
 E   D   G   L   N   P   F   L   E   V   K   V   T   D   T   P   K   R   S   R

AGA GAC TTT GGG CTT GAC TGT GAT GAA CAC TCC ACG GAA TCG CGG TGC TGT CGC TAC CCC
 R   D   F   G   L   D   C   D   E   H   S   T   E   S   R   C   C   R   Y   P

CTC ACG GTC GAT TTC GAA GCC TTT GGA TGG GAC TGG ATT ATT GCA CCC AAA AGA TAT AAG
 L   T   V   D   F   E   A   F   G   W   D   W   I   I   A   P   K   R   Y   K

GCT AAT TAC TGC TCT GGA GAG TGT GAA TTT GTG TTC TTA CAA AAA TAT CCG CAT ACT CAT
 A   N   Y   C   S   G   E   C   E   F   V   F   L   Q   K   Y   P   H   T   H

CTT GTG CAC CAA GCA AAC CCC AGA GGC TCG GCA GGC CCT TGC TGC ACG CCA ACA AAA ATG
 L   V   H   Q   A   N   P   R   G   S   A   G   P   C   C   T   P   T   K   M

TCT CCC ATT AAT ATG CTA TAT TTT AAT GGC AAA GAA CAA ATA ATA TAT GGG AAA ATT CCA
 S   P   I   N   M   L   Y   F   N   G   K   E   Q   I   I   Y   G   K   I   P

GCC ATG GTA GTA GAC CGG TGT GGG TGC TCG TGA GCT TTG CAT TAG CTT TAA AAT TTC CCA
 A   M   V   V   D   R   C   G   C   S   *

AAT CGT GGA AGG TCT TCC CCT CGA TTT CGA AAC TGT GAA TTT ATG TAC CAC AGG CTG TAG
```

RAT GDF-8

FIG. 2C

FIG. 2D CHICKEN GDF-8

```
TTA GTA AAG GCA CAA TTA TGG ATA TAC TTG AGG CAA GTC CAA AAA CCT ACA ACG GTG
 L   V   K   A   Q   L   W   I   Y   L   R   Q   V   Q   K   P   T   T   V

TTT GTG CAG ATC CTG AGA AAA ATT AAG CCC ATG ATG AAA GAC GGT ACA AGA TAT ACT GGA ATT
 F   V   Q   I   L   R   K   I   K   P   M   M   K   D   G   T   R   Y   T   G   I

GGA TCT TTG AAA CTT GAC ATG AAC CCA GGC ACT GAA CCT GGT ATC CAG AGT ATT GAT ATA AAA GCT
 G   S   L   K   L   D   M   N   P   G   T   E   P   G   I   Q   S   I   D   I   K   A

ACA GTG CTG CAA AAT TGG CTC CAA ACG GAT GTT GCT CTT AGA ACA AAT TTA GGC ATC GAA GAT GTG TTG
 T   V   L   Q   N   W   L   Q   T   D   V   A   L   R   T   N   L   G   I   E   D   V   L

TTT GAT GAG TTA GAG ACT GAG GTC AGA GGC CAC TCC CGA TGT TGT AAA AGA CAC ACT CCG GAT GGA TTT
 F   D   E   L   E   T   E   V   R   G   H   S   R   C   C   K   R   H   T   P   D   G   F

AAC CCA GAG GAG TTT GAC TGG GAC TTT GTG AAA GCA GAA GAA TAC CCC CCG TCC CGC TAC CCA CTG GAT
 N   P   E   E   F   D   W   D   F   V   K   A   E   E   Y   P   P   S   R   Y   P   L   D

TTC GAG GAA TTT GGA TGG GAC TGG ATT ATA GCA CCT AAA AGA TAC AAA GCC AAC TAC TGT TCA GGC CAG
 F   E   E   F   G   W   D   W   I   I   A   P   K   R   Y   K   A   N   Y   C   S   G   Q

TCC GGA GAA TGC TCA TGC TGC CGC CCT AGA GGC CCT CAC TGT GGA CAG CAA GCC CCC CAT CTG CAC TGC
 S   G   E   C   S   C   C   R   P   R   G   P   H   C   G   Q   Q   A   P   H   L   H   C

GCA AAT GGA AAT GGA AAA GAA CAA CGG CCT CGT CAT TGC CAA CCC ATT CTT TAC AAG ATG TCC CCT ATA AAC
 A   N   G   N   G   K   E   Q   R   P   R   H   C   Q   P   I   L   Y   K   M   S   P   I   N

ATG CTG TAT TTC AAT GGA AAG GAA CAG ATA ATA TAT GGA AAG ATA CCA GCC ATG GTA GTT
 M   L   Y   F   N   G   K   E   Q   I   I   Y   G   K   I   P   A   M   V   V

GAT CGT TGT GGG TGC TCA TGA GGC TGT CGT GAG ATC CAC CAT CCG ATA AAT TGT GAA ATT ACG TAC GCT
 D   R   C   G   C   S   *   G   C   R   E   I   H   H   P   I   N   C   E   I   T   Y   A

CAC CAA AAA AAA CTA TAT CCC CTC ATC CAT CTT TGA AAC TGT GAA ATT ACG TAC GCT

AGG CAT TGC C
```

FIG. 3A

```
                                                                            80
human    1  MQKLQLCVYIYLFMLIVAGPVDLNENSEQKENVEKEGLCNACTWRQNTKSRIEAIKIQILSKLRLETAPNISKDVIRQ
murine      MMQKLQMVYIYLFMLIAAGPVDLNEGSEKEENVEKEGLCNACAWRQNTRYSRIEAIKIQILSKLRLETAPNISKDAIRQ
rat
chicken 160
human   81  LLPKAPPLRELIDQYDVQRDDSSDGSLEDDYHATTETIITMPTESDFLMQVDGKPKCCFFKFSSKIQYNKVVKAQLWIY
murine      LLPRAPPLRELIDQYDVQRDDSSDGSLEDDYHATTETIITMPTESDFLMQADGKPKCCFFKFSSKIQYNKVVKAQLWIY
rat
chicken                                                              LVVKAQLWIY 240
human  161  LRPVETPTTVFVQILRLIKPMKDGTRYTGIRSLKLDMNPGTGIWQSIDVKTVLQNWLKQPESNLGIEIKALDENGHDLAV
murine      LRPVKTPTTVFVQILRLIKPMKDGTRYTGIRSLKLDMNPGTGIWQSIDVKTVLQNWLKQPESNLGIEIKALDENGHDLAV
rat         LRQVQKPTTVFVQILRLIKPMKDGTRYTGIGSLKLDMNPGTGIWQSIDVKTVLQNWLKQPESNLGIEIKAFDETGRDLAV
chicken 320
human  241  TFPGPGEDGLNPFLEVKVTDTPKRSRRDFGLDCDEHSTESRCCRTPLTVDFEAFGWDWIIAPKRYKANYCSGECEFVFLQ
murine      TFPGPGEDGLNPFLEVKVTDTPKRSRRDFGLDCDEHSTESRCCRYPLTVDFEAFGWDWIIAPKRYKANYCSGECEFVFLQ
rat         EDGLNPFLEVKVTDTPKRSRRDFGLDCDEHSTESRCCRYPLTVDFEAFGWDWIIAPKRYKANYCSGECEFVFLQ
chicken     TFPGPGEDGLNPFLEVRVTDTPKRSRRDFGLDCDEHSTESRCCRYPLTVDFEAFGWDWIIAPKRYKANYCSGECEFVFLQ 376
human  321  KYPHTHLVHQANPRGSAGPCCTPTKMSPINMLYFNGKEQIIYGKIPAMVVDRCGCS
murine      KYPHTHLVHQANPRGSAGPCCTPTKMSPINMLYFNGKEQIIYGKIPAMVVDRCGCS
rat         KYPHTHLVHQANPRGSAGPCCTPTKMSPINMLYFNGKEQIIYGKIPAMVVDRCGCS
chicken     KYPHTHLVHQANPRGSAGPCCTPTKMSPINMLYFNGKEQIIYGKIPAMVVDRCGCS
```

FIG. 3B

| | GDF-1 | GDF-2 | GDF-3 | GDF-5 | GDF-6 | GDF-7 | GDF-8 | GDF-9 | BMP-2 | BMP-4 | Vgr-1 | OP-1 | BMP-5 | BMP-3 | MIS | Inhibinα | InhibinβA | InhibinβB | TGG-β1 | TGF-β2 | TGF-β3 |
|---|---|---|---|---|---|---|---|---|---|---|---|---|---|---|---|---|---|---|---|---|---|
| TGF-β3 | 33 | 30 | 32 | 37 | 38 | 38 | 37 | 25 | 36 | 35 | 39 | 38 | 36 | 32 | 25 | 24 | 36 | 37 | 78 | 82 | 100 |
| TGF-β2 | 32 | 28 | 31 | 34 | 36 | 35 | 37 | 25 | 34 | 33 | 37 | 38 | 35 | 32 | 23 | 22 | 37 | 34 | 74 | 100 | - |
| TGF-β1 | 33 | 26 | 36 | 33 | 35 | 36 | 34 | 23 | 35 | 34 | 35 | 34 | 34 | 32 | 28 | 23 | 41 | 35 | 100 | - | - |
| InhibinβB | 35 | 25 | 41 | 37 | 39 | 36 | 42 | 31 | 42 | 42 | 41 | 42 | 37 | 37 | 25 | 25 | 63 | 100 | - | - | - |
| InhibinβA | 37 | 32 | 42 | 40 | 43 | 41 | 38 | 30 | 42 | 41 | 44 | 43 | 43 | 36 | 24 | 26 | 100 | - | - | - | - |
| Inhibinα | 23 | 20 | 25 | 24 | 27 | 26 | 26 | 27 | 22 | 22 | 25 | 24 | 24 | 29 | 18 | 100 | - | - | - | - | - |
| MIS | 34 | 20 | 22 | 27 | 26 | 25 | 31 | 21 | 27 | 27 | 24 | 27 | 24 | 30 | 100 | - | - | - | - | - | - |
| BMP-3 | 42 | 34 | 42 | 47 | 46 | 46 | 38 | 29 | 48 | 47 | 44 | 42 | 43 | 100 | - | - | - | - | - | - | - |
| BMP-5 | 46 | 55 | 50 | 52 | 54 | 52 | 42 | 31 | 61 | 59 | 91 | 88 | 100 | - | - | - | - | - | - | - | - |
| OP-1 | 47 | 52 | 50 | 51 | 53 | 53 | 42 | 30 | 60 | 58 | 87 | 100 | - | - | - | - | - | - | - | - | - |
| Vgr-1 | 46 | 55 | 53 | 51 | 53 | 52 | 45 | 31 | 61 | 60 | 100 | - | - | - | - | - | - | - | - | - | - |
| BMP-4 | 43 | 51 | 50 | 57 | 56 | 57 | 38 | 34 | 92 | 100 | - | - | - | - | - | - | - | - | - | - | - |
| BMP-2 | 42 | 52 | 53 | 57 | 57 | 57 | 41 | 33 | 100 | - | - | - | - | - | - | - | - | - | - | - | - |
| GDF-9 | 27 | 32 | 33 | 33 | 34 | 33 | 27 | 100 | - | - | - | - | - | - | - | - | - | - | - | - | - |
| GDF-8 | 35 | 31 | 41 | 37 | 38 | 37 | 100 | - | - | - | - | - | - | - | - | - | - | - | - | - | - |
| GDF-7 | 48 | 48 | 46 | 80 | 80 | 100 | - | - | - | - | - | - | - | - | - | - | - | - | - | - | - |
| GDF-6 | 44 | 51 | 49 | 86 | 100 | - | - | - | - | - | - | - | - | - | - | - | - | - | - | - | - |
| GDF-5 | 46 | 47 | 49 | 100 | - | - | - | - | - | - | - | - | - | - | - | - | - | - | - | - | - |
| GDF-3 | 50 | 42 | 100 | - | - | - | - | - | - | - | - | - | - | - | - | - | - | - | - | - | - |
| GDF-2 | 33 | 100 | - | - | - | - | - | - | - | - | - | - | - | - | - | - | - | - | - | - | - |
| GDF-1 | 100 | - | - | - | - | - | - | - | - | - | - | - | - | - | - | - | - | - | - | - | - |

FIG. 4

```
  1 GTCTCTCGGACGGTACATGCACTAATATTTCACTTGGCATTACTCAAAAGCAAAAAGAAG  60
 61 AAATAAGAACAAGGGAAAAAAAAAGATTGTGCTGATTTTTAAAATGATGCAAAAACTGCA 120
                                                M  M  Q  K  L  Q
121 AATGTATGTTTATATTTACCTGTTCATGCTGATTGCTGCTGGCCCAGTGGATCTAAATGA 180
     M  Y  V  Y  I  Y  L  F  M  L  I  A  A  G  P  V  D  L  N  E
181 GGGCAGTGAGAGAGAAGAAAATGTGGAAAAGAGGGGCTGTGTAATGCATGTGCGTGGAG  240
     G  S  E  R  E  E  N  V  E  K  E  G  L  C  N  A  C  W  R
241 ACAAAACACGAGGTACTCCAGAATAGAAGCCATAAAAATTCAAATCCTCAGTAAGCTGCG 300
     Q  N  T  R  Y  S  R  I  E  A  I  K  I  Q  I  L  S  K  L  R
301 CCTGGAAACAGCTCCTAACATCAGCAAAGATGCTATAAGACAACTTCTGCCAAGAGCGCC 360
     L  E  T  A  P [ N  I  S ] K  D  A  I  R  Q  L  L  P  R  A  P
361 TCCACTCCGGGAACTGATCGATCAGTACGACGTCCAGAGGGATGACAGCAGTGATGGCTC 420
     P  L  R  E  L  I  D  Q  Y  D  V  Q  R  D  D  S  S  D  G  S
421 TTTGGAAGATGACGATTATCACGCTACCACGGAAACAATCATTACCATGCCTACAGAGTC 480
     L  E  D  D  D  Y  H  A  T  T  E  T  I  I  T  M  P  T  E  S
481 TGACTTTCTAATGCAAGCGGATGGCAAGCCCAAATGTTGCTTTTTTAAATTTAGCTCTAA 540
     D  F  L  M  Q  A  D  G  K  P  K  C  C  F  F  K  F  S  S  K
541 AATACAGTACAACAAAGTAGTAAAAGCCCAACTGTGGATATATCTCAGACCCGTCAAGAC 600
     I  Q  Y  N  K  V  V  K  A  Q  L  W  I  Y  L  R  P  V  K  T
601 TCCTACAACAGTGTTTGTGCAAATCCTGAGACTCATCAAACCCATGAAAGACGGTACAAG 660
     P  T  T  V  F  V  Q  I  L  R  L  I  K  P  M  K  D  G  T  R
661 GTATACTGGAATCCGATCTCTGAAACTTGACATGAGCCCAGGCACTGGTATTTGGCAGAG 720
     Y  T  G  I  R  S  L  K  L  D  M  S  P  G  T  G  I  W  Q  S
721 TATTGATGTGAAGACAGTGTTGCAAAATTGGCTCAAACAGCCTGAATCCAACTTAGGCAT 780
     I  D  V  K  T  V  L  Q  N  W  L  K  Q  P  E  S  N  L  G  I
781 TGAAATCAAAGCTTTGGATGAGAATGGCCATGATCTTGCTGTAACCTTCCCAGGACCAGG 840
     E  I  K  A  L  D  E  N  G  H  D  L  A  V  T  F  P  G  P  G
841 AGAAGATGGGCTGAATCCCTTTTTAGAAGTCAAGGTGACAGACACACCCAAGAGGTCCCG 900
     E  D  G  L  N  P  F  L  E  V  K  V  T  D  T  P  K [ R  S  R
901 GAGAGACTTTGGGCTTGACTGCGATGAGCACTCCACGGAATCCCGGTGCTGCCGCTACCC 960
     R ] D  F  G  L  D  C  D  E  H  S  T  E  S  R  C  C  R  Y  P
961 CCTCACGGTCGATTTTGAAGCCTTTGGATGGGACTGGATTATCGCACCCAAAAGATATAA 1020
     L  T  V  D  F  E  A  F  G  W  D  W  I  I  A  P  K  R  Y  K
1021 GGCCAATTACTGCTCAGGAGAGTGTGAATTTGTGTTTTTACAAAAATATCCGCATACTCA 1080
     A  N  Y  C  S  G  E  C  E  F  V  F  L  Q  K  Y  P  H  T  H
1081 TCTTGTGCACCAAGCAAACCCCAGAGGCTCAGCAGGCCCTTGCTGCACTCCGACAAAAAT 1140
     L  V  H  Q  A  N  P  R  G  S  A  G  P  C  C  T  P  T  K  M
1141 GTCTCCCATTAATATGCTATATTTTAATGGCAAAGAACAAATAATATATGGGAAATTCC  1200
     S  P  I  N  M  L  Y  F  N  G  K  E  Q  I  I  Y  G  K  I  P
1201 AGCCATGGTAGTAGACCGCTGTGGGTGCTCATGAGCTTTGCATTAGGTTAGAAACTTCCC 1260
     A  M  V  V  D  R  C  G  C  S  *
```

FIG. 5A

```
1261 AAGTCATGGAAGGTCTTCCCCTCAATTTCGAAACTGTGAATTCAAGCACCACAGGCTGTA 1320
1321 GGCCTTGAGTATGCTCTAGTAACGTAAGCACAAGCTACAGTGTATGAACTAAAAGAGAGA 1380
1381 ATAGATGCAATGGTTGGCATTCAACCACCAAAATAAACCATACTATAGGATGTTGTATGA 1440
1441 TTTCCAGAGTTTTTGAAATAGATGGAGATCAAATTACATTTATGTCCATATATGTATATT 1500
1501 ACAACTACAATCTAGGCAAGGAAGTGAGAGCACATCTTGTGGTCTGCTGAGTTAGGAGGG 1560
1561 TATGATTAAAAGGTAAAGTCTTATTTCCTAACAGTTTCACTTAATATTTACAGAAGAATC 1620
1621 TATATGTAGCCTTTGTAAAGTGTAGGATTGTTATCATTTAAAAACATCATGTACACTTAT 1680
1681 ATTTGTATTGTATACTTGGTAAGATAAAATTCCACAAAGTAGGAATGGGGCCTCACATAC 1740
1741 ACATTGCCATTCCTATTATAATTGGACAATCCACCACGGTGCTAATGCAGTGCTAATGG 1800
1801 CTCCTACTGGACCTCTCGATAGAACACTCTACAAAGTACGAGTCTCTCTCTCCCTTCCAG 1860
1861 GTGCATCTCCACACACACAGCACTAAGTGTTCAATGCATTTTCTTTAAGGAAAGAAGAAT 1920
1921 CTTTTTTTCTAGAGGTCAACTTTCAGTCAACTCTAGCACAGCGGGAGTGACTGCTGCATC 1980
1981 TTAAAAGGCAGCCAAACAGTATTCATTTTTTAATCTAAATTTCAAAATCACTGTCTGCCT 2040
2041 TTATCACATGGCAATTTGTGGTAAAATAATGGAAATGACTGGTTCTATCAATATTGTAT 2100
2101 AAAAGACTCTGAAACAATTACATTTATATAATATGTATACAATATTGTTTTGTAAATAAG 2160
2161 TGTCTCCTTTTATATTTACTTTGGTATATTTTTACACTAATGAAATTTCAAATCATTAAA 2220
2221 GTACAAAGACATGTCATGTATCACAAAAAAGGTGACTGCTTCTATTTCAGAGTGAATTAG 2280
2281 CAGATTCAATAGTGGTCTTAAAACTCTGTATGTTAAGATTAGAAGGTTATATTACAATCA 2340
2341 ATTTATGTATTTTTACATTATCAACTTATGGTTTCATGGTGGCTGTATCTATGAATGTG 2400
2401 GCTCCCAGTCAAATTTCAATGCCCCACCATTTTAAAAATTACAAGCATTACTAAACATAC 2460
2461 CAACATGTATCTAAAGAAATACAAATATGGTATCTCAATAACAGCTACTTTTTATTTTA 2520
2521 TAATTTGACAATGAATACATTTCTTTATTTACTTCAGTTTTATAAATTGGAACTTTGTT 2580
2581 TATCAAATGTATTGTACTCATAGCTAAATGAATTATTTCTTACATAAAAATGTGTAGAA 2640
2641 ACTATAAATTAAAGTGTTTTCACATTTTTGAAAGGC  2676
```

FIG. 5B

```
   1 AAGAAAAGTAAAAGGAAGAAACAAGAACAAGAAAAAAGATTATATTGATTTTAAAATCAT  60
                                                              M
  61 GCAAAAACTGCAACTCTGTGTTTATATTTACCTGTTTATGCTGATTGTTGCTGGTCCAGT 120
      Q  K  L  Q  L  C  V  Y  I  Y  L  F  M  L  I  V  A  G  P  V
 121 GGATCTAAATGAGAACAGTGAGCAAAAAGAAAATGTGGAAAAAGAGGGGCTGTGTAATGC 180
      D  L  N  E  N  S  E  Q  K  E  N  V  E  K  E  G  L  C  N  A
 181 ATGTACTTGGAGACAAAACACTAAATCTTCAAGAATAGAAGCCATTAAGATACAAATCCT 240
      C  T  W  R  Q  N  T  K  S  S  R  I  E  A  I  K  I  Q  I  L
 241 CAGTAAACTTCGTCTGGAAACAGCTCCTAACATCAGCAAAGATGTTATAAGACAACTTTT 300
      S  K  L  R  L  E  T  A  P [N  I  S] K  D  V  I  R  Q  L  L
 301 ACCCAAAGCTCCTCCACTCCGGGAACTGATTGATCAGTATGATGTCCAGAGGGATGACAG 360
      P  K  A  P  P  L  R  E  L  I  D  Q  Y  D  V  Q  R  D  D  S
 361 CAGCGATGGCTCTTTGGAAGATGACGATTATCACGCTACAACGGAAACAATCATTACCAT 420
      S  D  G  S  L  E  D  D  D  Y  H  A  T  T  E  T  I  I  T  M
 421 GCCTACAGAGTCTGATTTTCTAATGCAAGTGGATGGAAAACCCAAATGTTGCTTCTTTAA 480
      P  T  E  S  D  F  L  M  Q  V  D  G  K  P  K  C  C  F  F  K
 481 ATTTAGCTCTAAAATACAATACAATAAAGTAGTAAAGGCCCAACTATGGATATATTTGAG 540
      F  S  S  K  I  Q  Y  N  K  V  V  K  A  Q  L  W  I  Y  L  R
 541 ACCCGTCGAGACTCCTACAACAGTGTTTGTGCAAATCCTGAGACTCATCAAACCTATGAA 600
      P  V  E  T  P  T  T  V  F  V  Q  I  L  R  L  I  K  P  M  K
 601 AGACGGTACAAGGTATACTGGAATCCGATCTCTGAAACTTGACATGAACCCAGGCACTGG 660
      D  G  T  R  Y  T  G  I  R  S  L  K  L  D  M  N  P  G  T  G
 661 TATTTGGCAGAGCATTGATGTGAAGACAGTGTTGCAAAATTGGCTCAAACAACCTGAATC 720
      I  W  Q  S  I  D  V  K  T  V  L  Q  N  W  L  K  Q  P  E  S
 721 CAACTTAGGCATTGAAATAAAAGCTTTAGATGAGAATGGTCATGATCTTGCTGTAACCTT 780
      N  L  G  I  E  I  K  A  L  D  E  N  G  H  D  L  A  V  T  F
 781 CCCAGGACCAGGAGAAGATGGGCTGAATCCGTTTTTAGAGGTCAAGGTAACAGACACACC 840
      P  G  P  G  E  D  G  L  N  P  F  L  E  V  K  V  T  D  T  P
 841 AAAAAGATCCAGAAGGGATTTTGGTCTTGACTGTGATGAGCACTCAACAGAATCACGATG 900
      K [R  S  R  R] D  F  G  L  D  C  D  E  H  S  T  E  S  R  C
 901 CTGTCGTTACCCTCTAACTGTGGATTTTGAAGCTTTTGGATGGGATTGGATTATCGCTCC 960
      C  R  Y  P  L  T  V  D  F  E  A  F  G  W  D  W  I  I  A  P
 961 TAAAAGATATAAGGCCAATTACTGCTCTGGAGAGTGTGAATTTGTATTTTTACAAAAATA 1020
      K  R  Y  K  A  N  Y  C  S  G  E  C  E  F  V  F  L  Q  K  Y
1021 TCCTCATACTCATCTGGTACACCAAGCAAACCCCAGAGGTTCAGCAGGCCCTTGCTGTAC 1080
      P  H  T  H  L  V  H  Q  A  N  P  R  G  S  A  G  P  C  C  T
1081 TCCCACAAAGATGTCTCCAATTAATATGCTATATTTTAATGGCAAAGAACAAATAATATA 1140
      P  T  K  M  S  P  I  N  M  L  Y  F  N  G  K  E  Q  I  I  Y
1141 TGGGAAAATTCCAGCGATGGTAGTAGACCGCTGTGGGTGCTCATGAGATTTATATTAAGC 1200
      G  K  I  P  A  M  V  V  D  R  C  G  C  S  *
```

FIG. 5C

```
1201 GTTCATAACTTCCTAAAACATGGAAGGTTTTCCCCTCAACAATTTTGAAGCTGTGAAATT 1260
1261 AAGTACCACAGGCTATAGGCCTAGAGTATGCTACAGTCACTTAAGCATAAGCTACAGTAT 1320
1321 GTAAACTAAAAGGGGGAATATATGCAATGGTTGGCATTTAACCATCCAAACAAATCATAC 1380
1381 AAGAAAGTTTTATGATTTCCAGAGTTTTTGAGCTAGAAGGAGATCAAATTACATTTATGT 1440
1441 TCCTATATATTACAACATCGGCGAGGAAATGAAAGCGATTCTCCTTGAGTTCTGATGAAT 1500
1501 TAAAGGAGTATGCTTTAAAGTCTATTTCTTTAAAGTTTTGTTTAATATTTACAGAAAAAT 1560
1561 CCACATACAGTATTGGTAAAATGCAGGATTGTTATATACCATCATTCGAATCATCCTTAA 1620
1621 ACACTTGAATTTATATTGTATGGTAGTATACTTGGTAAGATAAAATTCCACAAAAATAGG 1680
1681 GATGGTGCAGCATATGCAATTTCCATTCCTATTATAATTGACACAGTACATTAACAATCC 1740
1741 ATGCCAACGGTGCTAATACGATAGGCTGAATGTCTGAGGCTACCAGGTTTATCACATAAA 1800
1801 AAACATTCAGTAAAATAGTAAGTTTCTCTTTTCTTCAGGTGCATTTTCCTACACCTCCAA 1860
1861 ATGAGGAATGGATTTTCTTTAATGTAAGAAGAATCATTTTTCTAGAGGTTGGCTTTCAAT 1920
1921 TCTGTAGCATACTTGGAGAAACTGCATTATCTTAAAAGGCAGTCAAATGGTGTTTGTTTT 1980
1981 TATCAAAATGTCAAAATAACATACTTGGAGAAGTATGTAATTTTGTCTTTGGAAAATTAC 2040
2041 AACACTGCCTTTGCAACACTGCAGTTTTTATGGTAAAATAATAGAAATGATCGACTCTAT 2100
2101 CAATATTGTATAAAAAGACTGAAACAATGCATTTATATAATATGTATACAATATTGTTTT 2160
2161 GTAAATAAGTGTCTCCTTTTTTATTTACTTTGGTATATTTTACACTAAGGACATTTCAA 2220
2221 ATTAAGTACTAAGGCACAAAGACATGTCATGCATCACAGAAAAGCAACTACTTATATTTC 2280
2281 AGAGCAAATTAGCAGATTAAATAGTGGTCTTAAAACTCCATATGTTAATGATTAGATGGT 2340
2341 TATATTACAATCATTTATATTTTTTTACATGATTAACATTCACTTATGGATTCATGATG 2400
2401 GCTGTATAAAGTGAATTTGAAATTTCAATGGTTTACTGTCATTGTGTTTAAATCTCAACG 2460
2461 TTCCATTATTTTAATACTTGCAAAAACATTACTAAGTATACCAAAATAATTGACTCTATT 2520
2521 ATCTGAAATGAAGAATAAACTGATGCTATCTCAACAATAACTGTTACTTTTATTTTATAA 2580
2581 TTTGATAATGAATATATTTCTGCATTTATTTACTTCTGTTTTGTAAATTGGGATTTTGTT 2640
2641 AATCAAATTTATTGTACTATGACTAAATGAAATTATTTCTTACATCTAATTTGTAGAAAC 2700
2701 AGTATAAGTTATATTAAAGTGTTTTCACATTTTTTGAAAGAC 2743
```

FIG. 5D

```
  1    MMQKLQMYVYIYLFMLIAAGPVDLNEGSEREENVEKEGLCNACAWRQNTR    50
       |||||   ||||||||  |||||||  ||  ||||||||||||  |||||
  1    MQKLQLCVYIYLFMLIVAGPVDLNENSEQKENVEKEGLCNACTWRQNTK    49

51    YSRIEAIKIQILSKLRLETAPNISKDAIRQLLPRAPPLRELIDQYDVQRD   100
       ||||||||||||||||||||||||| ||||||| ||||||||||||||||
 50    SSRIEAIKIQILSKLRLETAPNISKDVIRQLLPKAPPLRELIDQYDVQRD    99

101    DSSDGSLEDDDYHATTETIITMPTESDFLMQADGKPKCCFFKFSSKIQYN   150
       |||||||||||||||||||||||||||||| |||||||||||||||||||
100    DSSDGSLEDDDYHATTETIITMPTESDFLMQVDGKPKCCFFKFSSKIQYN   149

151    KVVKAQLWIYLRPVKTPTTVFVQILRLIKPMKDGTRYTGIRSLKLDMSPG   200
       |||||||||||||| |||||||||||||||||||||||||||||||| ||
150    KVVKAQLWIYLRPVETPTTVFVQILRLIKPMKDGTRYTGIRSLKLDMNPG   199

201    TGIWQSIDVKTVLQNWLKQPESNLGIEIKALDENGHDLAVTFPGPGEDGL   250
       ||||||||||||||||||||||||||||||||||||||||||||||||||
200    TGIWQSIDVKTVLQNWLKQPESNLGIEIKALDENGHDLAVTFPGPGEDGL   249

251    NPFLEVKVTDTPKRSRRDFGLDCDEHSTESRCCRYPLTVDFEAFGWDWII   300
       ||||||||||||||||||||||||||||||||||||||||||||||||||
250    NPFLEVKVTDTPKRSRRDFGLDCDEHSTESRCCRYPLTVDFEAFGWDWII   299

301    APKRYKANYCSGECEFVFLQKYPHTHLVHQANPRGSAGPCCTPTKMSPIN   350
       ||||||||||||||||||||||||||||||||||||||||||||||||||
300    APKRYKANYCSGECEFVFLQKYPHTHLVHQANPRGSAGPCCTPTKMSPIN   349

351    MLYFNGKEQIIYGKIPAMVVDRCGCS    376
       |||||||||||||||||||||||||
350    MLYFNGKEQIIYGKIPAMVVDRCGCS    375
```

FIG. 7

HEART
LUNG
THYMUS
BRAIN
KIDNEY
SEMINAL VESICLE
PANCREAS
INTESTINE
SPLEEN
TESTIS
MUSCLE
LIVER
OVARY
FAT
UTERUS

```
1/1                                      31/11
ATG CAA AAA CTG CAA CTC TGT GTT TAT ATT  TAC CTG TTT ATG CTG ATT GTT GCT GGT CCA
 M   Q   K   L   Q   L   C   V   Y   I    Y   L   F   M   L   I   V   A   G   P
61/21                                    91/31
GTG GAT CTA AAT GAG AAC AGT GAG CAA AAA  GAA AAT GTG GAA AAA GAG GGG CTG TGT AAT
 V   D   L   N   E   N   S   E   Q   K    E   N   V   E   K   E   G   L   C   N
121/41                                   151/51
GCA TGT ACT TGG AGA CAA AAC ACT AAA TCT  TCA AGA ATA GAA GCC ATT AAA ATA CAA ATC
 A   C   T   W   R   Q   N   T   K   S    S   R   I   E   A   I   K   I   Q   I
181/61                                   211/71
CTC AGT AAA CTT CGT CTG GAA ACA GCT CCT  AAC ATC AGC AAA GAT GCT ATA AGA CAA CTT
 L   S   K   L   R   L   E   T   A   P    N   I   S   K   D   A   I   R   Q   L
241/81                                   271/91
TTA CCC AAA GCT CCT CCA CTC CGG GAA CTG  ATT GAT CAG TAT GAT GTC CAG AGG GAT GAC
 L   P   K   A   P   P   L   R   E   L    I   D   Q   Y   D   V   Q   R   D   D
301/101                                  331/111
AGC AGC GAT GGC TCT TTG GAA GAT GAC GAT  TAT CAC GCT ACA ACG GAA ACA ATC ATT ACC
 S   S   D   G   S   L   E   D   D   D    Y   H   A   T   T   E   T   I   I   T
361/121                                  391/131
ATG CCT ACA GAG TCT GAT TTT TTA ATG CAA  GTG GAT GGA AAA CCC AAA TGT TGC TTC TTT
 M   P   T   E   S   D   F   L   M   Q    V   D   G   K   P   K   C   C   F   F
421/141                                  451/151
AAA TTT AGC TCT AAA ATA CAA TAC AAT AAA  GTG GTA AAG GCC CAA CTA TGG ATA TAT TTG
 K   F   S   S   K   I   Q   Y   N   K    V   V   K   A   Q   L   W   I   Y   L
481/161                                  511/171
AGA CCC GTC GAG ACT CCT ACA ACA GTG TTT  GTG CAA ATC CTG AGA CTC ATC AAA CCT ATG
 R   P   V   E   T   P   T   T   V   F    V   Q   I   L   R   L   I   K   P   M
541/181                                  571/191
AAA GAC GGT ACA AGG TAT ACT GGA ATC CGA  TCT CTG AAA CTT GAC ATG AAC CCA GGC ACT
 K   D   G   T   R   Y   T   G   I   R    S   L   K   L   D   M   N   P   G   T
601/201                                  631/211
GGT ATT TGG CAG AGC ATT GAT GTG AAG ACA  GTG TTG CAA AAT TGG CTC AAA CAA CCT GAA
 G   I   W   Q   S   I   D   V   K   T    V   L   Q   N   W   L   K   Q   P   E
661/221                                  691/231
TCC AAC TTA GGC ATT GAA ATA AAA GCT TTA  GAT GAG AAT GGT CAT GAT CTT GCT GTA ACC
 S   N   L   G   I   E   I   K   A   L    D   E   N   G   H   D   L   A   V   T
721/241                                  751/251
TTC CCA GGA CCA GGA GAA GAT GGG CTG AAT  CCC TTT TTA GAG GTC AAG GTA ACA GAC ACA
 F   P   G   P   G   E   D   G   L   N    P   F   L   E   V   K   V   T   D   T
781/261                                  811/271
CCA AAA AGA TCC AGA AGG GAT TTT GGT CTT  GAC TGT GAT GAG CAC TCA ACA GAA TCG CGA
 P   K   R   S   R   R   D   F   G   L    D   C   D   E   H   S   T   E   S   R
841/281                                  871/291
TGC TGT CGT TAC CCT CTA ACT GTG GAT TTT  GAA GCT CTT GGA TGG GAT TGG ATT ATC GCT
 C   C   R   Y   P   L   T   V   D   F    E   A   L   G   W   D   W   I   I   A
901/301                                  931/311
CCT AAA AGA TAT AAG GCC AAT TAC TGC TCT  GGA GAG TGT GAA TTT GTA TTT TTA CAA AAA
 P   K   R   Y   K   A   N   Y   C   S    G   E   C   E   F   V   F   L   Q   K
961/321                                  991/331
TAT CCT CAT ACT CAT CTG GTA CAC CAA GCA  AAC CCC AGA GGT TCA GCA GGC CCT TGC TGT
 Y   P   H   T   H   L   V   H   Q   A    N   P   R   G   S   A   G   P   C   C
1021/341                                 1051/351
ACT CCC ACA AAG ATG TCT CCA ATT AAT ATG  CTA TAT TTT AAT GGC AAA GAA CAA ATA ATA
 T   P   T   K   M   S   P   I   N   M    L   Y   F   N   G   K   E   Q   I   I
1081/361                                 1111/371
TAT GGG AAA ATT CCA GCC ATG GTA GTA GAC  CGC TGC GGG TGC TCA TGA
 Y   G   K   I   P   A   M   V   V   D    R   C   G   C   S   *
```

Baboon GDF-8

FIG. 14A

```
1/1                                    31/11
ATG CAA AAA CTG CAA ATC TCT GTT TAT ATT TAC CTA TTT ATG CTG ATT GTT GCT GGC CCA
 M   Q   K   L   Q   I   S   V   Y   I   Y   L   F   M   L   I   V   A   G   P
61/21                                  91/31
GTG GAT CTG AAT GAG AAC AGC GAG CAG AAG GAA AAT GTG GAA AAA GAG GGG CTG TGT AAT
 V   D   L   N   E   N   S   E   Q   K   E   N   V   E   K   E   G   L   C   N
121/41                                 151/51
GCA TGT TTG TGG AGG GAA AAC ACT ACA TCC TCA AGA CTA GAA GCC ATA AAA ATC CAA ATC
 A   C   L   W   R   E   N   T   T   S   S   R   L   E   A   I   K   I   Q   I
181/61                                 211/71
CTC AGT AAA CTT CGC CTG GAA ACA GCT CCT AAC ATC AGC AAA GAT GCT ATC AGA CAA CTT
 L   S   K   L   R   L   E   T   A   P   N   I   S   K   D   A   I   R   Q   L
241/81                                 271/91
TTG CCC AAG GCT CCT CCA CTC CTG GAA CTG ATT GAT CAG TTC GAT GTC CAG AGA GAT GCC
 L   P   K   A   P   P   L   L   E   L   I   D   Q   F   D   V   Q   R   D   A
301/101                                331/111
AGC AGT GAC GGC TCC TTG GAA GAC GAT GAC TAC CAC GCC AGG ACG GAA ACG GTC ATT ACC
 S   S   D   G   S   L   E   D   D   D   Y   H   A   R   T   E   T   V   I   T
361/121                                391/131
ATG CCC ACG GAG TCT GAT CTT CTA ACG CAA GTG GAA GGA AAA CCC AAA TGT TGC TTC TTT
 M   P   T   E   S   D   L   L   T   Q   V   E   G   K   P   K   C   C   F   F
421/141                                451/151
AAA TTT AGC TCT AAG ATA CAA TAC AAT AAA CTA GTA AAG GCC CAA CTG TGG ATA TAT CTG
 K   F   S   S   K   I   Q   Y   N   K   L   V   K   A   Q   L   W   I   Y   L
481/161                                511/171
AGG CCT GTC AAG ACT CCT GCG ACA GTG TTT GTG CAA ATC CTG AGA CTC ATC AAA CCC ATG
 R   P   V   K   T   P   A   T   V   F   V   Q   I   L   R   L   I   K   P   M
541/181                                571/191
AAA GAC GGT ACA AGG TAT ACT GGA ATC CGA TCT CTG AAA CTT GAC ATG AAC CCA GGC ACT
 K   D   G   T   R   Y   T   G   I   R   S   L   K   L   D   M   N   P   G   T
601/201                                631/211
GGT ATT TGG CAG AGC ATT GAT GTG AAG ACA GTG TTG CAG AAC TGG CTC AAA CAA CCT GAA
 G   I   W   Q   S   I   D   V   K   T   V   L   Q   N   W   L   K   Q   P   E
661/221                                691/231
TCC AAC TTA GGC ATT GAA ATC AAA GCT TTA GAT GAG AAT GGC CAT GAT CTT GCT GTA ACC
 S   N   L   G   I   E   I   K   A   L   D   E   N   G   H   D   L   A   V   T
721/241                                751/251
TTC CCA GAA CCA GGA GAA GAT GGA CTG ACT CCT TTT TTA GAA GTC AAG GTA ACA GAC ACA
 F   P   E   P   G   E   D   G   L   T   P   F   L   E   V   K   V   T   D   T
781/261                                811/271
CCA AAA AGA TCT AGG AGA GAT TTT GGG CTT GAT TGT GAT GAA CAC TCC ACA GAA TCT CGA
 P   K   R   S   R   R   D   F   G   L   D   C   D   E   H   S   T   E   S   R
841/281                                871/291
TGC TGT CGT TAC CCT CTA ACT GTG GAT TTT GAA GCT TTT GGA TGG GAT TGG ATT ATT GCA
 C   C   R   Y   P   L   T   V   D   F   E   A   F   G   W   D   W   I   I   A
901/301                                931/311
CCT AAA AGA TAT AAG GCC AAT TAC TGC TCT GGA GAA TGT GAA TTT GTA TTT TTG CAA AAG
 P   K   R   Y   K   A   N   Y   C   S   G   E   C   E   F   V   F   L   Q   K
961/321                                991/331
TAT CCT CAT ACC CAT CTT GTG CAC CAA GCA AAC CCC AGA GGT TCA GCC GGC CCC TGC TGT
 Y   P   H   T   H   L   V   H   Q   A   N   P   R   G   S   A   G   P   C   C
1021/341                               1051/351
ACT CCT ACA AAG ATG TCT CCA ATT AAT ATG CTA TAT TTT AAT GGC GAA GGA CAA ATA ATA
 T   P   T   K   M   S   P   I   N   M   L   Y   F   N   G   E   G   Q   I   I
1081/361                               1111/371
TAC GGG AAG ATT CCA GCC ATG GTA GTA GAT CGC TGT GGG TGT TCA TGA
 Y   G   K   I   P   A   M   V   V   D   R   C   G   C   S   *
```

Bovine GDF-8

FIG. 14B

```
1/1
ATG CAA AAG CTA GCA GTC TAT GTT TAT ATT   TAC CTG TTC ATG CAG ATC GCG GTT GAT CCG
 M   Q   K   L   A   V   Y   V   Y   I     Y   L   F   M   Q   I   A   V   D   P
61/21                                      91/31
GTG GCT CTG GAT GGC AGT AGT CAG CCC ACA   GAG AAC GCT GAA AAA GAC GGA CTG TGC AAT
 V   A   L   D   G   S   S   Q   P   T     E   N   A   E   K   D   G   L   C   N
121/41                                     151/51
GCT TGT ACG TGG AGA CAG AAT ACA AAA TCC   TCC AGA ATA GAA GCC ATA AAA ATT CAA ATC
 A   C   T   W   R   Q   N   T   K   S     S   R   I   E   A   I   K   I   Q   I
181/61                                     211/71
CTC AGC AAA CTG CGC CTG GAA CAA GCA CCT   AAC ATT AGC AGG GAC GTT ATT AAG CAG CTT
 L   S   K   L   R   L   E   Q   A   P     N   I   S   R   D   V   I   K   Q   L
241/81                                     271/91
TTA CCC AAA GCT CCT CCA CTG CAG GAA CTG   ATT GAT CAG TAT GAT GTC CAG AGG GAC GAC
 L   P   K   A   P   P   L   Q   E   L     I   D   Q   Y   D   V   Q   R   D   D
301/101                                    331/111
AGT AGC GAT GGC TCT TTG GAA GAC GAT GAC   TAT CAT GCC ACA ACC GAG ACG ATT ATC ACA
 S   S   D   G   S   L   E   D   D   D     Y   H   A   T   T   E   T   I   I   T
361/121                                    391/131
ATG CCT ACG GAG TCT GAT TTT CTT GTA CAA   ATG GAG GGA AAA CCA AAA TGT TGC TTC TTT
 M   P   T   E   S   D   F   L   V   Q     M   E   G   K   P   K   C   C   F   F
421/141                                    451/151
AAG TTT AGC TCT AAA ATA CAA TAT AAC AAA   GTA GTA AAG GCA CAA TTA TGG ATA TAC TTG
 K   F   S   S   K   I   Q   Y   N   K     V   V   K   A   Q   L   W   I   Y   L
481/161                                    511/171
AGG CAA GTC CAA AAA CCT ACA ACG GTG TTT   GTG CAG ATC CTG AGA CTC ATT AAG CCC ATG
 R   Q   V   Q   K   P   T   T   V   F     V   Q   I   L   R   L   I   K   P   M
541/181                                    571/191
AAA GAC GGT ACA AGA TAT ACT GGA ATT CGA   TCT TTG AAA CTT GAC ATG AAC CCA GGC ACT
 K   D   G   T   R   Y   T   G   I   R     S   L   K   L   D   M   N   P   G   T
601/201                                    631/211
GGT ATC TGG CAG AGT ATT GAT GTG AAG ACA   GTG CTG CAA AAT TGG CTC AAA CAG CCT GAA
 G   I   W   Q   S   I   D   V   K   T     V   L   Q   N   W   L   K   Q   P   E
661/221                                    691/231
TCC AAT TTA GGC ATC GAA ATA AAA GCT TTT   GAT GAG ACT GGA CGA GAT CTT GCT GTC ACA
 S   N   L   G   I   E   I   K   A   F     D   E   T   G   R   D   L   A   V   T
721/241                                    751/251
TTC CCA GGA CCG GGT GAA GAT GGA TTG AAC   CCA TTT TTA GAG GTC AGA GTT ACA GAC ACA
 F   P   G   P   G   E   D   G   L   N     P   F   L   E   V   R   V   T   D   T
781/261                                    811/271
CCG AAA CGG TCC CGC AGA GAT TTT GGC CTT   GAC TGT GAT GAG CAC TCA ACG GAA TCC CGA
 P   K   R   S   R   R   D   F   G   L     D   C   D   E   H   S   T   E   S   R
841/281                                    871/291
TGT TGT CGC TAC CCG CTG ACA GTG GAT TTC   GAA GCT TTT GGA TGG GAC TGG ATT ATA GCA
 C   C   R   Y   P   L   T   V   D   F     E   A   F   G   W   D   W   I   I   A
901/301                                    931/311
CCT AAA AGA TAC AAA GCC AAT TAC TGC TCC   GGA GAA TGC GAA TTT GTG TTT CTA CAG AAA
 P   K   R   Y   K   A   N   Y   C   S     G   E   C   E   F   V   F   L   Q   K
961/321                                    991/331
TAC CCG CAC ACT CAC CTG GTA CAC CAA GCA   AAT CCC AGA GGC TCA GCA GGC CCT TGC TGC
 Y   P   H   T   H   L   V   H   Q   A     N   P   R   G   S   A   G   P   C   C
1021/341                                   1051/351
ACA CCC ACC AAG ATG TCC CCT ATA AAC ATG   CTG TAT TTC AAT GGA AAA GAA CAA ATA ATA
 T   P   T   K   M   S   P   I   N   M     L   Y   F   N   G   K   E   Q   I   I
1081/361                                   1111/371
TAT GGA AAG ATA CCA GCC ATG GTT GTA GAT   CGT TGC GGG TGC TCA TGA
 Y   G   K   I   P   A   M   V   V   D     R   C   G   C   S   *
```

Chicken GDF-8

FIG. 14C

```
1/1                                           31/11
ATG ATT CAA AAA CCG CAA ATG TAT GTT TAT   ATT TAC CTG TTT GTG CTG ATT GCT GCT GGC
 M   I   Q   K   P   Q   M   Y   V   Y    I   Y   L   F   V   L   I   A   A   G
61/21                                         91/31
CCA GTG GAT CTA AAT GAG GAC AGT GAG AGA   GAG GCG AAT GTG GAA AAA GAG GGG CTG TGT
 P   V   D   L   N   E   D   S   E   R    E   A   N   V   E   K   E   G   L   C
121/41                                        151/51
AAT GCG TGT GCG TGG AGA CAA AAC ACA AGG   TAC TCC AGA ATA GAA GCC ATA AAA ATT CAA
 N   A   C   A   W   R   Q   N   T   R    Y   S   R   I   E   A   I   K   I   Q
181/61                                        211/71
ATC CTC AGT AAA CTC CGC CTG GAA ACA GCG   CCT AAC ATC AGC AAA GAT GCT ATA AGA CAA
 I   L   S   K   L   R   L   E   T   A    P   N   I   S   K   D   A   I   R   Q
241/81                                        271/91
CTT CTG CCC AGA GCG CCT CCA CTC CGG GAA   CTG ATC GAT CAG TAC GAC GTC CAG AGG GAT
 L   L   P   R   A   P   P   L   R   E    L   I   D   Q   Y   D   V   Q   R   D
301/101                                       331/111
GAC AGC AGT GAC GGC TCT TTG GAA GAT GAC   GAT TAT CAC GCT ACC ACG GAA ACA ATC ATT
 D   S   S   D   G   S   L   E   D   D    D   Y   H   A   T   T   E   T   I   I
361/121                                       391/131
ACC ATG CCT ACC GAG TCT GAC TTT CTA ATG   CAA GCG GAT GGA AAG CCC AAA TGT TGC TTT
 T   M   P   T   E   S   D   F   L   M    Q   A   D   G   K   P   K   C   C   F
421/141                                       451/151
TTT AAA TTT AGC TCT AAA ATA CAG TAC AAC   AAA GTG GTA AAG GCC CAG CTG TGG ATA TAT
 F   K   F   S   S   K   I   Q   Y   N    K   V   V   K   A   Q   L   W   I   Y
481/161                                       511/171
CTG AGA GCC GTC AAG ACT CCT ACA ACA GTG   TTT GTG CAA ATC CTG AGA CTC ATC AAA CCC
 L   R   A   V   K   T   P   T   T   V    F   V   Q   I   L   R   L   I   K   P
541/181                                       571/191
ATG AAA GAC GGT ACA AGG TAT ACC GGA ATC   CGA TCT CTG AAA CTT GAC ATG AGC CCA GGC
 M   K   D   G   T   R   Y   T   G   I    R   S   L   K   L   D   M   S   P   G
601/201                                       631/211
ACT GGT ATT TGG CAG AGT ATT GAT GTG AAG   ACA GTG TTG CAA AAT TGG CTC AAA CAG CCT
 T   G   I   W   Q   S   I   D   V   K    T   V   L   Q   N   W   L   K   Q   P
661/221                                       691/231
GAA TCC AAC TTA GGC ATT GAA ATC AAA GCT   TTG GAT GAG AAT GGG CAT GAT CTT GCT GTA
 E   S   N   L   G   I   E   I   K   A    L   D   E   N   G   H   D   L   A   V
721/241                                       751/251
ACC TTC CCA GGA CCA GGA GAA GAT GGG CTG   AAT CCC TTT TTA GAA GTC AAA GTA ACA GAC
 T   F   P   G   P   G   E   D   G   L    N   P   F   L   E   V   K   V   T   D
781/261                                       811/271
ACA CCC AAG AGG TCC CGG AGA GAC TTT GGG   CTT GAC TGT GAT GAA CAC TCC ACG GAA TCG
 T   P   K   R   S   R   R   D   F   G    L   D   C   D   E   H   S   T   E   S
841/281                                       871/291
CGG TGC TGT CGC TAC CCC CTC ACG GTC GAT   TTC GAA GCC TTT GGA TGG GAC TGG ATT ATT
 R   C   C   R   Y   P   L   T   V   D    F   E   A   F   G   W   D   W   I   I
901/301                                       931/311
GCA CCC AAA AGA TAT AAG GCT AAT TAC TGC   TCT GGA GAG TGT GAA TTT GTG TTC TTA CAA
 A   P   K   R   Y   K   A   N   Y   C    S   G   E   C   E   F   V   F   L   Q
961/321                                       991/331
AAA TAT CCG CAT ACT CAT CTT GTG CAC CAA   GCA AAC CCC AGA GGC TCG GCA GGC CCT TGC
 K   Y   P   H   T   H   L   V   H   Q    A   N   P   R   G   S   A   G   P   C
1021/341                                      1051/351
TGC ACG CCA ACA AAA ATG TCT CCC ATT AAT   ATG CTA TAT TTT AAT GGC AAA GAA CAA ATA
 C   T   P   T   K   M   S   P   I   N    M   L   Y   F   N   G   K   E   Q   I
1081/361                                      1111/371
ATA TAT GGG AAA ATT CCA GCC ATG GTA GTA   GAC CGG TGT GGG TGC TCG TGA
 I   Y   G   K   I   P   A   M   V   V    D   R   C   G   C   S   *
```

Rat GDF-8

FIG. 14D

```
1/1                                          31/11
ATG CAA AAG CTA GCA GTC TAT GTT TAT ATT     TAC CTG TTC ATG CAG ATT TTA GTT CAT CCG
 M   Q   K   L   A   V   Y   V   Y   I       Y   L   F   M   Q   I   L   V   H   P
61/21                                        91/31
CTG GCT CTT GAT GGC AGT AGT CAG CCC ACA     GAG AAC GCT GAA AAA GAC GGA CTG TGC AAT
 V   A   L   D   G   S   S   Q   P   T       E   N   A   E   K   D   G   L   C   N
121/41                                       151/51
GCT TGC ACG TGG AGA CAG AAT ACT AAA TCC     TCC AGA ATA GAA GCC ATA AAA ATT CAA ATC
 A   C   T   W   R   Q   N   T   K   S       S   R   I   E   A   I   K   I   Q   I
181/61                                       211/71
CTC AGC AAA CTG CGC CTG GAA CAA GCA CCT     AAC ATT AGC AGG GAC GTT ATT AAA CAA CTT
 L   S   K   L   R   L   E   Q   A   P       N   I   S   R   D   V   I   K   Q   L
241/81                                       271/91
TTA CCC AAA GCT CCT CCG CTG CAG GAA CTG     ATT GAT CAG TAT GAC GTC CAG AGA GAC GAC
 L   P   K   A   P   P   L   Q   E   L       I   D   Q   Y   D   V   Q   R   D   D
301/101                                      331/111
AGT AGC GAT GGC TCT TTG GAA GAC GAT GAC     TAT CAT GCC ACA ACC GAA ACG ATT ATC ACA
 S   S   D   G   S   L   E   D   D   D       Y   H   A   T   T   E   T   I   I   T
361/121                                      391/131
ATG CCT ACG GAG TCT GAT TTT CTT GTA CAA     ATG GAG GGA AAA CCA AAA TGT TGC TTC TTT
 M   P   T   E   S   D   F   L   V   Q       M   E   G   K   P   K   C   C   F   F
421/141                                      451/151
AAG TTT AGC TCT AAA ATA CAA TAT AAC AAA     GTA GTA AAG GCA CAA TTA TGG ATA TAC TTG
 K   F   S   S   K   I   Q   Y   N   K       V   V   K   A   Q   L   W   I   Y   L
481/161                                      511/171
AGG CAA GTC CAA AAA CCT ACA ACG GTG TTT     GTC CAG ATC CTG AGA CTC ATT AAA CCC ATG
 R   Q   V   Q   K   P   T   T   V   F       V   Q   I   L   R   L   I   K   P   M
541/181                                      571/191
AAA GAC GGT ACA AGA TAT ACT GGA ATT CGA     TCT TTG AAA CTT GAC ATG AAC CCA GGC ACT
 K   D   G   T   R   Y   T   G   I   R       S   L   K   L   D   M   N   P   G   T
601/201                                      631/211
GGT ATC TGG CAG AGT ATT GAT GTG AAG ACA     GTG TTG CAA AAT TGG CTC AAA CAG CCT GAA
 G   I   W   Q   S   I   D   V   K   T       V   L   Q   N   W   L   K   Q   P   E
661/221                                      691/231
TCC AAT TTA GGC ATC GAA ATA AAA GCT TTT     GAT GAG AAT GGA CGA GAT CTT CCT GTA ACA
 S   N   L   G   I   E   I   K   A   F       D   E   N   G   R   D   L   P   V   T
721/241                                      751/251
TTC CCA GGA CCA GGT GAA GAT GGA CTG AAC     CCA TTT TTA GAG GTC AGA GTT ACA GAC ACA
 F   P   G   P   G   E   D   G   L   N       P   F   L   E   V   R   V   T   D   T
781/261                                      811/271
CCA AAA CGG TCC CGC AGA GAT TTT GGC CTT     GAC TGC GAC GAG CAC TCA ACG GAA TCT CGA
 P   K   R   S   R   R   D   F   G   L       D   C   D   E   H   S   T   E   S   R
841/281                                      871/291
TGT TGT CGC TAC CCG CTC ACA GTG GAT TTT     GAA GCT TTT GGA TGG GAC TGG ATT ATA GCA
 C   C   R   Y   P   L   T   V   D   F       E   A   F   G   W   D   W   I   I   A
901/301                                      931/311
CCT AAA AGA TAC AAA GCC AAT TAC TGC TCT     GGA GAA TGT GAA TTC GTA TTT CTA CAG AAA
 P   K   R   Y   K   A   N   Y   C   S       G   E   C   E   F   V   F   L   Q   K
961/321                                      991/331
TAC CCG CAC ACT CAC CTG GTA CAC CAA GCA     AAT CCA AGA GGC TCA GCA GGC CCT TGC TGC
 Y   P   H   T   H   L   V   H   Q   A       N   P   R   G   S   A   G   P   C   C
1021/341                                     1051/351
ACA CCC ACC AAG ATG TCC CCT ATA AAC ATG     CTC TAT TTC AAT GGA AAA GAA CAA ATA ATA
 T   P   T   K   M   S   P   I   N   M       L   Y   F   N   G   K   E   Q   I   I
1081/361                                     1111/371
TAT GGA AAG ATA CCA GCC ATG GTT GTA GAT     CGT TGC GGC TGC TCA TGA
 Y   G   K   I   P   A   M   V   V   D       R   C   G   C   S   *
```

Turkey GDF-8

FIG. 14E

```
1/1                                       31/11
ATG CAA AAA CTG CAA ATC TAT GTT TAT ATT   TAC CTG TTT ATG CTG ATT GTT GCT GGT CCC
 M   Q   K   L   Q   I   Y   V   Y   I    Y   L   F   M   L   I   V   A   G   P
61/21                                     91/31
GTG GAT CTG AAT GAG AAC AGC GAG CAA AAG   GAA AAT GTG GAA AAA GAG GGG CTG TGT AAT
 V   D   L   N   E   N   S   E   Q   K    E   N   V   E   K   E   G   L   C   N
121/41                                    151/51
GCA TGT ATG TGG AGA CAA AAC ACT AAA TCT   TCA AGA CTA GAA GCC ATA AAA ATT CAA ATC
 A   C   M   W   R   Q   N   T   K   S    S   R   L   E   A   I   K   I   Q   I
181/61                                    211/71
CTC AGT AAA CTT CGC CTG GAA ACA GCT CCT   AAC ATT AGC AAA GAT GCT ATA AGA CAA CTT
 L   S   K   L   R   L   E   T   A   P    N   I   S   K   D   A   I   R   Q   L
241/81                                    271/91
TTG CCC AAA GCT CCT CCA CTC CGG GAA CTG   ATT GAT CAG TAC GAT GTC CAG AGA GAT GAC
 L   P   K   A   P   P   L   R   E   L    I   D   Q   Y   D   V   Q   R   D   D
301/101                                   331/111
AGC AGT GAT GGC TCC TTG GAA GAT GAT GAT   TAT CAC GCT ACG ACG GAA ACG ATC ATT ACC
 S   S   D   G   S   L   E   D   D   D    Y   H   A   T   T   E   T   I   I   T
361/121                                   391/131
ATG CCT ACA GAG TCT GAT CTT CTA ATG CAA   GTG GAA GGA AAA CCC AAA TGC TGC TTC TTT
 M   P   T   E   S   D   L   L   M   Q    V   E   G   K   P   K   C   C   F   F
421/141                                   451/151
AAA TTT AGC TCT AAA ATA CAA TAC AAT AAA   GTA GTA AAG GCC CAA CTG TGG ATA TAT CTG
 K   F   S   S   K   I   Q   Y   N   K    V   V   K   A   Q   L   W   I   Y   L
481/161                                   511/171
AGA CCC GTC AAG ACT CCT ACA ACA GTG TTT   GTG CAA ATC CTG AGA CTC ATC AAA CCC ATG
 R   P   V   K   T   P   T   T   V   F    V   Q   I   L   R   L   I   K   P   M
541/181                                   571/191
AAA GAC GGT ACA AGG TAT ACT GGA ATC CGA   TCT CTG AAA CTT GAC ATG AAC CCA GGC ACT
 K   D   G   T   R   Y   T   G   I   R    S   L   K   L   D   M   N   P   G   T
601/201                                   631/211
GGT ATT TGG CAG AGC ATT GAT GTG AAG ACA   GTG TTG CAA AAT TGG CTC AAA CAA CCT GAA
 G   I   W   Q   S   I   D   V   K   T    V   L   Q   N   W   L   K   Q   P   E
661/221                                   691/231
TCC AAC TTA GGC ATT GAA ATC AAA GCT TTA   GAT GAG AAT GGT CAT GAT CTT GCT GTA ACC
 S   N   L   G   I   E   I   K   A   L    D   E   N   G   H   D   L   A   V   T
721/241                                   751/251
TTC CCA GGA CCA GGA GAA GAT GGG CTG AAT   CCC TTT TTA GAA GTC AAG GTA ACA GAC ACA
 F   P   G   P   G   E   D   G   L   N    P   F   L   E   V   K   V   T   D   T
781/261                                   811/271
CCA AAA AGA TCC AGG AGA GAT TTT GGA CTC   GAC TGT GAT GAG CAC TCA ACA GAA TCT CGA
 P   K   R   S   R   R   D   F   G   L    D   C   D   E   H   S   T   E   S   R
841/281                                   871/291
TGC TGT CGT TAC CCT CTA ACT GTG GAT TTT   GAA GCT TTT GGA TGG GAC TGG ATT ATT GCA
 C   C   R   Y   P   L   T   V   D   F    E   A   F   G   W   D   W   I   I   A
901/301                                   931/311
CCC AAA AGA TAT AAG GCC AAT TAC TGC TCT   GGA GAG TGT GAA TTT GTA TTT TTA CAA AAA
 P   K   R   Y   K   A   N   Y   C   S    G   E   C   E   F   V   F   L   Q   K
961/321                                   991/331
TAC CCT CAC ACT CAT CTT GTG CAC CAA GCA   AAC CCC AGA GGT TCA GCA GGC CCC TGC TGT
 Y   P   H   T   H   L   V   H   Q   A    N   P   R   G   S   A   G   P   C   C
1021/341                                  1051/351
ACT CCC ACA AAG ATG TCT CCA ATC AAT ATG   CTA TAT TTT AAT GGC AAA GAA CAA ATA ATA
 T   P   T   K   M   S   P   I   N   M    L   Y   F   N   G   K   E   Q   I   I
1081/361                                  1111/371
TAT GGG AAA ATT CCA GCC ATG GTA GTA GAT   CGC TGT GGG TGC TCA TGA
 Y   G   K   I   P   A   M   V   V   D    R   C   G   C   S   *
```

Porcine GDF-8

FIG. 14F

```
1/1                                       31/11
ATG CAA AAA CTG CAA ATC TTT GTT TAT ATT   TAC CTA TTT ATG CTG CTT GTT GCT GGC CCA
 M   Q   K   L   Q   I   F   V   Y   I    Y   L   F   M   L   L   V   A   G   P
61/21                                     91/31
GTG GAT CTG AAT GAG AAC AGC GAG CAG AAG   GAA AAT GTG GAA AAA AAG GGG CTG TGT AAT
 V   D   L   N   E   N   S   E   Q   K    E   N   V   E   K   K   G   L   C   N
121/41                                    151/51
GCA TGC TTG TGG AGA CAA AAC AAT AAA TCC   TCA AGA CTA GAA GCC ATA AAA ATC CAA ATC
 A   C   L   W   R   Q   N   N   K   S    S   R   L   E   A   I   K   I   Q   I
181/61                                    211/71
CTC AGT AAG CTT CGC CTG GAA ACA GCT CCT   AAC ATC AGC AAA GAT GCT ATA AGA CAA CTT
 L   S   K   L   R   L   E   T   A   P    N   I   S   K   D   A   I   R   Q   L
241/81                                    271/91
TTG CCC AAG GCT CCT CCA CTC CGG GAA CTG   ATT GAT CAG TAC GAT GTC CAG AGA GAT GAC
 L   P   K   A   P   P   L   R   E   L    I   D   Q   Y   D   V   Q   R   D   D
301/101                                   331/111
AGC AGC GAC GGC TCC TTG GAA GAC GAT GAC   TAC CAC GTT ACG ACG GAA ACG GTC ATT ACC
 S   S   D   G   S   L   E   D   D   D    Y   H   V   T   T   E   T   V   I   T
361/121                                   391/131
ATG CCC ACG GAG TCT GAT CTT CTA GCA GAA   GTG CAA GAA AAA CCC AAA TGT TGC TTC TTT
 M   P   T   E   S   D   L   L   A   E    V   Q   E   K   P   K   C   C   F   F
421/141                                   451/151
AAA TTT AGC TCT AAG ATA CAA CAC AAT AAA   GTA GTA AAG GCC CAA CTG TGG ATA TAT CTG
 K   F   S   S   K   I   Q   H   N   K    V   V   K   A   Q   L   W   I   Y   L
481/161                                   511/171
AGA CCT GTC AAG ACT CCT ACA ACA GTG TTT   GTG CAA ATC CTG AGA CTC ATC AAA CCC ATG
 R   P   V   K   T   P   T   T   V   F    V   Q   I   L   R   L   I   K   P   M
541/181                                   571/191
AAA GAC GGT ACA AGG TAT ACT GGA ATC CGA   TCT CTG AAA CTT GAC ATG AAC CCA GGC ACT
 K   D   G   T   R   Y   T   G   I   R    S   L   K   L   D   M   N   P   G   T
601/201                                   631/211
GGT ATT TGG CAG AGC ATT GAT GTG AAG ACA   GTG TTG CAA AAC TGG CTC AAA CAA CCT GAA
 G   I   W   Q   S   I   D   V   K   T    V   L   Q   N   W   L   K   Q   P   E
661/221                                   691/231
TCC AAC TTA GGC ATT GAA ATC AAA GCT TTA   GAT GAG AAT GGT CAT GAT CTT GCT GTA ACC
 S   N   L   G   I   E   I   K   A   L    D   E   N   G   H   D   L   A   V   T
721/241                                   751/251
TTC CCA GAA CCA GGA GAA GAA GGA CTG AAT   CCT TTT TTA GAA GTC AAG GTA ACA GAC ACA
 F   P   E   P   G   E   E   G   L   N    P   F   L   E   V   K   V   T   D   T
781/261                                   811/271
CCA AAA AGA TCT AGG AGA GAT TTT GGG CTT   GAT TGT GAT GAG CAC TCC ACA GAA TCT CGA
 P   K   R   S   R   R   D   F   G   L    D   C   D   E   H   S   T   E   S   R
841/281                                   871/291
TGC TGT CGT TAC CCT CTA ACT GTG GAT TTT   GAA GCT TTT GGA TGG GAT TGG ATT ATT GCA
 C   C   R   Y   P   L   T   V   D   F    E   A   F   G   W   D   W   I   I   A
901/301                                   931/311
CCT AAA AGA TAT AAG GCC AAT TAC TGC TCT   GGA GAA TGT GAA TTT TTA TTT TTG CAA AAG
 P   K   R   Y   K   A   N   Y   C   S    G   E   C   E   F   L   F   L   Q   K
961/321                                   991/331
TAT CCT CAT ACC CAT CTT GTG CAC CAA GCA   AAC CCC AAA GGT TCA GCC GGC CCT TGC TGT
 Y   P   H   T   H   L   V   H   Q   A    N   P   K   G   S   A   G   P   C   C
1021/341                                  1051/351
ACT CCT ACA AAG ATG TCT CCA ATT AAT ATG   CTA TAT TTT AAT GGC AAA GAA CAA ATA ATA
 T   P   T   K   M   S   P   I   N   M    L   Y   F   N   G   K   E   Q   I   I
1081/361                                  1111/371
TAT GGG AAG ATT CCA GGC ATG GTA GTA GAT   CGC TGT GGG TGC TCA TGA
 Y   G   K   I   P   G   M   V   V   D    R   C   G   C   S   *
```

Ovine GDF-8

FIG. 14G

```
M M Q K L Q M Y V Y I Y L F M L I A A G P V D L N E G S E R E E N V E K E G L C  murine
M I Q K P Q M Y V Y I Y L F V L I A A G P V D L N E D S E R E A N V E K E G L C  rat
M - Q K L Q L C V Y I Y L F M L I V A G P V D L N E N S E Q K E N V E K E G L C  human
M - Q K L Q L C V Y I Y L F M L I V A G P V D L N E N S E Q K E N V E K E G L C  baboon
M - Q K L Q I Y V Y I Y L F M L I V A G P V D L N E N S E Q K E N V E K E G L C  porcine
M - Q K L Q I F V Y I Y L F M L L V A G P V D L N E N S E Q K E N V E K K G L C  ovine
M - Q K L Q I S V Y I Y L F M L I V A G P V D L N E N S E Q K E N V E K E G L C  bovine
M - Q K L A V Y V Y I Y L F M Q I A V D P V A L D G S S Q P T E N A E K D G L C  chicken
M - Q K L A V Y V Y I Y L F M Q T L V H P V A L D G S S Q P T E N A E K D G L C  turkey N A C A W R Q N T R Y S R I E A I K I Q I L S K L R L E T A P N I S K D A I R Q  murine
N A C A W R Q N T R Y S R I E A I K I Q I L S K L R L E T A P N I S K D A I R Q  rat
N A C T W R Q N T K S S R I E A I K I Q I L S K L R L E T A P N I S K D V I R Q  human
N A C T W R Q N T K S S R I E A I K I Q I L S K L R L E T A P N I S K D A I R Q  baboon
N A C M W R Q N T K S S R L E A I K I Q I L S K L R L E T A P N I S K D A I R Q  porcine
N A C L W R Q N N K S S R L E A I K I Q I L S K L R L E T A P N I S K D A I R Q  ovine
N A C L W R E N T S S R L E A I K I Q I L S K L R L E T A P N I S K D A I R Q  bovine
N A C T W R Q N T K S S R I E A I K I Q I L S K L R L E Q A P N I S R D V I K Q  chicken
N A C T W R Q N T K S S R I E A I K I Q I L S K L R L E Q A P N I S R D V I K Q  turkey L L P R A P P L R E L I D Q Y D V Q R D D S S D G S L E D D D Y H A T T E T I I  murine
L L P R A P P L R E L I D Q Y D V Q R D D S S D G S L E D D D Y H A T T E T I I  rat
L L P K A P P L R E L I D Q Y D V Q R D D S S D G S L E D D D Y H A T T E T I I  human
L L P K A P P L R E L I D Q Y D V Q R D D S S D G S L E D D D Y H A T T E T I I  baboon
L L P K A P P L R E L I D Q Y D V Q R D D S S D G S L E D D D Y H A T T E T I I  porcine
L L P K A P P L R E L I D Q Y D V Q R D D S S D G S L E D D D Y H V T T E T V I  ovine
L L P K A P P L L E L I D Q F D V Q R D A S S D G S L E D D D Y H A R T E T V I  bovine
L L P K A P P L Q E L I D Q Y D V Q R D D S S D G S L E D D D Y H A T T E T I I  chicken
L L P K A P P L Q E L I D Q Y D V Q R D D S S D G S L E D D D Y H A T T E T I I  turkey T M P T E S D F L M Q A D G K P K C C F F K F S S K I Q Y N K V V K A Q L W I Y  murine
T M P T E S D F L M Q A D G K P K C C F F K F S S K I Q Y N K V V K A Q L W I Y  rat
T M P T E S D F L M Q V D G K P K C C F F K F S S K I Q Y N K V V K A Q L W I Y  human
T M P T E S D F L M Q V D G K P K C C F F K F S S K I Q Y N K V V K A Q L W I Y  baboon
T M P T E S D L L M Q V E G K P K C C F F K F S S K I Q Y N K V V K A Q L W I Y  porcine
T M P T E S D L L A E V Q E K P K C C F F K F S S K I Q H N K V V K A Q L W I Y  ovine
T M P T E S D L L T Q V E G K P K C C F F K F S S K I Q Y N K L V K A Q L W I Y  bovine
T M P T E S D F L V Q M E G K P K C C F F K F S S K I Q Y N K V V K A Q L W I Y  chicken
T M P T E S D F L V Q M E G K P K C C F F K F S S K I Q Y N K V V K A Q L W I Y  turkey L R P V K T P T T V F V Q I L R L I K P M K D G T R Y T G I R S L K L D M S P G  murine
L R A V K T P T T V F V Q I L R L I K P M K D G T R Y T G I R S L K L D M S P G  rat
L R P V E T P T T V F V Q I L R L I K P M K D G T R Y T G I R S L K L D M N P G  human
L R P V E T P T T V F V Q I L R L I K P M K D G T R Y T G I R S L K L D M N P G  baboon
L R P V K T P T T V F V Q I L R L I K P M K D G T R Y T G I R S L K L D M N P G  porcine
L R P V K T P A T V F V Q I L R L I K P M K D G T R Y T G I R S L K L D M N P G  ovine
L R P V K T P A T V F V Q I L R L I K P M K D G T R Y T G I R S L K L D M N P G  bovine
L R Q V Q K P T T V F V Q I L R L I K P M K D G T R Y T G I R S L K L D M N P G  chicken
L R Q V Q K P T T V F V Q I L R L I K P M K D G T R Y T G I R S L K L D M N P G  turkey T G I W Q S I D V K T V L Q N W L K Q P E S N L G I E I K A L D E N G H D L A V  murine
T G I W Q S I D V K T V L Q N W L K Q P E S N L G I E I K A L D E N G H D L A V  rat
T G I W Q S I D V K T V L Q N W L K Q P E S N L G I E I K A L D E N G H D L A V  human
T G I W Q S I D V K T V L Q N W L K Q P E S N L G I E I K A L D E N G H D L A V  baboon
T G I W Q S I D V K T V L Q N W L K Q P E S N L G I E I K A L D E N G H D L A V  porcine
T G I W Q S I D V K T V L Q N W L K Q P E S N L G I E I K A L D E N G H D L A V  ovine
T G I W Q S I D V K T V L Q N W L K Q P E S N L G I E I K A L D E N G H D L A V  bovine
T G I W Q S I D V K T V L Q N W L K Q P E S N L G I E I K A F D E T G R D L A V  chicken
T G I W Q S I D V K T V L Q N W L K Q P E S N L G I E I K A F D E N G R D L A V  turkey
```

Decoration 'Decoration #1': Shade (with solid black) residues that match the Consensus exactly.

METHODS OF DETECTING GROWTH DIFFERENTIATION FACTOR-8

This application is a continuation of U.S. Ser. No. 09/019,070, filed Feb. 5, 1998 (now abandoned), which is a continuation-in-part (CIP) of U.S. Ser. No. 08/862,445, filed May 23, 1997 (now abandoned), which is a CIP of U.S. application Ser. No. 08/847,910, filed Apr. 28, 1997 (now abandoned), which is a CIP of U.S. Ser. No. 08/795,071, filed Feb. 5, 1997 (now U.S. Pat. No. 5,994,618), which is a CIP of U.S. Ser. No. 08/525,596, filed Oct. 25, 1995 (now U.S. Pat. No. 5,827,733), which is a 371 application of PCT/US94/03019 filed on Mar. 18, 1994, and said U.S. patent Ser. No. 09/019,070 which is a CIP of U.S. Ser. No. 08/033,923 filed on Mar. 19, 1993 (now abandoned).

BACKGROUND OF THE INVENTION

1. Field of the Invention

The invention relates generally to growth factors and specifically to a new member of the transforming growth factor beta (TGF-β) superfamily, which is denoted, growth differentiation factor-8 (GDF-8) and methods of use for modulating muscle cell and adipose tissue growth.

2. Description of Related Art

The transforming growth factor β(TGF-β) superfamily encompasses a group of structurally related proteins which affect a wide range of differentiation processes during embryonic development. The family includes, Mullerian inhibiting substance (MIS), which is required for normal male sex development (Behringer, et al., *Nature*, 345:167, 1990), Drosophila decapentaplegic (DPP) gene product, which is required for dorsal-ventral axis formation and morphogenesis of the imaginal disks (Padgett, et al., *Nature*, 2:81–84, 1987), the Xenopus Vg-1 gene product, which localizes to the vegetal pole of eggs ((Weeks, et al., *Cell*, 51:861–867, 1987), the activins (Mason, et al., *Biochem, Biophys. Res. Commun.*, 135:957–964, 1986), which can induce the formation of mesoderm and anterior structures in Xenopus embryos (Thomsen, et al., *Cell*, 63:485, 1990), and the bone morphogenetic proteins (BMPs, osteogenin, OP-1) which can induce de novo cartilage and bone formation (Sampath, et al., *J. Biol. Chem.*, 265:13198, 1990). The TGF-β can influence a variety of differentiation processes, including adipogenesis, myogenesis, chondrogenesis, hematopoiesis, and epithelial cell differentiation (for review, see Massague, *Cell* 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray, A. et al., *Science*, 247:1328, 1990). Additional studies by Hammonds, et al., (*Molec. Endocrinol.* 5:149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling, et al., *Nature*, 31:779, 1986) and the TGF-βs (Cheifetz, et al., *Cell*, 48:409, 1987), heterodimers have also been detected, and these appear to have different biological properties than the respective homodimers.

In addition it is desirable to produce livestock and game animals, such as cows, sheep, pigs, chicken and turkey, fish which are relatively high in musculature and protein, and low in fat content. Many drug and diet regimens exist which may help increase muscle and protein content and lower undesirably high fat and/or cholesterol levels, but such treatment is generally administered after the fact, and is begun only after significant damage has occurred to the vasculature. Accordingly, it would be desirable to produce animals which are genetically predisposed to having higher muscle content, without any ancillary increase in fat levels.

The food industry has put much effort into increasing the amount of muscle and protein in foodstuffs. This quest is relatively simple in the manufacture of synthetic foodstuffs, but has been met with limited success in the preparation of animal foodstuffs. Attempts have been made, for example, to lower cholesterol levels in beef and poultry products by including cholesterol-lowering drugs in animal feed (see e.g. Elkin and Rogler, J. Agric. Food Chem. 1990, 38, 1635–1641). However, there remains a need for more effective methods of increasing muscle and reducing fat and cholesterol levels in animal food products.

SUMMARY OF THE INVENTION

The present invention provides a cell growth and differentiation factor, GDF-8, a polynucleotide sequence which encodes the factor, and antibodies which are immunoreactive with the factor. This factor appears to relate to various cell proliferative disorders, especially those involving muscle, nerve, and adipose tissue.

In one embodiment, the invention provides a method for detecting a cell proliferative disorder of muscle, nerve, or fat origin and which is associated with GDF-8. In another embodiment, the invention provides a method for treating a cell proliferative disorder by suppressing or enhancing GDF-8 activity.

In another embodiment, the subject invention provides non-human transgenic animals which are useful as a source of food products with high muscle and protein content, and reduced fat and cholesterol content. The animals have been altered chromosomally in their germ cells and somatic cells so that the production of GDF-8 is produced in reduced amounts, or is completely disrupted, resulting in animals with decreased levels of GDF-8 in their system and higher than normal levels of muscle tissue, preferably without increased fat and/or cholesterol levels. Accordingly, the present invention also includes food products provided by the animals. Such food products have increased nutritional value because of the increase in muscle tissue. The transgenic non-human animals of the invention include bovine, porcine, ovine and avian animals, for example.

The subject invention also provides a method of producing animal food products having increased muscle content. The method includes modifying the genetic makeup of the germ cells of a pronuclear embryo of the animal, implanting the embryo into the oviduct of a pseudopregnant female thereby allowing the embryo to mature to full term progeny, testing the progeny for presence of the transgene to identify transgene-positive progeny, cross-breeding transgene-positive progeny to obtain further transgene-positive progeny and processing the progeny to obtain foodstuff. The modification of the germ cell comprises altering the genetic composition so as to disrupt or reduce the expression of the naturally occurring gene encoding for production of GDF-8 protein. In a particular embodiment, the transgene comprises antisense polynucleotide sequences to the GDF-8 protein. Alternatively, the transgene may comprise a non-functional sequence which replaces or intervenes in the native GDF-8 gene.

The subject invention also provides a method of producing avian food products having improved muscle content. The method includes modifying the genetic makeup of the germ cells of a pronuclear embryo of the avian animal, implanting the embryo into the oviduct of a pseudopregnant female into an embryo of a chicken, culturing the embryo under conditions whereby progeny are hatched, testing the progeny for presence of the genetic alteration to identify transgene-positive progeny, cross-breeding transgene-positive progeny and processing the progeny to obtain foodstuff.

The invention also provides a method for treating a muscle or adipose tissue disorder in a subject. The method includes administering a therapeutically effective amount of a GDF-8 agent to the subject, thereby inhibiting abnormal growth of muscle or adipose tissue. The GDF-8 agent may include an antibody, a GDF-8 antisense molecule or a dominant negative polypeptide, for example. In one aspect, a method for inhibiting the growth regulating actions of GDF-8 by contacting an anti-GDF-8 monoclonal antibody, a GDF-8 antisense molecule or a dominant negative polypeptide (or polynucleotide encoding a dominant negative polypeptide) with fetal or adult muscle cells or progenitor cells is included. These agents can be administered to a patient suffering from a disorder such as muscle wasting disease, neuromuscular disorder, muscle atrophy, obesity or other adipocyte cell disorders, and aging, for example.

The invention also provides a method for a method for identifying a compound that affects GDF-8 activity or gene expression including incubating the compound with GDF-8 polypeptide, or with a recombinant cell expressing GDF-8 under conditions sufficient to allow the compounds to interact and determining the effect of the compound on GDF-8 activity or expression.

BRIEF DESCRIPTION OF THE DRAWINGS

FIG. 1a is a Northern blot showing expression of GDF-8 mRNA in adult tissues. The probe was a partial murine GDF-8 clone.

FIGS. 2a to 2d show partial nucleotide and predicted amino acid sequences of murine GDF-8 (FIG. 2a; SEQ ID NOS:5 and 6, respectively), human GDF-8 (FIG. 2b; SEQ ID NOS: 7 and 8, respectively), rat GDF-8 (FIG. 2c; SEQ ID NOS: 32 and 33, respectively) and chicken GDF-8 (FIG. 2d; SEQ ID NOS: 34 and 35, respectively). The putative dibasic processing sites in the murine sequence are boxed.

FIG. 3a shows the alignment of the C-terminal sequences of GDF-8 with other members of the TGF-β superfamily (SEQ ID NOS: 12 and 36–49). The conserved cysteine residues are boxed. Dashes denote gaps introduced in order to maximize alignment.

FIG. 3b shows the alignment of the C-terminal sequences of GDF-8 from human (SEQ ID NO: 14), murine (SEQ ID NO: 12), rat (SEQ ID NO: 33) and chicken (SEQ ID NO: 35) sequences.

FIG. 4 shows amino acid homologies among different members of the TGF superfamily. Numbers represent percent amino acid identities between each pair calculated from the first conserved cysteine to the C-terminus. Boxes represent homologies among highly-related members within particular subgroups.

FIGS. 5a to 5d show the sequence of GDF-8. Nucleotide and amino acid sequences of murine (FIG. 5a and 5b; GenBank accession number U84005; SEQ ID NOS:11 and 12, respectively) and human (FIG. 5c and 5d; SEQ ID NOS:13 and 14, respectively) GDF-8 cDNA clones are shown. Numbers indicate nucleotide position relative to the 5' end. Consensus N-linked glycosylation signals are shaded. The putative RXXR (SEQ ID NO: 50) proteolytic cleavage sites are boxed.

FIG. 7 shows a comparison of murine and human GDF-8 amino acid sequences SEQ ID NOS: 12 and 14, respectively). The predicted murine sequence is shown in the top lines and the predicted human sequence is shown in the bottom lines. Numbers indicate amino acid position relative to the N-terminus. Identities between the two sequences are denoted by a vertical line.

FIGS. 10a and 10b show the expression of GDF-8 mRNA. Poly A-selected RNA (5 μg each) prepared from adult tissues (FIG. 10a) or placentas end embryos (FIG. 10b) at the indicated days of gestation was electrophoresed on formaldehyde gels, blotted, and probed with full length murine GDF-8.

FIG. 11 shows chromosomal mapping of human GDF-8. DNA samples prepared from human/rodent somatic cell hybrid lines were subjected to PCR, electrophoresed on agarose gels, blotted, and probed. The human chromosome contained in each of the hybrid cell lines is identified at the top of each of the first 24 lanes (1–22, X, and Y). In the lanes designated M, CHO, and H, the starting DNA template was total genomic DNA from mouse, hamster, and human sources, respectively. In the lane marked B1, no template DNA was used. Numbers at left indicate the mobilities of DNA standards.

FIG. 13a shows the smallest cross-sectional fiber widths measured for wild type (n=1761) and mutant (n=1052) tibialis cranial. FIG. 13b shows wild type (n=900) and mutant (n=900) gastrocnemius muscles, and fiber sizes were plotted as a percent of total fiber number. Standard deviations were 9 and 10 μm, respectively, for wild type and mutant tibialis cranial is and 11 and 9 μm, respectively, for wild type and mutant gastrocnemius muscles. Legend: o-o, wild type;_-_, mutant.

FIG. 14a shows the nucleotide and deduced amino acid sequence for baboon GDF-8 (SEQ ID NOS:18 and 19, respectively).

FIG. 14b shows the nucleotide and deduced amino acid sequence for bovine GDF-8 (SEQ ID NOS:20 and 21, respectively).

FIG. 14c shows the nucleotide and deduced amino acid sequence for chicken GDF-8 (SEQ ID NOS:22 and 23, respectively).

FIG. 14d shows the nucleotide and deduced amino acid sequence for rat GDF-8 (SEQ ID NOS:24 and 25, respectively).

FIG. 14e shows the nucleotide and deduced amino acid sequence for turkey GDF-8 (SEQ ID NOS:26 and 27, respectively).

FIG. 14f shows the nucleotide and deduced amino acid sequence for porcine GDF-8 (SEQ ID NOS:28 and 29, respectively).

FIG. 14g shows the nucleotide and deduced amino acid sequence for ovine GDF-8 (SEQ ID NOS:30 and 31, respectively).

FIGS. 15a and 15b show an alignment between murine, rat, human, porcine, ovine, baboon, bovine, chicken, and turkey GDF-8 amino acid sequences (SEQ ID NOS:12, 25, 14, 29, 31, 19, 21, 23 and 27, respectively).

DETAILED DESCRIPTION OF THE INVENTION

Figure 1B:
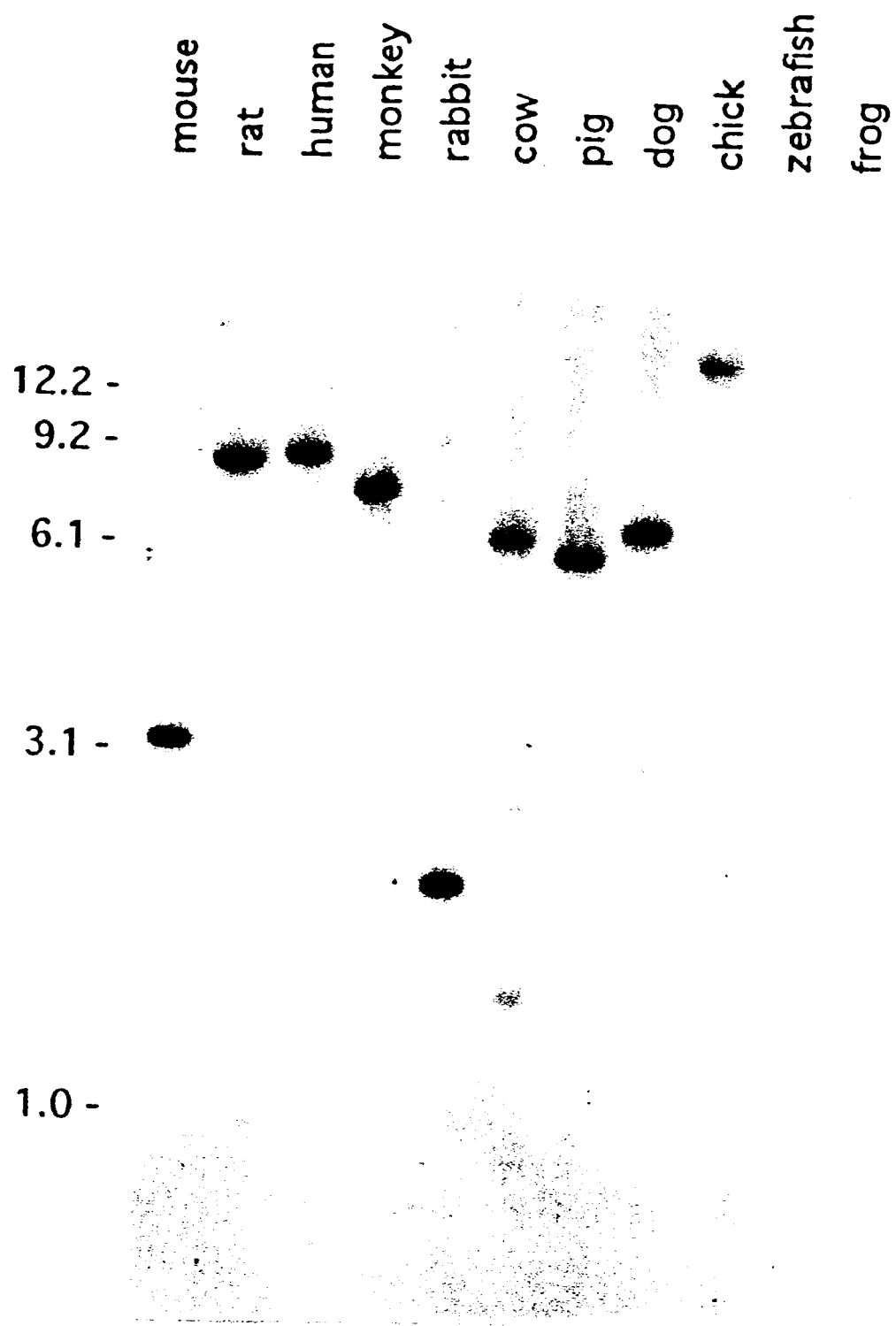
FIG. 1b is a Southern blot showing GDF-8 genomic sequences identified in mouse, rat, human, monkey, rabbit, cow, pig, dog and chicken.

The present invention provides a growth and differentiation factor, GDF-8 and a polynucleotide sequence encoding GDF-8. GDF-8 is expressed at highest levels in muscle and at lower levels in adipose tissue.

The animals contemplated for use in the practice of the subject invention are those animals generally regarded as useful for the processing of food stuffs, i.e. avian such as meat bred and egg laying chicken and turkey, ovine such as lamb, bovine such as beef cattle and milk cows, piscine and porcine. For purposes of the subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene integrated into the chromosomes of somatic cells.

The TGF-β superfamily consists of multifunctional polypeptides that control proliferation, differentiation, and other functions in many cell types. Many of the peptides have regulatory, both positive and negative, effects on other peptide growth factors. The structural homology between the GDF-8 protein of this invention and the members of the TGF-β family, indicates that GDF-8 is a new member of the family of growth and differentiation factors. Based on the known activities of many of the other members, it can be expected that GDF-8 will also possess biological activities that will make it useful as a diagnostic and therapeutic reagent.

In particular, certain members of this superfamily have expression patterns or possess activities that relate to the function of the nervous system. For example, the inhibins and activins have been shown to be expressed in the brain (Meunier, et al., *Proc. Natl. Acad. Sci., USA*, 85:247, 1988; Sawchenko, et al., *Nature*, 334:615, 1988), and activin has been shown to be capable of functioning as a nerve cell survival molecule (Schubert, et al., *Nature*, 344:868, 1990). Another family member, namely, GDF-1, is nervous system-specific in its expression pattern (Lee, S. J., *Proc. Natl. Acad Sci., USA*, 8:4250, 1991), and certain other family members, such as Vgr-1 (Lyons, et al., *Proc. Natl. Acad. Sci., USA*, 86:4554, 1989; Jones, et al., *Development*, 111:531, 1991), OP-1 (Ozkaynak, et al., *J. Biol. Chem.*, 267:25220, 1992), and BMP-4 (Jones, et al., *Development*, 111:531, 1991), are also known to be expressed in the nervous system. Because it is known that skeletal muscle produces a factor or factors that promote the survival of motor neurons (Brown, *Trends Neurosci.*, 7:10, 1984), the expression of GDF-8 in muscle suggests that one activity of GDF-8 may be as a trophic factor for neurons. In this regard, GDF-8 may have applications in the treatment of neurodegenerative diseases, such as amyotrophic lateral sclerosis or muscular dystrophy, or in maintaining cells or tissues in culture prior to transplantation.

GDF-8 may also have applications in treating disease processes involving muscle, such as in musculodegenerative diseases or in tissue repair due to trauma. In this regard, many other members of the TGF-β family are also important mediators of tissue repair. TGF-β has been shown to have marked effects on the formation of collagen and to cause a striking angiogenic response in the newborn mouse (Roberts, et al., *Proc. Natl. Acad Sci., USA* 83:4167, 1986). TGF-β has also been shown to inhibit the differentiation of myoblasts in culture (Massague, et al., *Proc. Natl. Acad. Sci., USA* 83:8206, 1986). Moreover, because myoblast cells may be used as a vehicle for delivering genes to muscle for gene therapy, the properties of GDF-8 could be exploited for maintaining cells prior to transplantation or for enhancing the efficiency of the fusion.

The expression of GDF-8 in adipose tissue also raises the possibility of applications for GDF-8 in the treatment of obesity or of disorders related to abnormal proliferation of adipocytes. In this regard, TGF-β has been shown to be a potent inhibitor of adipocyte differentiation in vitro (Ignotz and Massague, *Proc. Natl. Acad. Sci., USA* 82:8530, 1985).

Polypeptides, Polynucleotides, Vectors and Host Cells

The invention provides substantially pure GDF-8 polypeptide and isolated polynucleotides that encode GDF-8. The term "substantially pure" as used herein refers to GDF-8 which is substantially free of other proteins, lipids, carbohydrates or other materials with which it is naturally associated. One skilled in the art can purify GDF-8 using standard techniques for protein purification. The substantially pure polypeptide will yield a single major band on a non-reducing polyacrylamide gel. The purity of the GDF-8 polypeptide can also be determined by amino-terminal amino acid sequence analysis. GDF-8 polypeptide includes functional fragments of the polypeptide, as long as the activity of GDF-8 remains. Smaller peptides containing the biological activity of GDF-8 are included in the invention.

The invention provides polynucleotides encoding the GDF-8 protein. These polynucleotides include DNA, cDNA and RNA sequences which encode GDF-8. It is understood that all polynucleotides encoding all or a portion of GDF-8 are also included herein, as long as they encode a polypeptide with GDF-8 activity. Such polynucleotides include naturally occurring, synthetic, and intentionally manipulated polynucleotides. For example, GDF-8 polynucleotide may be subjected to site-directed mutagenesis. The polynucleotide sequence for GDF8 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-8 polypeptide encoded by the nucleotide sequence is functionally unchanged.

Specifically disclosed herein is a genomic DNA sequence containing a portion of the GDF-8 gene. The sequence contains an open reading frame corresponding to the predicted C-terminal region of the GDF-8 precursor protein. The encoded polypeptide is predicted to contain two potential proteolytic processing sites (KR and RR). Cleavage of the precursor at the downstream site would generate a mature biologically active C-terminal fragment of 109 and 103 amino acids for murine and human species, respectively, with a predicted molecular weight of approximately 12,400. Also disclosed are full length murine and human GDF-8 cDNA sequences. The murine pre-pro-GDF-8 protein is 376 amino acids in length, which is encoded by a 2676 base pair nucleotide sequence, beginning at nucleotide 104 and extending to a TGA stop codon at nucleotide 1232. The human GDF-8 protein is 375 amino acids and is encoded by a 2743 base pair sequence, with the open reading frame beginning at nucleotide 59 and extending to nucleotide 1184. GDF-8 is also capable of forming dimers, or heterodimers, with an expected molecular weight of approximately 23–30 kD (see Example 4). For example, GDF-8 may form heterodimers with other family members, such as GDF-11.

Figure 3A:
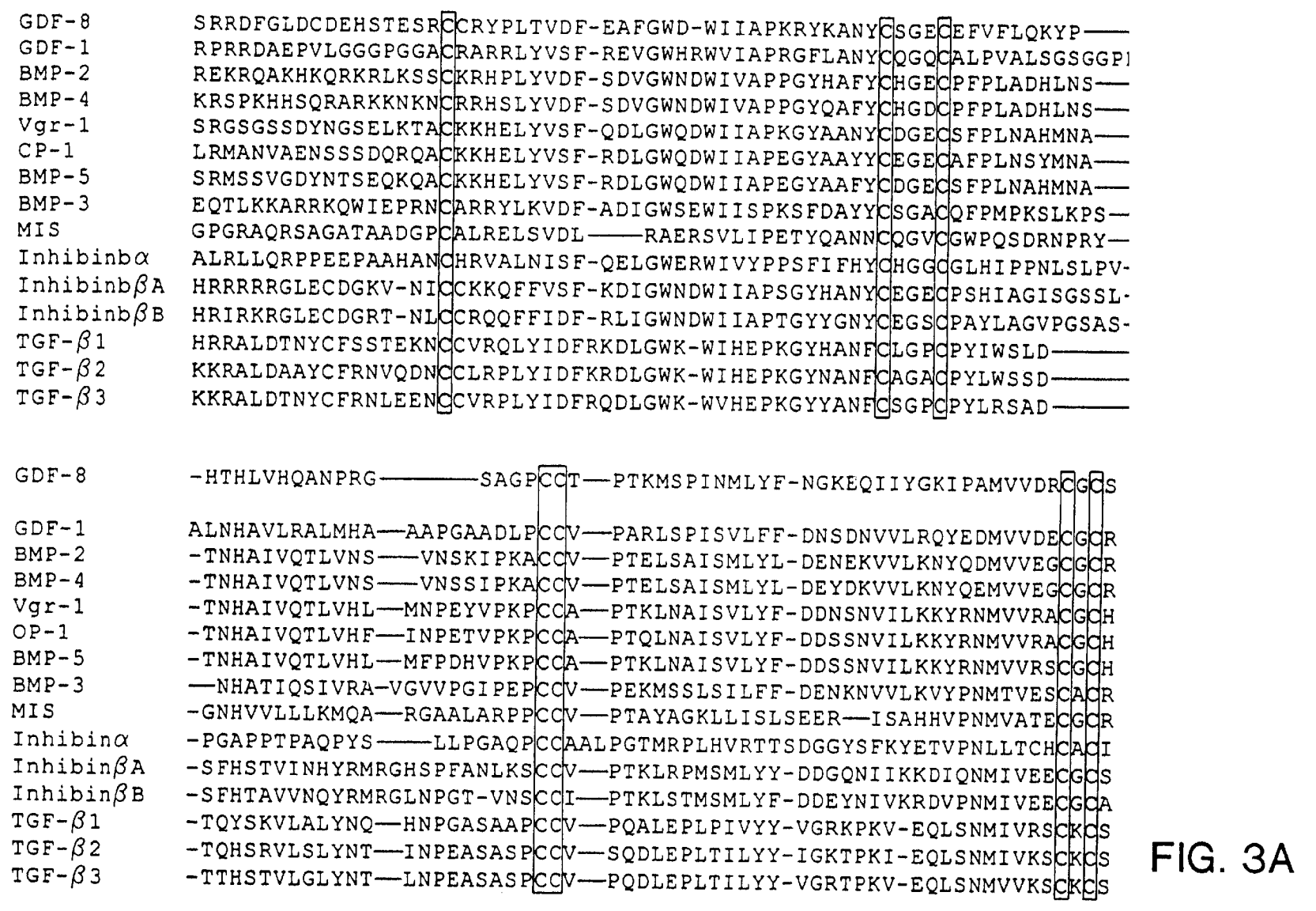

Also provided herein are the biologically active C-terminal fragments of chicken (FIG. 2c) and rat (FIG. 2d) GDF-8. The full length nucleotide and deduced amino acid sequences for baboon, bovine, chicken, rat, ovine, porcine, and turkey are shown in FIGS. 14a–g and human and murine are shown in FIG. 5. As shown in FIG. 3b, alignment of the amino acid sequences of human, murine, rat and chicken GDF-8 indicate that the sequences are 100% identical in the C-terminal biologically active fragment. FIG. 15a and 15b also show the alignment of GDF-8 amino acid sequences for murine, rat, human, baboon, porcine, ovine, bovine, chicken and turkey. Given the extensive conservation of amino acid sequences between species, it would now be routine for one of skill in the art to obtain the GDF-8 nucleic acid and amino acid sequence for GDF-8 from any species, including those provided herein, as well as piscine, for example.

The C-terminal region of GDF-8 following the putative proteolytic processing site shows significant homology to the known members of the TGF-β superfamily. The GDF-8 sequence contains most of the residues that are highly conserved in other family members and in other species(see FIGS. 3a and 3b and 15a and 15b). Like the TGF-βs and inhibin βs, GDF-8 contains an extra pair of cysteine residues in addition to the 7 cysteines found in virtually all other family members. Among the known family members, GDF-8 is most homologous to Vgr-1 (45% sequence identity; see FIG. 4).

Minor modifications of the recombinant GDF-8 primary amino acid sequence may result in proteins which have substantially equivalent activity as compared to the GDF-8 polypeptide described herein. Such modifications may be deliberate, as by site-directed mutagenesis, or may be spontaneous. All of the polypeptides produced by these modifications are included herein as long as the biological activity of GDF-8 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-8 biological activity.

The nucleotide sequence encoding the GDF-8 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the GDF-8 polynucleotide of the invention is derived from a mammalian organism, and most preferably from mouse, rat, cow, pig, or human. GDF-8 polynucleotides from chicken, turkey, fish and other species are also included herein. Screening procedures which rely on nucleic acid hybridization make it possible to isolate any gene sequence from any organism, provided the appropriate probe is available. Given the extensive nucleotide and amino acid homology between species, it would be routine for one of skill in the art to obtain polynucleotides encoding GDF-8 from any species. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res. 9:879, 1981).

The development of specific DNA sequences encoding GDF-8 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common.

This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., Nucl. Acid Res., 11:2325, 1983).

A cDNA expression library, such as lambda gt11, can be screened indirectly for GDF-8 peptides having at least one epitope, using antibodies specific for GDF-8. Such antibodies can be either polyclonally or monoclonally derived and used to detect expression product indicative of the presence of GDF-8 cDNA.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows:

2×SSC/0.1% SDS at about room temperature (hybridization conditions);

0.2×SSC/0.1% SDS at about room temperature (low stringency conditions);

0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

DNA sequences encoding GDF-8 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-8 polynucleotide sequences may be inserted into a recombinant expression vector. The term "recombinant expression vector" refers to a plasmid, virus or other vehicle known in the art that has been manipulated by insertion or incorporation of the GDF-8 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein 1, or polyhedrin promoters).

Polynucleotide sequences encoding GDF-8 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Preferably, the mature C-terminal region of GDF-8 is expressed from a cDNA clone containing the entire coding sequence of GDF-8. Alternatively, the C-terminal portion of GDF-8 can be expressed as a fusion protein with the pro-region of another member of the TGF-β family or co-expressed with another pro-region (see for example, Hammonds, et al., *Molec. Endocrinol.*, 5:149, 1991; Gray, A., and Mason, A., *Science*, 247:1328, 1990).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-8 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

GDF-8 Antibodies and Methods of Use

The invention includes antibodies immunoreactive with GDF-8 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975). The term antibody as used in this invention is meant to include intact molecules as well as fragments thereof, such as Fab and $F(ab')_2$, Fv and SCA fragments which are capable of binding an epitopic determinant on GDF-8.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An $(Fab')_2$ fragment of an antibody can be obtained by treating a whole antibody molecule with the enzyme pepsin, without subsequent reduction. A $(Fab')_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used in this invention, the term "epitope" refers to an antigenic determinant on an antigen, such as a GDF-8 polypeptide, to which the paratope of an antibody, such as an GDF-8-specific antibody, binds. Antigenic determinants usually consist of chemically active surface groupings of molecules, such as amino acids or sugar side chains, and can have specific three-dimensional structural characteristics, as well as specific charge characteristics.

As is mentioned above, antigens that can be used in producing GDF-8-specific antibodies include GDF-8 polypeptides or GDF-8 polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

The term "cell-proliferative disorder" denotes malignant as well as non-malignant cell populations which often appear to differ from the surrounding tissue both morphologically and genotypically. Malignant cells (i.e. cancer) develop as a result of a multistep process. The GDF-8 polynucleotide that is an antisense molecule or that encodes a dominant negative GDF-8 is useful in treating malignancies of the various organ systems, particularly, for example, cells in muscle or adipose tissue. Essentially, any disorder which is etiologically linked to altered expression of GDF-8 could be considered susceptible to treatment with a GDF-8 agent (e.g., a suppressing or enhancing agent). One such disorder is a malignant cell proliferative disorder, for example.

The invention provides a method for detecting a cell proliferative disorder of muscle or adipose tissue which comprises contacting an anti-GDF-8 antibody with a cell suspected of having a GDF-8 associated disorder and detecting binding to the antibody. The antibody reactive with GDF-8 is labeled with a compound which allows detection of binding to GDF-8. For purposes of the invention, an antibody specific for GDF-8 polypeptide may be used to detect the level of GDF-8 in biological fluids and tissues. Any specimen containing a detectable amount of antigen can be used. A preferred sample of this invention is muscle tissue. The level of GDF-8 in the suspect cell can be compared with the level in a normal cell to determine whether the subject has a GDF-8-associated cell proliferative disorder. Such methods of detection are also useful using nucleic acid hybridization to detect the level of GDF-8 mRNA in a sample or to detect an altered GDF-8 gene. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific anti-hapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-8-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-8-associated disease is effective. The term "ameliorate" denotes a lessening of the detrimental effect of the GDF-8-associated disease in the subject receiving therapy.

Additional Methods of Treatment and Diagnosis

The present invention identifies a nucleotide sequence that can be expressed in an altered manner as compared to expression in a normal cell, therefore it is possible to design appropriate therapeutic or diagnostic techniques directed to this sequence. Treatment includes administration of a reagent which modulates activity. The term "emodulate" envisions the suppression or expression of GDF-8 when it is over-expressed, or augmentation of GDF-8 expression when it is underexpressed. When a muscle-associated disorder is associated with GDF-8 overexpression, such suppressive reagents as antisense GDF-8 polynucleotide sequence, dominant negative sequences or GDF-8 binding antibody can be introduced into a cell. In addition, an anti-idiotype antibody which binds to a monoclonal antibody which binds GDF-8 of the invention, or an epitope thereof, may also be used in the therapeutic method of the invention. Alternatively, when a cell proliferative disorder is associated with underexpression or expression of a mutant GDF-8 polypeptide, a sense polynucleotide sequence (the DNA coding strand) or GDF-8 polypeptide can be introduced into the cell. Such muscle-associated disorders include cancer, muscular dystrophy, spinal cord injury, traumatic injury, congestive obstructive pulmonary disease (COPD), AIDS or cachexia. In addition, the method of the invention can be used in the treatment of obesity or of disorders related to abnormal proliferation of adipocytes. One of skill in the art can determine whether or not a particular therapeutic course of treatment is successful by several methods described herein (e.g., muscle fiber analysis or biopsy; determination of fat content). The present examples demonstrate that the methods of the invention are useful for decreasing fat content, and therefore would be useful in the treatment of obesity and related disorders (e.g., diabetes). Neurodegenerative disorders are also envisioned as treated by the method of the invention.

Thus, where a cell-proliferative disorder is associated with the expression of GDF-8, nucleic acid sequences that interfere with GDF-8 expression at the translational level can be used. This approach utilizes, for example, antisense nucleic acid and ribozymes to block translation of a specific GDF-8 mRNA, either by masking that mRNA with an antisense nucleic acid or by cleaving it with a ribozyme. Such disorders include neurodegenerative diseases, for example. In addition, dominant-negative GDF-8 mutants would be useful to actively interfere with function of "normal" GDF-8.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded.

Antisense oligomers of about 15 nucleotides are preferred, since they are easily synthesized and are less likely to cause problems than larger molecules when introduced into the target GDF 8 producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

In another embodiment of the present invention, a nucleotide sequence encoding a GDF-8 dominant negative protein is provided. For example, a genetic construct that contain such a dominant negative encoding gene may be operably linked to a promoter, such as a tissue-specific promoter. For example, a skeletal muscle specific promoter (e.g., human skeletal muscle α-actin promoter) or developmentally specific promoter (e.g., MyHC 3, which is restricted in skeletal muscle to the embryonic period of development, or an inducible promoter (e.g., the orphan nuclear receptor TIS1).

Such constructs are useful in methods of modulating a subject's skeletal mass. For example, a method include transforming an organism, tissue, organ or cell with a genetic construct encoding a dominant negative GDF-8 protein and suitable promoter in operable linkage and expressing the dominant negative encoding GDF-8 gene, thereby modulating muscle mass by interfering with wild-type GDF-8 activity.

GDF-8 most likely forms dimers, homodimers or heterodimers and may even form heterodimers with other GDF family members, such as GDF-11 (see Example 4). Hence, while not wanting to be bound by a particular theory, the dominant negative effect described herein may involve the formation of non-functional homodimers or heterodimers of dominant negative and wild-type GDF-8 monomers. More specifically, it is possible that any non-functional homodimer or any heterodimer formed by the dimerization of wild-type and/or dominant negative GDF-8 monomers produces a dominant effect by: 1) being synthesized but not processed or secreted; 2) inhibiting the secretion of wild type GDF-8; 3) preventing normal proteolytic cleavage of the pre-protein thereby producing a nonfinctional GDF-8 molecule; 4) altering the affinity of the non-finctional dimer (e.g., homodimeric or heterodimeric GDF-8) to a receptor or generating an antagonistic form of GDF-8 that binds a receptor without activating it; or 5) inhibiting the intracellular processing or secretion of GDF-8 related or TGF-β family proteins.

Non-functional GDF-8 can function to inhibit the growth regulating actions of GDF-8 on muscle cells that include a dominant negative GDF-8 gene. Deletion or missense dominant negative forms of GDF-8 that retain the ability to form dimers with wild-type GDF-8 protein but do not function as wild-type GDF-8 proteins may be used to inhibit the biological activity of endogenous wild- type GDF-8. For example, in one embodiment, the proteolytic processing site of GDF-8 may be altered (e.g., deleted) resulting in a GDF-8 molecule able to undergo subsequent dimerization with endogenous wild-type GDF-8 but unable to undergo further processing into a mature GDF-8 form. Alternatively, a non-functional GDF-8 can function as a monomeric species to inhibit the growth regulating actions of GDF-8 on muscle cells.

Any genetic recombinant method in the art may be used, for example, recombinant viruses may be engineered to express a dominant negative form of GDF-8 which may be used to inhibit the activity of wild-type GDF-8. Such viruses may be used therapeutically for treatment of diseases resulting from aberrant over-expression or activity of GDF-8 protein, such as in denervation hypertrophy or as a means of controlling GDF-8 expression when treating disease conditions involving muscle, such as in musculodegenerative diseases or in tissue repair due to trauma or in modulating GDF-8 expression in animal husbandry (e.g., transgenic animals for agricultural purposes).

The invention provides a method for treating a muscle or adipose tissue disorder in a subject. The method includes administering a therapeutically effective amount of a GDF-8 agent to the subject, thereby inhibiting abnormal growth of muscle or adipose tissue. The GDF-8 agent may include a GDF-8 antisense molecule or a dominant negative polypeptide, for example. A "therapeutically effective amount" of a GDF-8 agent is that amount that ameliorates symptoms of the disorder or inhibits GDF-8 induced growth of muscle, for example, as compared with a normal subject.

Gene Therapy

The present invention also provides gene therapy for the treatment of cell proliferative or immunologic disorders which are mediated by GDF-8 protein. Such therapy would achieve its therapeutic effect by introduction of the GDF-8 antisense or dominant negative encoding polynucleotide into cells having the proliferative disorder. Delivery of antisense or dominant negative GDF-8 polynucleotide can be achieved using a recombinant expression vector such as a chimeric virus or a colloidal dispersion system. Especially preferred for therapeutic delivery of antisense or dominant negative sequences is the use of targeted liposomes. In contrast, when it is desirable to enhance GDF-8 production, a "sense" GDF-8 polynucleotide or functional equivalent (e.g., the C-term active region) is introduced into the appropriate cell(s).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-8 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the GDF-8 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include, but are not limited to $\psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-8 polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Manning, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-8 in muscle and adipose tissue, there are a variety of applications using the polypeptide, polynucleotide, and antibodies of the invention, related to these tissues. Such applications include treatment of cell proliferative disorders involving these and other tissues, such as neural tissue. In addition, GDF-8 may be useful in various gene therapy procedures. In embodiments where GDF-8 polypeptide is administered to a subject, the dosage range is about 0.1 ug/kg to 100 mg/kg; more preferably from about 1 $\mu$g/kg to 75 mg/kg and most preferably from about 10 mg/kg to 50 mg/kg.

Chromosomal Location of GDF-8

The data in Example 6 shows that the human GDF-8 gene is located on chromosome 2. By comparing the chromosomal location of GDF-8 with the map positions of various human disorders, it should be possible to determine whether mutations in the GDF-8 gene are involved in the etiology of human diseases. For example, an autosomal recessive form of juvenile amyotrophic lateral sclerosis has been shown to map to chromosome 2 (Hentati, et al., *Neurology*, 42 [Suppl.3]:201, 1992). More precise mapping of GDF-8 and analysis of DNA from these patients may indicate that GDF-8 is, in fact, the gene affected in this disease. In addition, GDF-8 is useful for distinguishing chromosome 2 from other chromosomes.

Transgenic Animals and Methods of Making the Same

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, 12, Jan 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention bovine, porcine, ovine and avian animals (e.g., cow, pig, sheep, chicken, turkey). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionein, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retroviral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad Sci. USA* 82:6927–6931, 1985; Van der Putten, et al., *Proc. Natl. Acad Sci USA* 82:6148–6152, 1985). Transfection is easily and efficiently obtained by culturing the blastomeres on a monolayer of virus-producing cells (Van der Putten, supra; Stewart, et al., *EMBO J*. 6:383–388, 1987). Alternatively, infection can be performed at a later stage. Virus or virus-producing cells can be injected into the blastocoele (D. Jahner et al., *Nature* 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., Proc. Natl. Acad Sci USA 83: 9065–9069, 1986; and Robertson et al., Nature 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal (for review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode GDF-8, and include GDF-sense, antisense, dominant negative encoding polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knockout". An example of a transgene used to "knockout" GDF-8 function in the present Examples is described in Example 8 and FIG. 12a. Thus, in another embodiment, the invention provides a transgene wherein the entire mature C-terminal region of GDF-8 is deleted.

The transgene to be used in the practice of the subject invention is a DNA sequence comprising a modified GDF-8 coding sequence. In a preferred embodiment, the GDF-8 gene is disrupted by homologous targeting in embryonic stem cells. For example, the entire mature C-terminal region of the GDF-8 gene may be deleted as described in the examples below. Optionally, the GDF-8 disruption or deletion may be accompanied by insertion of or replacement with other DNA sequences, such as a non-functional GDF-8 sequence. In other embodiments, the transgene comprises DNA antisense to the coding sequence for GDF-8. In another embodiment, the transgene comprises DNA encoding an antibody or receptor peptide sequence which is able to bind to GDF-8. The DNA and peptide sequences of GDF-8 are known in the art, the sequences, localization and activity disclosed in WO94/21681 and U.S. patent application Ser. No. 08/033,923, filed on Mar. 19, 1993 (see U.S. Pat. No. 5,827,733), incorporated by reference in its entirety. The disclosure of both of these applications are hereby incorporated herein by reference. Where appropriate, DNA sequences that encode proteins having GDF-8 activity but differ in nucleic acid sequence due to the degeneracy of the genetic code may also be used herein, as may truncated forms, allelic variants and interspecies homologues.

The invention also includes animals having heterozygous mutations in GDF-8 or partial inhibition of GDF-8 finction or expression. A heterozygote would exhibit an intermediate increase in muscle mass as compared to the homozygote as shown in Table 4 below. In other words, partial loss of function leads to a partial increase in muscle mass. One of skill in the art would readily be able to determine if a particular mutation or if an antisense molecule was able to partially inhibit GDF-8. For example, in vitro testing may be desirable initially by comparison with wild-type or untreated GDF-8 (e.g., comparison of northern blots to examine a decrease in expression).

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. To be able to distinguish expression of like-species transgenes from expression of the animals endogenous GDF-8 gene(s), a marker gene fragment can be included in the construct in the 3' untranslated region of the transgene and the Northern probe designed to probe for the marker gene fragment. The serum levels of GDF-8 can also be measured in the transgenic animal to establish appropriate expression. Expression of the GDF-8 transgenes, thereby decreasing the GDF-8 in the tissue and serum levels of the transgenic animals and consequently increasing the muscle tissue content results in the foodstuffs from these animals (i.e. eggs, beef, pork, poultry meat, milk, etc.) having markedly increased muscle content, and preferably without increased, and more preferably, reduced levels of fat and cholesterol. By practice of the subject invention, a statistically significant increase in muscle content, preferably at least a 2% increase in muscle content (e.g., in chickens), more preferably a 25% increase in muscle content as a percentage of body weight, more preferably greater than 40% increase in muscle content in these foodstuffs can be obtained.

Additional Methods of Use

Thus, the present invention includes methods for increasing muscle mass in domesticated animals, characterized by inactivation or deletion of the gene encoding growth and differentiation factor-8 (GDF-8). The domesticated animal is preferably selected from the group consisting of ovine, bovine, porcine, piscine and avian. The animal may be treated with an isolated polynucleotide sequence encoding growth and differentiation factor-8 which polynucleotide sequence is also from a domesticated animal selected from the group consisting of ovine, bovine, porcine, piscine and avian. The present invention includes methods for increasing the muscle mass in domesticated animals characterized by administering to a domesticated animal monoclonal antibodies directed to the GDF-8 polypeptide. The antibody may be an anti-GDF-8, and may be either a monoclonal antibody or a polyclonal antibody.

The invention includes methods comprising using an anti-GDF-8 monoclonal antibody, antisense, or dominant negative mutants as a therapeutic agent to inhibit the growth regulating actions of GDF-8 on muscle cells. Muscle cells are defined to include fetal or adult muscle cells, as well as progenitor cells which are capable of differentiation into muscle. The monoclonal antibody may be a humanized (e.g., either fully or a chimeric) monoclonal antibody, of any species origin, such as murine, ovine, bovine, porcine or avian. Methods of producing antibody molecules with various combinations of "humanized" antibodies are well known in the art and include combining murine variable regions with human constant regions (Cabily, et al. *Proc. Natl. Acad. Sci. USA*, 81:3273, 1984), or by grafting the murine-antibody complementary determining regions (CDRs) onto the human framework (Richmann, et al., *Nature* 332:323, 1988). Other general references which teach methods for creating humanized antibodies include Morrison, et al., *Science*, 229:1202, 1985; Jones, et al., *Nature*, 321:522, 1986; Monroe, et al., *Nature* 312:779, 1985; Oi, et al., *BioTechniques*, 4:214, 1986; European Patent Application No. 302,620; and U.S. Pat. No. 5,024,834. Therefore, by humanizing the monoclonal antibodies of the invention for in vivo use, an immune response to the antibodies would be greatly reduced.

The monoclonal antibody, GDF-8 polypeptide, or GDF-8 polynucleotide (all "GDF-8 agents") may have the effect of increasing the development of skeletal muscles. In preferred embodiments of the claimed methods, the GDF-8 monoclonal antibody, polypeptide, or polynucleotide is administered to a patient suffering from a disorder selected from the group consisting of muscle wasting disease, neuromuscular disorder, muscle atrophy or aging. The GDF-8 agent may also be administered to a patient suffering from a disorder selected from the group consisting of muscular dystrophy, spinal cord injury, traumatic injury, congestive obstructive pulmonary disease (COPD), AIDS or cachexia. In a preferred embodiment, the GDF-8 agent is administered to a patient with muscle wasting disease or disorder by intravenous, intramuscular or subcutaneous injection; preferably, a monoclonal antibody is administered within a dose range between about 0.1 mg/kg to about 100 mg/kg; more preferably between about 1 µg/kg to 75 mg/kg; most preferably from about 10 mg/kg to 50 mg/kg. The antibody may be administered, for example, by bolus injunction or by slow infusion. Slow infusion over a period of 30 minutes to 2 hours is preferred. The GDF-8 agent may be formulated in a formulation suitable for administration to a patient. Such formulations are known in the art.

The dosage regimen will be determined by the attending physician considering various factors which modify the action of the GDF-8 protein, e.g. amount of tissue desired to be formed, the site of tissue damage, the condition of the damaged tissue, the size of a wound, type of damaged tissue, the patient's age, sex, and diet, the severity of any infection, time of administration and other clinical factors. The dosage may vary with the type of matrix used in the reconstitution and the types of agent, such as anti-GDF-8 antibodies, to be used in the composition. Generally, systemic or injectable administration, such as intravenous (IV), intramuscular (IM) or subcutaneous (Sub-Q) injection. Administration will generally be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), human, bovine, or chicken growth hormone which may aid in increasing muscle mass, to the final composition, may also affect the dosage. In the embodiment where an anti-GDF-8 antibody is administered, the anti-GDF-8 antibody is generally administered within a dose range of about 0.1 µg/kg to about 100 mg/kg; more preferably between about 10 mg/kg to 50 mg/kg.

Progress can be monitored by periodic assessment of tissue growth and/or repair. The progress can be monitored, for example, X-rays, histomorphometric determinations and tetracycline labeling.

Screening for GDF-8 Modulating Compounds

In another embodiment, the invention provides a method for identifying a compound or molecule that modulates GDF-8 protein activity or gene expression. The method includes incubating components comprising the compound, GDF-8 polypeptide or with a recombinant cell expressing GDF-8 polypeptide, under conditions sufficient to allow the components to interact and determining the effect of the compound on GDF-8 activity or expression. The effect of the compound on GDF-8 activity can be measured by a number of assays, and may include measurements before and after incubating in the presence of the compound. Compounds that affect GDF-8 activity or gene expression include peptides, peptidomimetics, polypeptides, chemical compounds and biologic agents. Assays include Northern blot analysis of GDF-8 mRNA (for gene expression), Western blot analysis (for protein level) and muscle fiber analysis (for protein activity).

The above screening assays may be used for detecting the compounds or molecules that bind to the GDF-8 receptor or GDF-8 polypeptide, in isolating molecules that bind to the GDF-8 gene, for measuring the amount of GDF-8 in a sample, either polypeptide or RNA (mRNA), for identifying molecules that may act as agonists or antagonists, and the like. For example, GDF-8 antagonists are useful for treatment of muscular and adipose tissue disorders (e.g., obesity).

Incubating includes conditions which allow contact between the test compound and GDF-8 polypeptide or with a recombinant cell expressing GDF-8 polypeptide. Contacting includes in solution and in solid phase, or in a cell. The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad Sci. USA*, 80:278, 1983), oligonucleotide Landegren, et al., *Science*, 21:1077, 1988), and the like. Molecular techniques for DNA analysis have been reviewed (Landegren, et al., *Science*, 242:229–237, 1988).

All references cited herein are hereby incorporated by reference in their entirety.

The following examples are intended to illustrate but not limit the invention. While they are typical of those that might be used, other procedures known to those skilled in the art may alternatively be used.

EXAMPLE 1

Identification and Isolation of a Novel TGF-β Family Member

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on mouse genomic DNA followed by subcloning the PCR products using restriction sites placed at the 5' ends of the primers, picking individual E. coli colonies carrying these subcloned inserts, and using a combination of random sequencing and hybridization analysis to eliminate known members of the superfamily.

GDF-8 was identified from a mixture of PCR products obtained with the primers

SJL141: 5'-CCGGAATTCGGITGG(G/C/A)A(G/A/T/C) (A/G)A(T/C)TGG(A/G)TI (A/G)TI(T/G)CICC-3' (SEQ ID NO:1)

SJL147: 5'-CCGGAATTC(G/A)CAI(G/C)C(G/A)CA(G/A)CT(GIA/T/C) TCIACI(G/A)(T/C)CAT-3' (SEQ ID NO:2)

PCR using these primers was carried out with 2 μg mouse genomic DNA at 94° C. for 1 min, 50° C. for 2 min, and 72° C. for 2 min for 40 cycles.

PCR products of approximately 280 bp were gel-purified, digested with Eco RI, gel-purified again, and subcloned in the Bluescript vector (Stratagene, San Diego, Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from non-hybridizing colonies for sequence analysis.

The primer combination of SJL141 and SJL147, encoding the amino acid sequences GW(H/Q/N/K/D/E)(D/N)W(V/I/M)(V/I/M)(A/S)P (SEQ ID NO:9) and M(V/I/M/T/A)V(D/E)SC(G/A)C (SEQ ID NO: 10), respectively, yielded four previously identified sequences (BMP-4, inhibin, PB, GDF-3 and GDF-5) and one novel sequence, which was designated GDF-8, among 110 subclones analyzed.

Human GDF-8 was isolated using the primers:

ACM13:
5'-CGCGGATCCAGAGTCAAGGTGACAGACACA-C-3' (SEQ ID NO:3); and

ACM14:
5'-CGCGGATCCTCCTCATGAGCACCCACAGCG-GTC-3' (SEQ ID NO:4)

PCR using these primers was carried out with one μg human genomic DNA at 94° C. for 1 min, 58° C. for 2 min, and 72° C. for 2 min for 30 cycles. The PCR product was digested with Bam Hl, gel-purified, and subcloned in the Bluescript vector (Stratagene, San Francisco, Calif.).

EXAMPLE 2

Expression Pattern and Sequence of GDF-8

To determine the expression pattern of GDF-8, RNA samples prepared from a variety of adult tissues were screened by Northern analysis. RNA isolation and Northern analysis were carried out as described previously (Lee, S. J., Mol. Endocrinol., 4:1034, 1990) except that hybridization was carried out in 5X SSPE, 10% dextran sulfate, 50% formamide, 1% SDS, 200 μg/ml salmon DNA, and 0.1% each of bovine serum albumin, ficoll, and polyvinylpyrrolidone. Five micrograms of twice poly A-selected RNA prepared from each tissue (except for muscle, for which only 2 μg RNA was used) were electrophoresed on formaldehyde gels, blotted, and probed with GDF-8. As shown in FIG. 1, the GDF-8 probe detected a single mRNA species expressed at highest levels in muscle and at significantly lower levels in adipose tissue.

To obtain a larger segment of the GDF-8 gene, a mouse genomic library was screened with a probe derived from the GDF-8 PCR product. The partial sequence of a GDF-8 genomic clone is shown in FIG. 2a. The sequence contains an open reading frame corresponding to the predicted C-terminal region of the GDF-8 precursor protein. The predicted GDF-8 sequence contains two potential proteolytic processing sites, which are boxed. Cleavage of the precursor at the second of these sites would generate a mature C terminal fragment 109 amino acids in length with a predicted molecular weight of 12,400. The partial sequence of human GDF-8 is shown in FIG. 2b. Assuming no PCR-induced errors during the isolation of the human clone, the human and mouse amino acid sequences in this region are 100% identical.

The C-terminal region of GDF-8 following the putative proteolytic processing site shows significant homology to the known members of the TGF-β; superfamily (FIG. 3). FIG. 3 shows the alignment of the C-terminal sequences of GDF-8 with the corresponding regions of human GDF-I (Lee, Proc. Natl. Acad Sci. USA, 88:4250–4254, 1991), human BMP-2 and 4 (Wozney, et al., Science, 242:1528–1534, 1988), human Vgr-1 (Celeste, et al. Proc. Natl. Acad. Sci. USA, 87:9843–9847, 1990), human OP-1 (Ozkaynak, et al., EMBO J., 9:2085–2093, 1990), human BMP-5 (Celeste, et al., Proc. Natl. Acad. Sci. USA, 87:9843–9847, 1990), human BMP-3 (Wozney, et al., Science, 242:1528–1534, 1988), human MiS (Cate, et al. Cell, 45:685–698,1986), human inhibin alpha, βA, and βB (Mason, et al., Biochem, Biophys. Res. Commun., 135:957–964, 1986), human TGF-β1 (Derynck, et al., Nature, 316:701–705, 1985), human TGF-R2 (deMartin, et al., EMBO J., 6:3673–3677, 1987), and human TGF-β3 (ten Dijke, et al., Proc. Natl. Acad. Sci. USA, 85:4715–4719, 1988). The conserved cysteine residues are boxed. Dashes denote gaps introduced in order to maximize the alignment.

GDF-8 contains most of the residues that are highly conserved in other family members, including the seven cysteine residues with their characteristic spacing. Like the TGF-βs and inhibin βs, GDF-8 also contains two additional cysteine residues. In the case of TGF-β2, these two additional cysteine residues are known to form an intramolecular disulfide bond (Daopin, et al., Science, 257:369, 1992; Schlunegger and Grutter, Nature, 358:430, 1992).

FIG. 4 shows the amino acid homologies among the different members of the TGF-β superfamily. Numbers represent percent amino acid identities between each pair calculated from the first conserved cysteine to the C terminus. Boxes represent homologies among highly-related members within particular subgroups. In this region, GDF-8 is most homologous to Vgr-1 (45% sequence identity).

EXAMPLE 3

Isolation of cDNA Clones Encoding Murine and Human GDF-8

In order to isolate full-length cDNA clones encoding murine and human GDF-8, cDNA libraries were prepared in the lambda ZAP II vector (Stratagene) using RNA prepared from skeletal muscle. From 5 μg of twice poly A-selected RNA prepared from murine and human muscle, cDNA libraries consisting of 4.4 million and 1.9 million recombinant phage, respectively, were constructed according to the instructions provided by Stratagene. These libraries were screened without amplification. Library screening and characterization of cDNA inserts were carried out as described previously (Lee, *Mol. Endocrinol.*, 4:1034–1040).

Figure 6A:
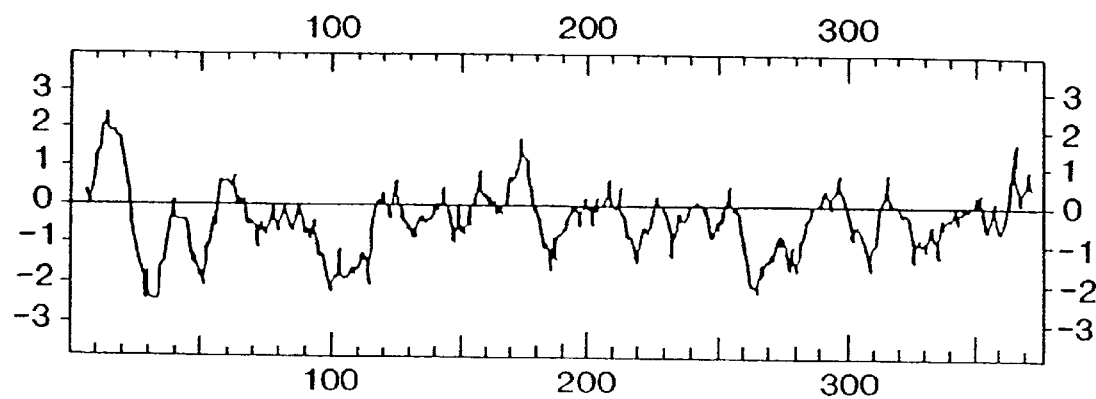
FIGS. 6a and 6b show a hydropathicity profile of GDF-8. Average hydrophobicity values for murine (FIG. 6a) and human (FIG. 6b) GDF-8 were calculated using the method of Kyte and Doolittle (*J. Mol. Biol.*, 157:105–132, 1982). Positive numbers indicate increasing hydrophobicity.

From $2.4\times10^6$ recombinant phage screened from the murine muscle cDNA library, greater than 280 positive phage were identified using a murine GDF-8 probe derived from a genomic clone, as described in Example 1. The entire nucleotide sequence of the longest cDNA insert analyzed is shown in FIG. 5a and 5b and SEQ ID NO: 11. The 2676 base pair sequence contains a single long open reading frame beginning with a methionine codon at nucleotide 104 and extending to a TGA stop codon at nucleotide 1232. Upstream of the putative initiating methionine codon is an in-frame stop codon at nucleotide 23. The predicted pre-pro-GDF-8 protein is 76 amino acids in length. The sequence contains a core of hydrophobic amino acids at the N-terminus suggestive of a signal peptide for secretion (FIG. 6a), one potential N-glycosylation site at asparagine 72, a putative RXXR (SEQ ID NO: 50) proteolytic cleavage site at amino acids 264–267, and a C-terminal region showing significant homology to the known members of the TGF-β superfamily. Cleavage of the precursor protein at the putative RXXR (SEQ ID NO: 50) site would generate a mature C-terminal GDF-8 fragment 109 amino acids in length with a predicted molecular weight of approximately 12,400.

Figure 6B:
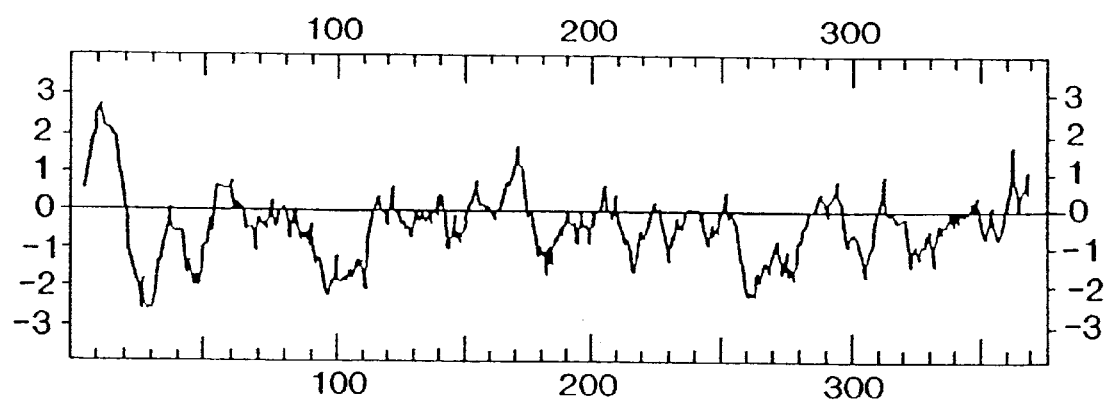

From $1.9\times10^6$ recombinant phage screened from the human muscle cDNA library, 4 positive phage were identified using a human GDF-8 probe derived by polymerase chain reaction on human genomic DNA. The entire nucleotide sequence of the longest cDNA insert is shown in FIG. 5c and 5d and SEQ ID NO: 13. The 2743 base pair sequence contains a single long open reading frame beginning with a methionine codon at nucleotide 59 and extending to a TGA stop codon at nucleotide 1184. The predicted pre-pro-GDF-8 protein is 375 amino acids in length. The sequence contains a core of hydrophobic amino acids at the N-terminus suggestive of a signal peptide for secretion (FIG. 6b), one potential N-glycosylation site at asparagine 71, and a putative RXXR (SEQ ID NO:50) proteolytic cleavage site at amino acids 263–266. FIG. 7 shows a comparison of the predicted murine (top) and human (bottom) GDF-8 amino acid sequences. Numbers indicate amino acid position relative to the N-terminus. Identities between the two sequences are denoted by a vertical line. Murine and human GDF-8 are approximately 94% identical in the predicted pro-regions and 100% identical following the predicted RXXR (SEQ ID NO:50) cleavage sites.

EXAMPLE 4

Dimerization of GDF- 8

To determine whether the processing signals in the GDF-8 sequence are functional and whether GDF-8 forms dimers like other members of the TGF-β superfamily, the GDF-8 cDNA was stably expressed in CHO cells. The GDF-8 coding sequence was cloned into the pMSXND expression vector (Lee and Nathans, *J. Biol. Chem.*, 263:3521, (1988) and transfected into CHO cells. Following G418 selection, the cells were selected in 0.2 μM methotrexate, and conditioned medium from resistant cells was concentrated and electrophoresed on SDS gels. Conditioned medium was prepared by Cell Trends, Inc. (Middletown, Md.). For preparation of anti-GDF-8 serum, the C-terminal region of GDF-8 (amino acids 268 to 376) was expressed in bacteria using the RSET vector (Invitrogen, San Diego, Calif.), purified using a nickel chelate column, and injected into rabbits. All immunizations were carried out by Spring Valley Labs (Woodbine, Md.). Western analysis using [$^{125}$I]-iodoprotein A was carried out as described (Burnette, W. N., *Anal. Biochem.*, 112:195, 1981). Western analysis of conditioned medium prepared from these cells using an antiserum raised against a bacterially-expressed C-terminal fragment of GDF-8 detected two protein species with apparent molecular weights of approximately 52kD and 15kD under reducing conditions, consistent with unprocessed and processed forms of GDF-8, respectively. No bands were obtained either with preimmune serum or with conditioned medium from CHO cells transfected with an antisense construct. Under non-reducing conditions, the GDF-8 antiserum detected two predominant protein species with apparent molecular weights of approximately 101 kD and 25 kD, consistent with dimeric forms of unprocessed and processed GDF-8, respectively. Hence, like other TGF-β family members, GDF-8 appears to be secreted and proteolytically processed, and the C-terminal region appears to be capable of forming

EXAMPLE 5

Figure 8:
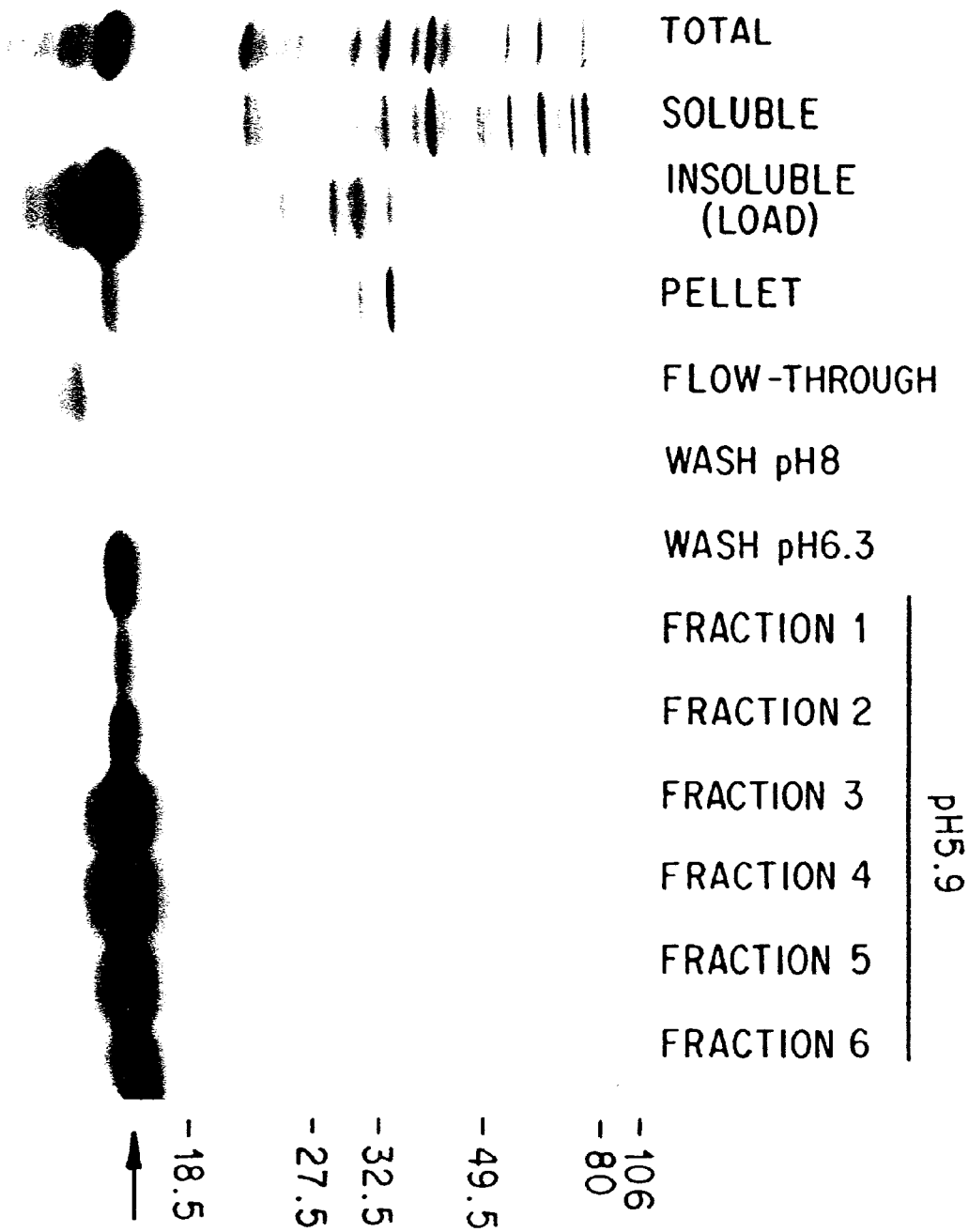
FIG. 8 shows the expression of GDF-8 in bacteria. BL21 (DE3) (pLysS) cells carrying a pRSET/GDF-8 expression plasmid were induced with isopropylthio-β-galactoside, and the GDF-8 fusion protein was purified by metal chelate chromatography. Lanes: total=total cell lysate; soluble=soluble protein fraction; insoluble=insoluble protein fraction (resuspended in 10 mM Tris pH 8.0, 50 mM sodium phosphate, 8 M urea, and 10 mM β-mercaptoethanol [buffer B]) loaded onto the column, pellet=insoluble protein fraction discarded before loading the column; flowthrough=proteins not bound by the column; washes=washes carried out in buffer B at the indicated pH's. Positions of molecular weight standards are shown at the right. Arrow indicates the position of the GDF-8 fusion protein.

Preparation of Antibodies Against GDF-8 and Expression of GDF-8 in Mammalian Calls In order to prepare antibodies against GDF-8, GDF-8 antigen was expressed as a fusion protein in bacteria. A portion of murine GDF-8 cDNA spanning amino acids 268–376 (mature region) was inserted into the pRSET vector (Invitrogen) such that the GDF-8 coding sequence was placed in frame with the initiating methionine codon present in the vector; the resulting construct created an open reading frame encoding a fusion protein with a molecular weight of approximately 16,600. The fusion construct was transformed into BL21 (DE3) (pLysS) cells, and expression of the fusion protein was induced by treatment with isopropylthio-β-galactoside as described (Rosenberg, et al., *Gene*, 56:125–135). The fusion protein was then purified by metal chelate chromatography according to the instructions provided by Invitrogen. A Coomassie blue-stained gel of unpurified and purified fusion proteins is shown in FIG. 8.

The purified fusion protein was used to immunize both rabbits and chickens. Immunization of rabbits was carried out by Spring Valley Labs (Sykesville, Md.), and immunization of chickens was carried out by HRP, Inc. (Denver, Pa.). Western analysis of sera both from immunized rabbits and from immunized chickens demonstrated the presence of antibodies directed against the fusion protein.

To express GDF-8 in mammalian cells, the murine GDF-8 cDNA sequence from nucleotides 48-1303 was cloned in both orientations downstream of the metallothionein I promoter in the pMSXND expression vector; this vector contains processing signals derived from SV40, a dihydrofolate reductase gene, and a gene conferring resistance to the antibiotic G418 (Lee and Nathans, *J. Biol. Chem.*, 263:3521–3527). The resulting constructs were transfected into Chinese hamster ovary cells, and stable transfectants were selected in the presence of G418. Two milliliters of conditioned media prepared from the G418-resistant cells were dialyzed, lyophilized, electrophoresed under denaturing, reducing conditions, transferred to nitrocellulose, and incubated with anti-GDF-8 antibodies (described above) and [$^{125}$I]-iodoprotein A.

Figure 9:
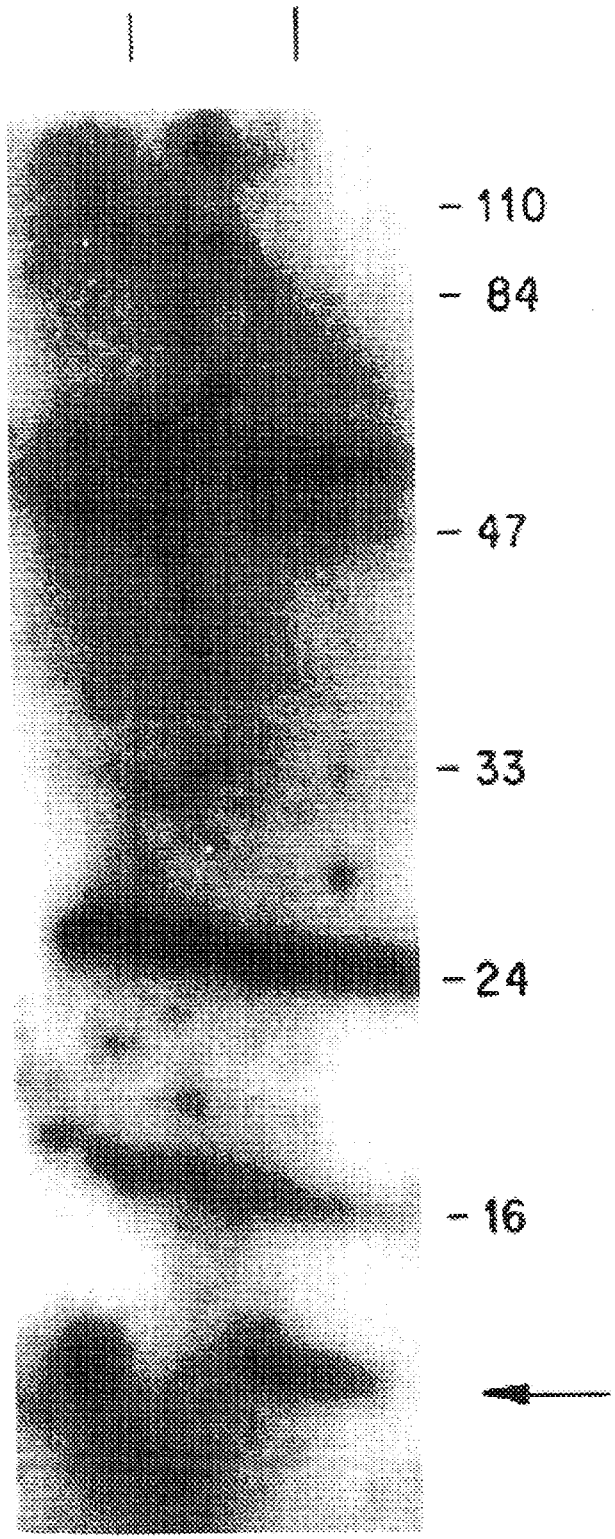
FIG. 9 shows the expression of GDF-8 in mammalian cells. Chinese hamster ovary cells were transfected with pMSXND/GDF-8 expression plasmids and selecnted in G418. Conditioned media from G418-resistant cells (prepared from cells transfected with constructs in which GDF-8 was cloned in either the antisense or sense orientation) were concentrated, electrophoresed under reducing conditions, blotted, and probed with anti-GDF-8 antibodies and [$^{125}$I]-iodoprotein A. Arrow indicates the position of the processed GDF-8 protein.

As shown in FIG. 9, the rabbit GDF-8 antibodies (at a 1:500 dilution) detected a protein of approximately the predicted molecular weight for the mature C-terminal fragment of GDF-8 in the conditioned media of cells transfected with a construct in which GDF-8 had been cloned in the correct (sense) orientation with respect to the metallothionein promoter (lane 2); this band was not detected in a similar sample prepared from cells transfected with a control antisense construct (lane 1). Similar results were obtained using antibodies prepared in chickens. Hence, GDF-8 is secreted and proteolytically processed by these transfected mammalian cells.

EXAMPLE 6

Expression Pattern of GDF-8

Figure 10B:
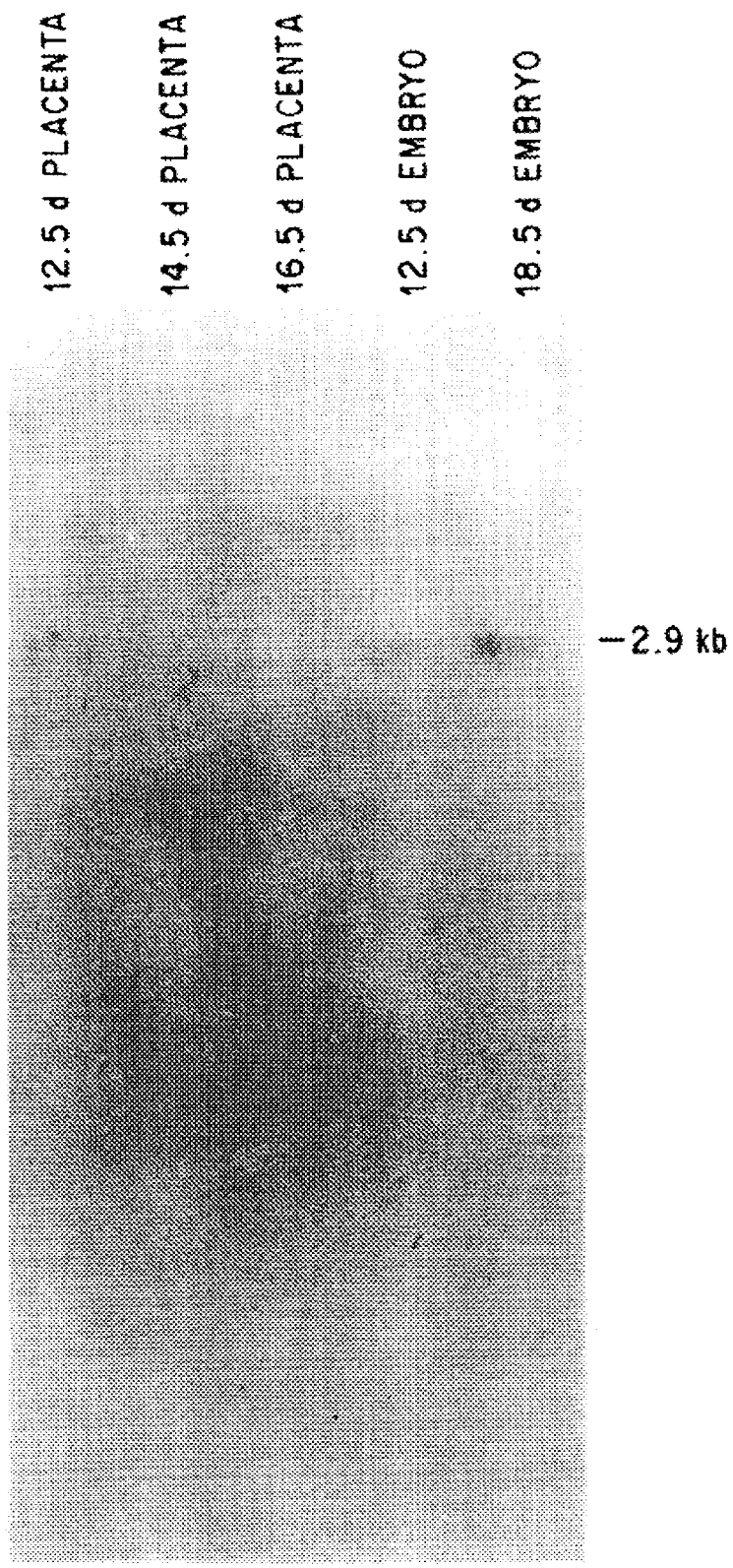

To determine the pattern of GDF-8, 5 μg of twice poly A-selected RNA prepared from a variety of murine tissue sources were subjected to Northern analysis. As shown in FIG. 10a (and as shown previously in Example 2), the GDF-8 probe detected a single mRNA species present almost exclusively in skeletal muscle among a large number of adult tissues surveyed. On longer exposures of the same blot, significantly lower but detectable levels of GDF-8 mRNA were seen in fat, brain, thymus, heart, and lung. Hence, these results confirm the high degree of specificity of GDF-8 expression in skeletal muscle. GDF-8 mRNA was also detected in mouse embryos at both gestational ages (day 12.5 and day 18.5 post-coital) examined but not in placentas at various stages of development (FIG. 10b).

To further analyze the expression pattern of GDF-8, in situ hybridization was performed on mouse embryos isolated at various stages of development.

For all in situ hybridization experiments, probes corresponding to the C-terminal region of GDF-8 were excluded in order to avoid possible cross-reactivity with other members of the superfamily. Whole mount in situ hybridization analysis was carried out as described (Wilkinson, D. G., *In Situ Hybridization, A Practical Approach*, pp. 75–83, IRL Press, Oxford, 1992) except that blocking and antibody incubation steps were carried out as in Knecht et al. (Knecht, et al., *Development*, 121:1927, 1955). Alkaline phosphatase reactions were carried out for 3 hours for day 10.5 embryos and overnight for day 9.5 embryos. Hybridization was carried out using digoxigenin-labeled probes spanning nucleotides 8–811 and 1298–2676, which correspond to the pro-region and 3' untranslated regions, respectively. In situ hybridization to sections was carried out as described (Wilkinson, et al., *Cell*, 50:79, 1987) using $^{35}$S-labelled probes ranging from approximately 100–650 bases in length and spanning nucleotides 8–793 and 1566–2595. Following hybridization and washing, slides were dipped in NTB-3 photographic emulsion, exposed for 16–19 days, developed and stained with either hematoxylin and eosin or toluidine blue. RNA isolation, poly A selection, and Northern analysis were carried out as described previously (McPherron and Lee, *J. Biol. Chem.*, 268:3444, 1993).

At all stages examined, the expression of GDF-8 mRNA appeared to be restricted to developing skeletal muscle. At early stages, GDF-8 expression was restricted to developing somites. By whole mount in situ hybridization analysis, GDF-8 mRNA could first be detected as early as day 9.5 post coitum in approximately one-third of the somites. At this stage of development, hybridization appeared to be restricted to the most mature (9 out of 21 in this example), rostral somites. By day 10.5 p.c., GDF-8 expression was clearly evident in almost every somite (28 out of 33 in this example shown). Based on in situ hybridization analysis of sections prepared from day 10.5 p.c. embryos, the expression of GDF-8 in somites appeared to be localized to the myotome compartment. At later stages of development, GDF-8 expression was detected in a wide range of developing muscles. GDF-8 continues to be expressed in adult animals as well. By Northern analysis, GDF-8 mRNA expression was seen almost exclusively in skeletal muscle among the different adult tissues examined. A significantly lower though clearly detectable signal was also seen in adipose tissue. Based on Northern analysis of RNA prepared from a large number of different adult skeletal muscles, GDF-8 expression appeared to be widespread although the expression levels varied among individual muscles.

EXAMPLE 7

Chromosomal Localiazation of GDF-8

In order to map the chromosomal location of GDF-8, DNA samples from human/rodent somatic cell hybrids (Drwinga, et al., *Genomics*, 16:311–413, 1993; Dubois and Naylor, *Genomics*, 16:315–319, 1993) were analyzed by polymerase chain reaction followed by Southern blotting. Polymerase chain reaction was carried out using primer #83, 5'-CGCGGATCCGTGGATCTAAAT GAGAACAGTGAGC-3' (SEQ ID NO: 15) and primer #84, 5'-CGCGAATTCTCAGGTAATGATTGT TTCCGTTGTAGCG-3' (SEQ ID NO:16)

for 40 cycles at 94° C. for 2 minutes, 60° C. for 1 minute, and 72° C. for 2 minutes. These primers correspond to nucleotides 119 to 143 (flanked by a Bam HI recognition sequence), and nucleotides 394 to 418 (flanked by an Eco RI recognition sequence), respectively, in the human GDF-8 cDNA sequence. PCR products were electrophoresed on agarose gels, blotted, and probed with oligonucleotide #100, 5'-ACACTAAATCTTCAAGAATA-3' (SEQ ID NO:17), which corresponds to a sequence internal to the region flanked by primer #83 and #84. Filters were hybridized in 6 X SSC, 1 X Denhardt's solution, 100 μg/ml yeast transfer RNA, and 0.05% sodium pyrophosphate at 50° C.

Figure 11:
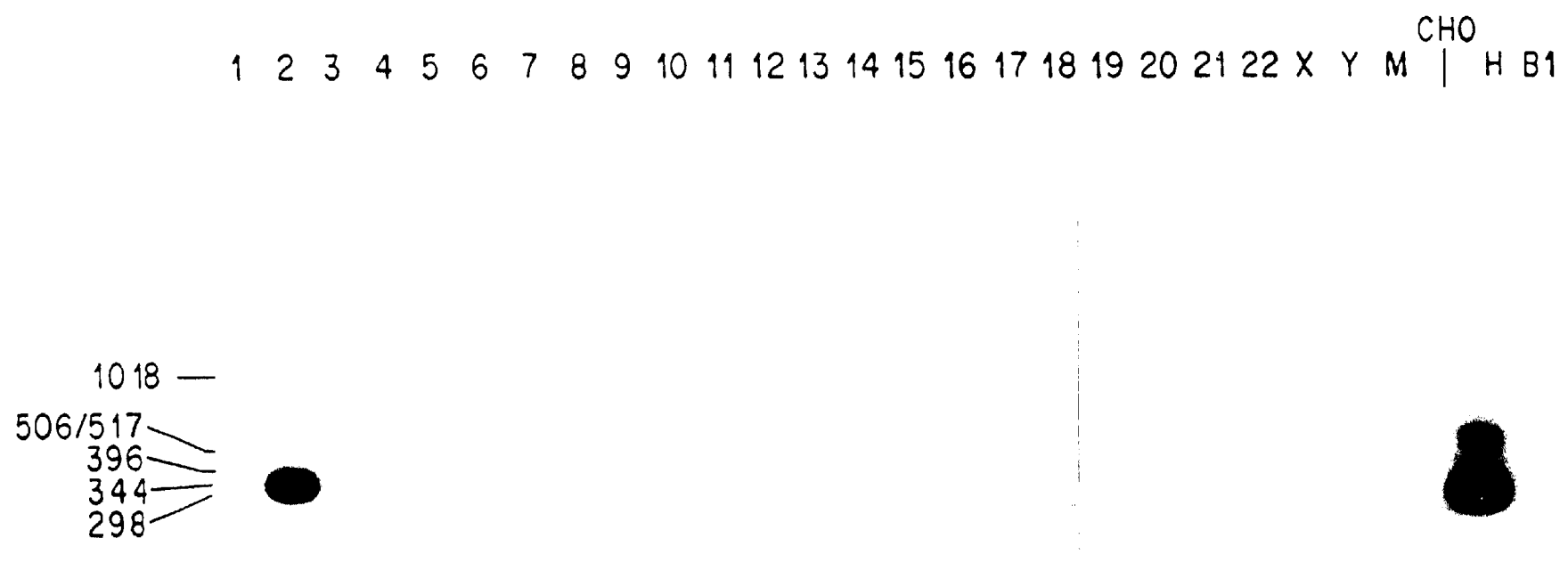

As shown in FIG. 11, the human-specific probe detected a band of the predicted size (approximately 320 base pairs) in the positive control sample (total human genomic DNA) and in a single DNA sample from the human/rodent hybrid panel. This positive signal corresponds to human chromosome 2. The human chromosome contained in each of the hybrid cell lines is identified at the top of each of the first 24 lanes (1–22, X, and Y). In the lanes designated M, CHO, and H, the starting DNA template was total genomic DNA from mouse, hamster, and human sources, respectively. In the lane marked B1, no template DNA was used. Numbers at left indicate the mobilities of DNA standards. These data show that the human GDF-8 gene is located on chromosome 2.

EXAMPLE 8

GDF-8 Transgenic Knockout Mice

Figure 12A:
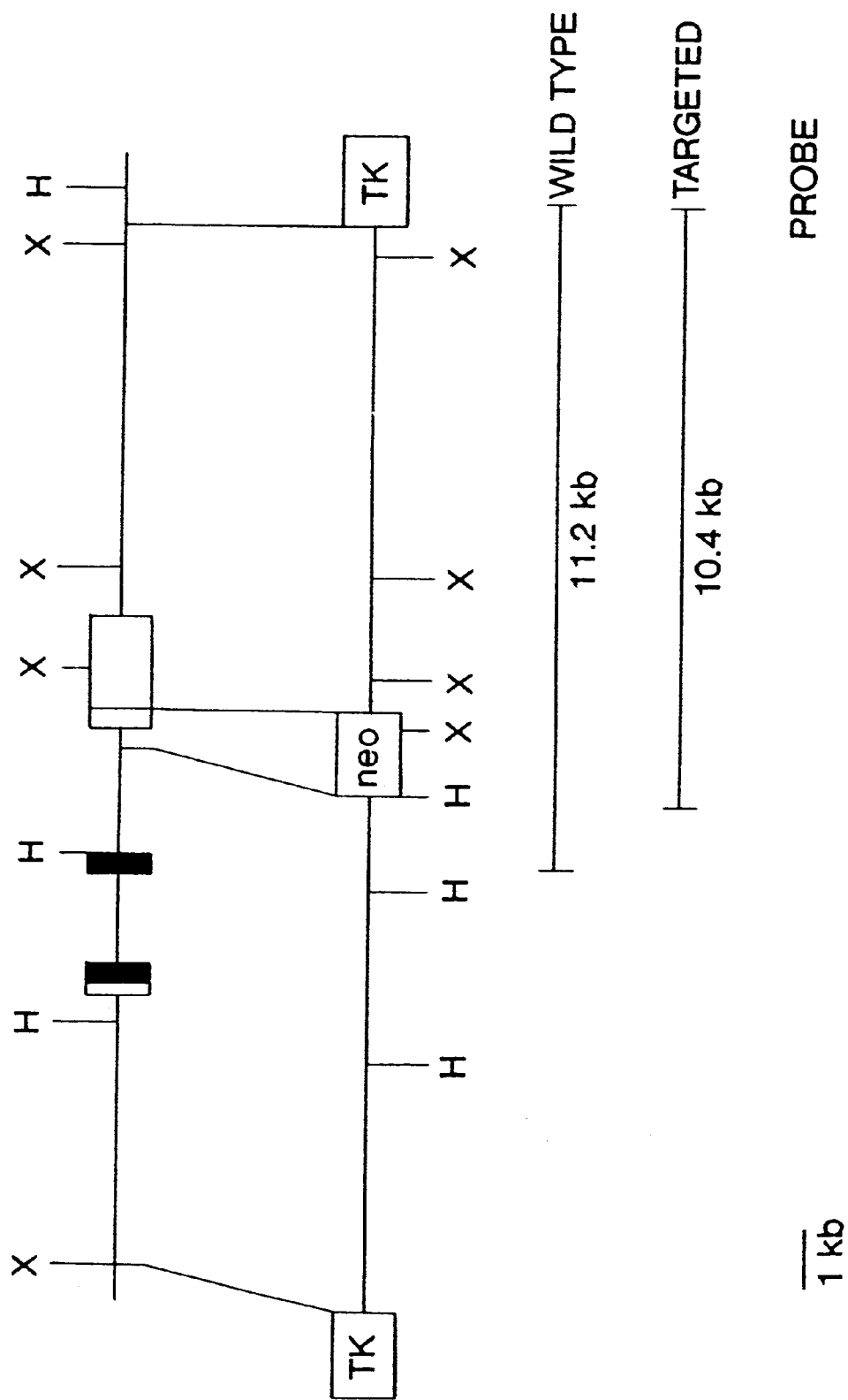
FIG. 12a shows a map of the GDF-8 locus (top line) and targeting construct (second line). The black and stippled boxes represent coding sequences for the pro- and C-terminal regions, respectively. The white boxes represent 5' and 3' untranslated sequences. A probe derived from the region downstream of the 3' homology fragment and upstream of the most distal HindIII site shown hybridizes to an 11.2 kb HindIII fragment in the GDF-8 gene and a 10.4 kb fragment in an homologously targeted gene. Abbreviations: H, HindIII; X, Xba I.

The GDF-8, we disrupted the GDF-8 gene was disrupted by homologous targeting in embryonic stem cells. To ensure that the resulting mice would be null for GDF-8 function, the entire mature C-terminal region was deleted and replaced by a neo cassette (FIG. 12a). A murine 129 SV/J genomic library was prepared in lambda FIX II according to the instructions provided by Stratagene (La Jolla, Calif.). The structure of the GDF-8 gene was deduced from restriction mapping and partial sequencing of phage clones isolated from this library. Vectors for preparing the targeting construct were kindly provided by Philip Soriano and Kirk Thomas University. R1 ES cells were transfected with the targeting construct, selected with gancyclovir (2 μM) and G418 (250 μg/ml), and analyzed by Southern analysis. Homologously targeted clones were injected into C57BL/6 blastocysts and transferred into pseudopregnant females. Germline transmission of the targeted allele was obtained in a total of 9 male chimeras from 5 independently-derived ES clones. Genomic Southern blots were hybridized at 42° C. as described above and washed in 0.2×SSC, 0.1% SDS at 42° C.

For whole leg analysis, legs of 14 week old mice were skinned, treated with 0.2 M EDTA in PBS at 4° C. for 4 weeks followed by 0.5 M sucrose in PBS at 4° C. For fiber number and size analysis, samples were directly mounted and frozen in isopentane as described (Brumback and Leech, *Color Atlas of Muscle Histochemistry*, pp. 9–33, PSG Publishing Company, Littleton, Mass., 1984). Ten to 30 μm sections were prepared using a cryostat and stained with hematoxylin and eosin. Muscle fiber numbers were determined from sections taken from the widest part of the tibialis cranialis muscle. Muscle fiber sizes were measured from photographs of sections of tibialis cranialis and gastrocnemius muscles. Fiber type analysis was carried out using the mysosin ATPase assay after pretreatment at pH 4.35 as described (Cumming, et al., *Color Atlas of Muscle Pathology*, pp. 184–185, 1994) and by immunohistochemistry using an antibody directed against type I myosin (MY32, Sigma) and the Vectastain method (Vector Labs); in the immunohistochemical experiments, no staining was seen when the primary antibodies were left out. Carcasses were prepared from shaved mice by removing the all of the internal organs and associated fat and connective tissue. Fat content of carcasses from 4 month old males was determined as described (Leshner, et al., *Physiol. Behavior*, 9:281, 1972).

For protein and DNA analysis, tissue was homogenized in 150 mM NaCl, 100 mM EDTA. Protein concentrations were determined using the Biorad protein assay. DNA was isolated by adding SDS to 1%, treating with 1 mg/ml proteinase K overnight at 55° C., extracting 3 times with phenol and twice with chloroform, and precipitating with ammonium acetate and EtOH. DNA was digested with 2 mg/ml RNase for 1 hour at 37° C., and following proteinase K digestion and phenol and chloroform extractions, the DNA was precipitated twice with ammonium acetate and EtOH.

Figure 12B:
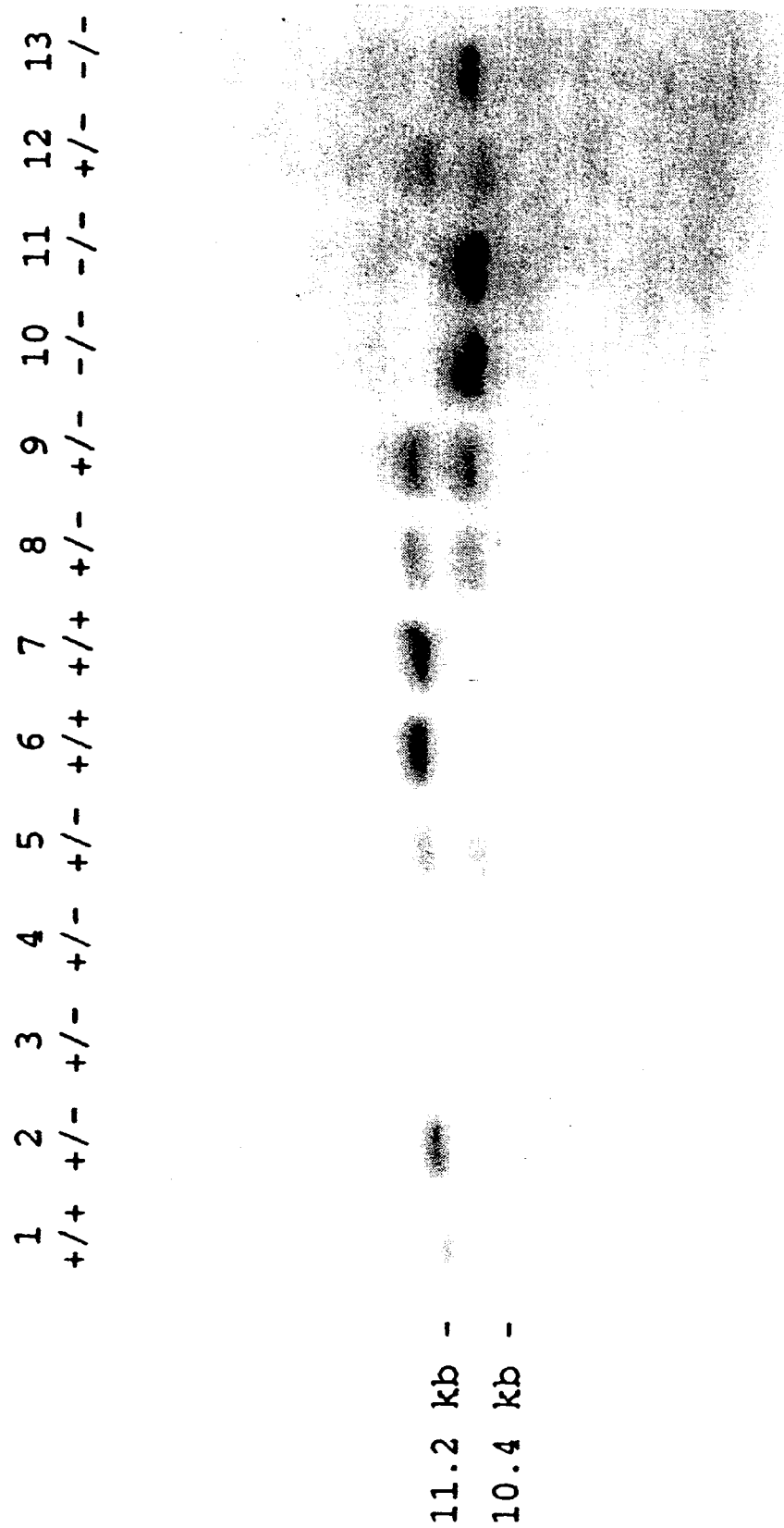
FIG. 12b shows a Southern blot analysis of offspring derived from a mating of heterozygous mutant mice. The lanes are as follows: DNA prepared from wild type 129 SV/J mice (lane 1), targeted embryonic stem cells (lane 2), F1 heterozygous mice (lanes 3 and 4), and offspring derived from a mating of these mice (lanes 5–13).

Homologous targeting of the GDF-8 gene was seen in 13/131 gancyclovir/G418 doubly-resistant ES cell clones. Following injection of these targeted clones into blastocysts, we obtained chimeras from 5 independently-derived ES clones that produced heterozygous pups when crossed to C57BL/6 females (FIG. 12b). Genotypic analysis of 678 offspring derived from crosses of F1 heterozygotes showed 170+/+(25%), 380+/−(56%), and 128−/−(19%). Although the ratio of genotypes was close to the expected ratio of 1:2:1, the smaller than expected number of homozygous mutants appeared to be statistically significant (p<0.001).

Homozygous mutants were viable and fertile when crossed to C57BL/6 mice and to each other. Homozygous mutant animals, however, were approximately 30% larger than their heterozygous and wild type littermates (Table 1). The difference between mutant and wild type body weights appeared to be relatively constant irrespective of age and sex in adult animals. Adult mutants also displayed an abnormal body shape, with pronounced shoulders and hips. When the skin was removed from animals that had been sacrificed, it was apparent that the muscles of the mutants were much larger than those of wild type animals. The increase in skeletal muscle mass appeared to be widespread throughout the body. Individual muscles isolated from homozygous mutant animals weighed approximately 2–3 times more than those isolated from wild type littermates (Table 2). Although the magnitude of the weight increase appeared to roughly correlate with the level of GDF-8 expression in the muscles examined. To determine whether the increased muscle mass could account for the entire difference in total body weights between wild type and mutant animals or whether many tissues were generally larger in the mutants, we compared the total body weights to carcass weights. As shown in Table 3, the difference in carcass weights between wild type and mutant animals was comparable to the difference in total body weights. Moreover, because the fat content of mutant and wild type animals was similar, these data are consistent with all of the total body weight difference resulting from an increase in skeletal muscle mass, although we have not formally ruled out the possibility that differences in bone mass might also contribute to the differences in total body mass.

Figure 13A:
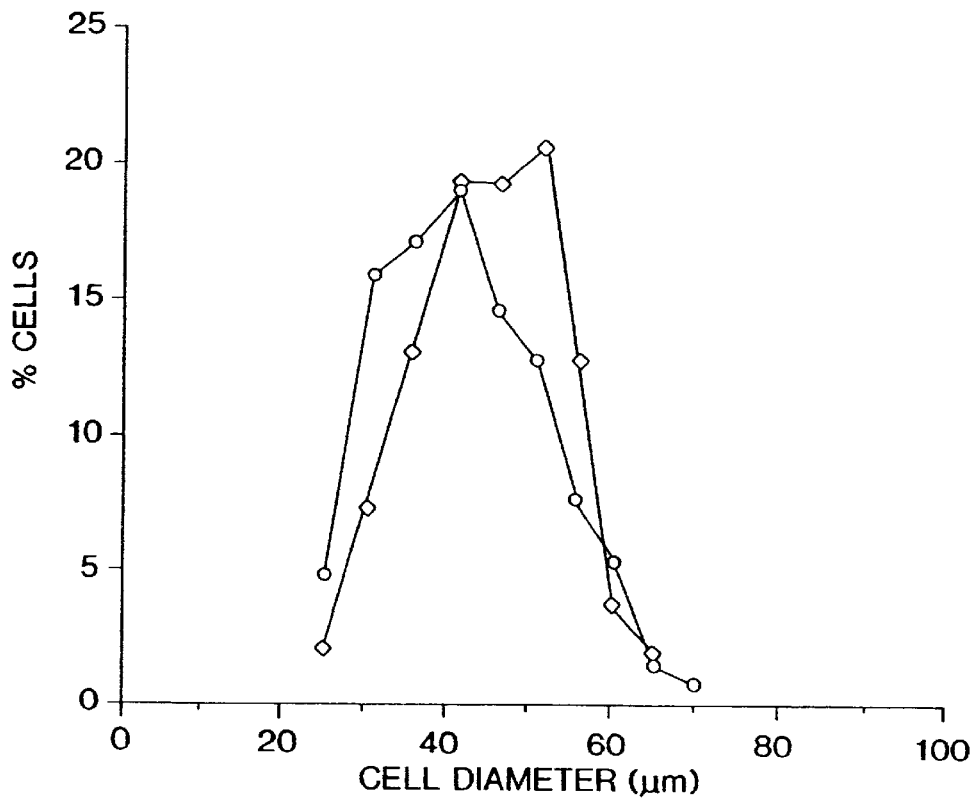
FIGS. 13a and 13b show the muscle fiber size distribution in mutant and wild type littermates.
Figure 13B:
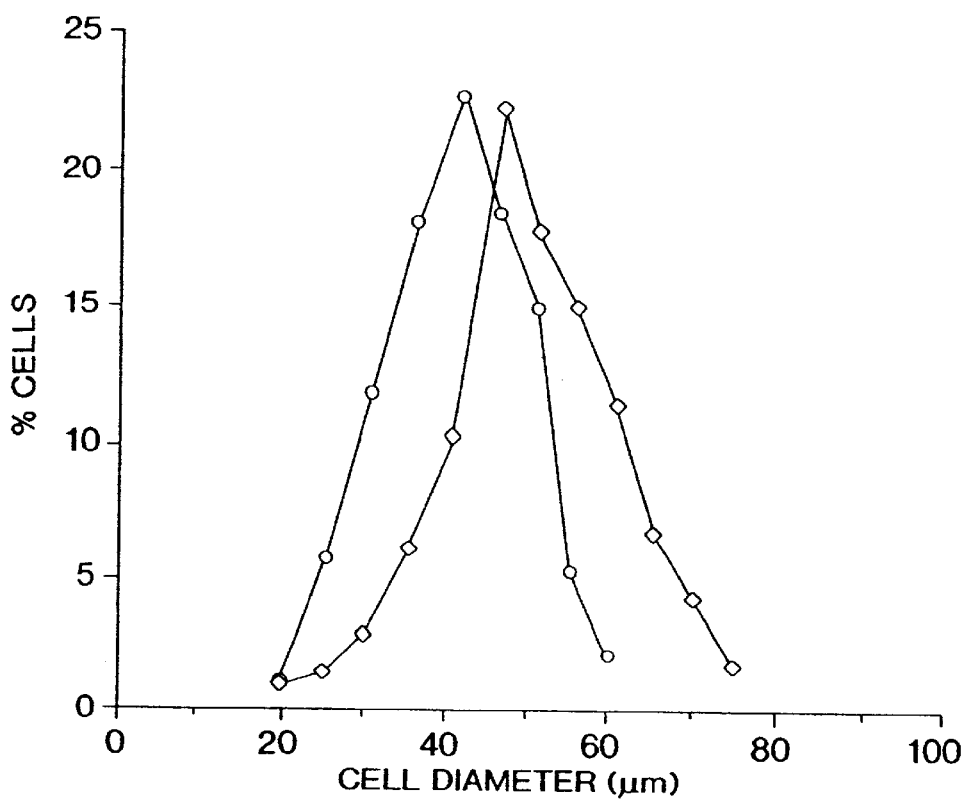

To determine whether the increase in skeletal muscle mass resulted from hyperplasia or from hypertrophy, histologic analysis of several different muscle groups was performed. The mutant muscle appeared grossly normal. No excess connective tissue or fat was seen nor were there any obvious signs of degeneration, such as widely varying fiber sizes (see below) or centrally-placed nuclei. Quantitation of the number of muscle fibers showed that at the widest portion of the tibialis cranialis muscle, the total cell number was 86% higher in mutant animals compared to wild type littermates [mutant =5470+/−121 (n=3), wild type =2936+/− 288 (n=3); p<0.01]. Consistent with this result was the finding that the amount of DNA extracted from mutant muscle was roughly 50% higher than from wild type muscle [mutant =350 jig (n=4), wild type=233 μg (n=3) from pooled gastrocnemius, plantaris, triceps brachii, tibialis cranialis, and pectoralis muscles; p=0.05]. Hence, a large part of the increase in skeletal muscle mass resulted from muscle cell hyperplasia. However, muscle fiber hypertrophy also appeared to contribute to the overall increase in muscle mass. As shown in FIG. 13, the mean fiber diameter of the tibialis cranialis muscle and gastrocnemius muscle was 7% and 22% larger, respectively, in mutant animals compared to wild type littermates, suggesting that the cross-sectional area of the fibers was increased by approximately 14% and 49%, respectively. Notably, although the mean fiber diameter was larger in the mutants, the standard deviation in fiber sizes was similar between mutant and wild type muscle, consistent with the absence of muscle degeneration in mutant animals. The increase in fiber size was also consistent with the finding that the protein to DNA ratio (w/w) was slightly increased in mutant compared to wild type muscle [mutant =871+/−111 (n=4), wild type =624+/−85 (n =3); p<0.05].

Table 4 shows a comparison between muscle weight (in grams) from wild-type (+/+), heterozygous (+/−) and a homozygous knock-out mice (−/−). The muscle mass is increased in heterozygous as compared to wild-type animals.

Finally, fiber type analysis of various muscles was carried out to determine whether the number of both type I (slow) and type II (fast) fibers was increased in the mutant animals. In most of the muscles examined, including the tibialis cranialis muscle, the vast majority of muscle fibers were type II in both mutant and wild type animals. Hence, based on the cell counts discussed above, the absolute number of type II fibers were increased in the tibialis cranialis muscle. In the soleus muscle, where the number of type I fibers was sufficiently high that we could attempt to quantitate the ratio of fiber types could be quantitated, the percent of type I fibers was decreased by approximately 33% in mutant compared to wild type muscle [wild type =39.2+/−8.1 (n =3), mutant =26.4+/−9.3 (n =4)]; however, the variability in this ratio for both wild type and mutant animals was too high to support any firm conclusions regarding the relative number of fiber types.

EXAMPLE 9

Isolation of Rat and Chicken GDF-8

In order to isolate rat and chicken GDF-8 cDNA clones, skeletal muscle cDNA libraries prepared from these species were obtained from Stratagene and screened with a murine GDF-8 probe. Library screening was carried out as described previously (Lee, Mol. Endocrinol., 4:1034–1040) except that final washes were carried out in 2×SSC at 65° C. Partial sequence analysis of hybridizing clones revealed the presence of open reading frames highly related to murine and human GDF-8. Partial sequences of rat and chicken GDF-8 are shown in FIGS. 2c and 2d, respectively, and an alignment of the predicated rat and chicken GDF-8 amino acid sequences with those of murine and human GDF-8 are shown in FIG. 3b. Full length rat and chicken GDF-8 is shown in FIGS. 14d and 14c, respectively and sequence alignment between murine, rat, human, baboon, porcine, ovine, bovine, chicken, and turkey sequences is shown in FIGS. 15a and 15b. All sequences contain an RSRR (SEQ ID NO: 51) sequence that is likely to represent the proteolytic processing site. Following this RSRR (SEQ ID NO: 51) sequence, the sequences contain a C-terminal region that is 100% conserved among all four species. The absolute conservation of the C-terminal region between species as evolutionarily far apart as humans and chickens, and baboons and turkeys, suggests that this region will be highly conserved in many other species as well. Similar methodology was used to obtain the nucleotide and amino acid sequences for baboon (SEQ ID NO:18 and 19, respectively; FIG. 14a); bovine (SEQ ID NO:20 and 21, respectively; FIG. 14b); turkey (SEQ ID NO:26 and 27, respectively; FIG. 14e); porcine (SEQ ID NO:28 and 29, respectively; FIG. 14f); and ovine (SEQ ID NO:30 and 31, respectively; FIG. 14g).

Although the invention has been described with reference to the presently preferred embodiment, it should be understood that various modifications can be made without departing from the spirit of the invention. Accordingly, the invention is limited only by the following claims.

---

What is claimed is:

1. A method for detecting a polynucleotide encoding growth differentiation factor-8 (GDF-8) in a sample, the method comprising:
   a) contacting the sample with an oligonucleotide probe that hybridizes specifically with a polynucleotide encoding GDF-8,
      wherein the oligonucleotide probe comprises at least about a 15 nucleotide portion of a nucleic acid molecule encoding a mammalian or avian GDF-8; and
   b) detecting specific hybridization of the oligonucleotide probe to a polynucleotide in the sample, wherein said specific hybridization is stable to washing in 2×SSC at 65° C., thereby detecting a polynucleotide encoding GDF-8 in the sample.

2. The method of claim 1, wherein the sample is selected from the group consisting of a tissue sample and a cell sample.

3. The method of claim 1, wherein the sample comprises muscle cells.

4. The method of claim 1, wherein the polynucleotide is a deoxyribonucleic acid (DNA) molecule.

5. The method of claim 4, wherein the DNA molecule is selected from the group consisting of genomic DNA and cDNA.

6. The method of claim 1, wherein the polynucleotide encoding GDF-8 is a ribonucleic acid molecule.

7. The method of claim 6, wherein the ribonucleic acid is mRNA.

8. The method of claim 1, wherein detecting specific binding is performed in vitro.

9. The method of claim 8, wherein the polynucleotide to be contacted with the oligonucleotide probe is immobilized on a filter.

10. The method of claim 1, wherein the sample is obtained from a mammal.

11. The method of claim 10, wherein the mammal is selected from the group consisting of a bovine, ovine and porcine mammal.

12. The method of claim 10, wherein the mammal is a human.

13. The method of claim 1, wherein the polynucleotide encoding GDF-8 comprises a polynucleotide encoding a GDF-8 polypeptide selected from the group of GDF-8 polypeptides set forth as SEQ ID NO: 12, SEQ ID NO: 14, SEQ ID NO: 19, SEQ ID NO: 21, SEQ ID NO: 23; SEQ ID NO: 25, SEQ ID NO: 27, SEQ ID NO: 29, and SEQ ID NO: 31.

14. The method of claim 1, wherein the polynucleotide encoding GDF-8 is selected from the group of polynucleotides set forth as SEQ ID NO: 11, SEQ ID NO: 13, SEQ ID NO: 18, SEQ ID NO: 20, SEQ ID NO: 22; SEQ ID NO: 24, SEQ ID NO: 26, SEQ ID NO: 28, and SEQ ID NO: 30.

15. The method of claim 1, wherein the polynucleotide encodes bovine GDF-8 polypeptide having an amino acid sequences as set forth in SEQ ID NO: 21.

16. The method of claim 1, wherein the polynucleotide encodes human GDF-8 polypeptide having an amino acid sequences as set forth in SEQ ID NO: 14.

17. The method of claim 1, wherein the oligonucleotide probe comprises at least about a 15 nucleotide portion of a nucleic acid molecule encoding a mammalian or avian GDF-8 polypeptide selected from the group of GDF-8 polypeptides set forth as SEQ ID NO: 12, SEQ ID NO: 14, SEQ ID NO: 19, SEQ ID NO: 21, SEQ ID NO: 23, SEQ ID NO: 25, SEQ ID NO: 27, SEQ ID NO: 29, and SEQ ID NO: 31.

18. The method of claim 1, wherein the oligonucleotide probe comprises at least about a 15 nucleotide portion of a nucleic acid molecule encoding a mammalian or avian GDF-8 polypeptide selected from the group of polynucleotides set forth as SEQ ID NO: 11, SEQ ID NO: 13, SEQ ID NO: 18, SEQ ID NO: 20, SEQ ID NO: 22, SEQ ID NO: 24, SEQ ID NO: 26, SEQ ID NO: 28, and SEQ ID NO: 30.

19. The method of claim 1, wherein the oligonucleotide probe comprises a sequence selected from the group of sequences set forth as SEQ ID NO: 15, SEQ ID NO: 16, and SEQ ID NO: 17.

20. The method of claim 1, wherein the polynucleotide encodes a variant GDF-8.

21. The method of claim 1, wherein the polynucleotide encodes a mutant GDF-8.

22. The method of claim 21, wherein the mutant GDF-8 is a truncated GDF-8.

23. The method of claim 1, wherein detecting specific hybridization of the oligonucleotide probe comprises autoradiographic visualization of the probe.

24. The method of claim 1, wherein the oligonucleotide probe comprises a primer of a polymerase chain reaction (PCR) primer pair, whereby detecting specific hybridization of the oligonucleotide probe comprises performing PCR for 40 cycles at 94° C. for 2 minutes, 60° C. for 1 minute, and 72° C. for 2 minutes.

25. The method of claim 24, wherein the PCR primer pair comprises SEQ ID NO: 15 and SEQ ID NO: 16.

26. The method of claim 1, further comprising measuring an amount of the polynucleotide encoding a GDF-8 polypeptide in the sample.

27. A method for detecting a polynucleotide encoding growth differentiation factor-8 (GDF-8) in a sample, the method comprising:
  a) contacting the sample with an oligonucleotide probe that hybridizes specifically with a polynucleotide encoding GDF-8,
    wherein the oligonucleotide probe comprises at least about a 15 nucleotide portion of a nucleic acid molecule encoding a mammalian or avian GDF-8, and
    wherein the oligonucleotide probe comprises a primer of a polymerase chain reaction (PCR) primer pair comprising a forward primer and a reverse primer; and
  b) detecting specific hybridization of the oligonucleotide probe to a polynucleotide in the sample by performing PCR for 40 cycles at 94° C. for 2 minutes, 60° C. for 1 minute, and 72° C. for 2 minutes, thereby detecting a polynucleotide encoding GDF-8 in the sample.

28. The method of claim 27, wherein the PCR primer pair comprises SEQ ID NO: 15 and SEQ ID NO: 16.

29. The method of claim 27, wherein the sample is obtained from a mammal.

30. The method of claim 29, wherein the mammal is selected from the group consisting of a bovine, ovine and porcine mammal.

31. The method of claim 29, wherein the mammal is a human.

32. The method of claim 1 wherein the sample is obtained from an avian species or a piscine species.

33. The method of claim 27 wherein the sample is obtained from an avian species or a piscine species.

* * * * *

SEQUENCE LISTING

```
<160> NUMBER OF SEQ ID NOS:  51

<210> SEQ ID NO 1
<211> LENGTH: 35
<212> TYPE: DNA
<213> ORGANISM: Artificial Sequence
<220> FEATURE:
<223> OTHER INFORMATION: oligonucleotide for PCR
<221> NAME/KEY: misc_feature
<222> LOCATION: 12,27,30,33
<223> OTHER INFORMATION: n = inosine
<221> NAME/KEY: misc_feature
<222> LOCATION: (0)...(0)
<223> OTHER INFORMATION: n = A, T, G, or C;  v = A, G, or C, not T;
      r = G or A;  y = T or C;  k = T or G

<400> SEQUENCE: 1
ccggaattcg gntggvanra ytggrtnrtn kcncc                              35

<210> SEQ ID NO 2
<211> LENGTH: 33
<212> TYPE: DNA
<213> ORGANISM: Artificial Sequence
<220> FEATURE:
<223> OTHER INFORMATION: oligonucleotide for PCR
<221> NAME/KEY: misc_feature
<222> LOCATION: 13,25,28
<223> OTHER INFORMATION: n = inosine
<221> NAME/KEY: misc_feature
<222> LOCATION: (0)...(0)
<223> OTHER INFORMATION: n = A, T, G, or C;  r = A or G;  y = C or T;
      s = G or C

<400> SEQUENCE: 2
ccggaattcr canscrcarc tntcnacnry cat                                33

<210> SEQ ID NO 3
```

-continued

```
<211> LENGTH: 31
<212> TYPE: DNA
<213> ORGANISM: Artificial Sequence
<220> FEATURE:
<223> OTHER INFORMATION: oligonucleotide for PCR

<400> SEQUENCE: 3
cgcggatcca gagtcaaggt gacagacaca c                                31

<210> SEQ ID NO 4
<211> LENGTH: 33
<212> TYPE: DNA
<213> ORGANISM: Artificial Sequence
<220> FEATURE:
<223> OTHER INFORMATION: oligonucleotide for PCR

<400> SEQUENCE: 4
cgcggatcct cctcatgagc acccacagcg gtc                              33

<210> SEQ ID NO 5
<211> LENGTH: 550
<212> TYPE: DNA
<213> ORGANISM: Mus musculus
<220> FEATURE:
<221> NAME/KEY: CDS
<222> LOCATION: (59)...(436)

<400> SEQUENCE: 5
ttaaggtagg aaggatttca ggctctattt acataattgt tctttccttt tcacacag     58 aat ccc ttt tta gaa gtc aag gtg aca gac aca ccc aag agg tcc cgg   106
Asn Pro Phe Leu Glu Val Lys Val Thr Asp Thr Pro Lys Arg Ser Arg
 1               5                  10                  15 aga gac ttt ggg ctt gac tgc gat gag cac tcc acg gaa tcc cgg tgc   154
Arg Asp Phe Gly Leu Asp Cys Asp Glu His Ser Thr Glu Ser Arg Cys
             20                  25                  30 tgc cgc tac ccc ctc acg gtc gat ttt gaa gcc ttt gga tgg gac tgg   202
Cys Arg Tyr Pro Leu Thr Val Asp Phe Glu Ala Phe Gly Trp Asp Trp
         35                  40                  45 att atc gca ccc aaa aga tat aag gcc aat tac tgc tca gga gag tgt   250
Ile Ile Ala Pro Lys Arg Tyr Lys Ala Asn Tyr Cys Ser Gly Glu Cys
     50                  55                  60 gaa ttt gtg ttt tta caa aaa tat ccg cat act cat ctt gtg cac caa   298
Glu Phe Val Phe Leu Gln Lys Tyr Pro His Thr His Leu Val His Gln
 65                  70                  75                  80 gca aac ccc aga ggc tca gca ggc cct tgc tgc act ccg aca aaa atg   346
Ala Asn Pro Arg Gly Ser Ala Gly Pro Cys Cys Thr Pro Thr Lys Met
                 85                  90                  95 tct ccc att aat atg cta tat ttt aat ggc aaa gaa caa ata ata tat   394
Ser Pro Ile Asn Met Leu Tyr Phe Asn Gly Lys Glu Gln Ile Ile Tyr
            100                 105                 110 ggg aaa att cca gcc atg gta gta gac cgc tgt ggg tgc tca             436
Gly Lys Ile Pro Ala Met Val Val Asp Arg Cys Gly Cys Ser
            115                 120                 125 tgagctttgc attaggttag aaacttccca agtcatggaa ggtcttcccc tcaatttcga   496
aactgtgaat tcctgcagcc cgggggatcc actagttcta gagcggccgc cacc         550

<210> SEQ ID NO 6
<211> LENGTH: 126
<212> TYPE: PRT
<213> ORGANISM: Mus musculus

<400> SEQUENCE: 6
```

-continued

```
Asn Pro Phe Leu Glu Val Lys Val Thr Asp Thr Pro Lys Arg Ser Arg
 1               5                  10                  15

Arg Asp Phe Gly Leu Asp Cys Asp Glu His Ser Thr Glu Ser Arg Cys
                20                  25                  30

Cys Arg Tyr Pro Leu Thr Val Asp Phe Glu Ala Phe Gly Trp Asp Trp
            35                  40                  45

Ile Ile Ala Pro Lys Arg Tyr Lys Ala Asn Tyr Cys Ser Gly Glu Cys
     50                  55                  60

Glu Phe Val Phe Leu Gln Lys Tyr Pro His Thr His Leu Val His Gln
65                  70                  75                  80

Ala Asn Pro Arg Gly Ser Ala Gly Pro Cys Cys Thr Pro Thr Lys Met
                85                  90                  95

Ser Pro Ile Asn Met Leu Tyr Phe Asn Gly Lys Glu Gln Ile Ile Tyr
            100                 105                 110

Gly Lys Ile Pro Ala Met Val Val Asp Arg Cys Gly Cys Ser
        115                 120                 125
```

<210> SEQ ID NO 7
<211> LENGTH: 326
<212> TYPE: DNA
<213> ORGANISM: Homo sapiens
<220> FEATURE:
<221> NAME/KEY: CDS
<222> LOCATION: (3)...(326)

<400> SEQUENCE: 7

```
ca aaa aga tcc aga agg gat ttt ggt ctt gac tgt gat gag cac tca       47
   Lys Arg Ser Arg Arg Asp Phe Gly Leu Asp Cys Asp Glu His Ser
    1               5                  10                  15 aca gaa tca cga tgc tgt cgt tac cct cta act gtg gat ttt gaa gct      95
Thr Glu Ser Arg Cys Cys Arg Tyr Pro Leu Thr Val Asp Phe Glu Ala
                20                  25                  30 ttt gga tgg gat tgg att atc gct cct aaa aga tat aag gcc aat tac     143
Phe Gly Trp Asp Trp Ile Ile Ala Pro Lys Arg Tyr Lys Ala Asn Tyr
            35                  40                  45 tgc tct gga gag tgt gaa ttt gta ttt tta caa aaa tat cct cat act     191
Cys Ser Gly Glu Cys Glu Phe Val Phe Leu Gln Lys Tyr Pro His Thr
     50                  55                  60 cat ctg gta cac caa gca aac ccc aga ggt tca gca ggc cct tgc tgt     239
His Leu Val His Gln Ala Asn Pro Arg Gly Ser Ala Gly Pro Cys Cys
65                  70                  75 act ccc aca aag atg tct cca att aat atg cta tat ttt aat ggc aaa     287
Thr Pro Thr Lys Met Ser Pro Ile Asn Met Leu Tyr Phe Asn Gly Lys
80                  85                  90                  95 gaa caa ata ata tat ggg aaa att cca gcg atg gta gta                 326
Glu Gln Ile Ile Tyr Gly Lys Ile Pro Ala Met Val Val
                100                 105
```

<210> SEQ ID NO 8
<211> LENGTH: 108
<212> TYPE: PRT
<213> ORGANISM: Homo sapiens

<400> SEQUENCE: 8

```
Lys Arg Ser Arg Arg Asp Phe Gly Leu Asp Cys Asp Glu His Ser Thr
 1               5                  10                  15

Glu Ser Arg Cys Cys Arg Tyr Pro Leu Thr Val Asp Phe Glu Ala Phe
                20                  25                  30

Gly Trp Asp Trp Ile Ile Ala Pro Lys Arg Tyr Lys Ala Asn Tyr Cys
            35                  40                  45
```

```
Ser Gly Glu Cys Glu Phe Val Phe Leu Gln Lys Tyr Pro His Thr His
    50                  55                  60
Leu Val His Gln Ala Asn Pro Arg Gly Ser Ala Gly Pro Cys Cys Thr
65                  70                  75                  80
Pro Thr Lys Met Ser Pro Ile Asn Met Leu Tyr Phe Asn Gly Lys Glu
                85                  90                  95
Gln Ile Ile Tyr Gly Lys Ile Pro Ala Met Val Val
            100                 105

<210> SEQ ID NO 9
<211> LENGTH: 9
<212> TYPE: PRT
<213> ORGANISM: Artificial Sequence
<220> FEATURE:
<223> OTHER INFORMATION: amino acid encoded by oligonucleotide for PCR
<221> NAME/KEY: VARIANT
<222> LOCATION: 3
<223> OTHER INFORMATION: Xaa = His, Gln, Asn, Lys, Asp, Glu
<221> NAME/KEY: VARIANT
<222> LOCATION: 4
<223> OTHER INFORMATION: Xaa = Asp, Asn
<221> NAME/KEY: VARIANT
<222> LOCATION: 6, 7
<223> OTHER INFORMATION: Xaa = Val, Ile, Met
<221> NAME/KEY: VARIANT
<222> LOCATION: 8
<223> OTHER INFORMATION: Xaa = Ala, Ser

<400> SEQUENCE: 9

Gly Trp Xaa Xaa Trp Xaa Xaa Xaa Pro
1               5

<210> SEQ ID NO 10
<211> LENGTH: 8
<212> TYPE: PRT
<213> ORGANISM: Artificial Sequence
<220> FEATURE:
<223> OTHER INFORMATION: amino acid encoded by oligonucleotide for PCR
<221> NAME/KEY: VARIANT
<222> LOCATION: 2
<223> OTHER INFORMATION: Xaa = Val, Ile, Met, Thr, Ala
<221> NAME/KEY: VARIANT
<222> LOCATION: 4
<223> OTHER INFORMATION: Xaa = Asp, Glu
<221> NAME/KEY: VARIANT
<222> LOCATION: 7
<223> OTHER INFORMATION: Xaa = Gly, Ala

<400> SEQUENCE: 10

Met Xaa Val Xaa Ser Cys Xaa Cys
1               5

<210> SEQ ID NO 11
<211> LENGTH: 2676
<212> TYPE: DNA
<213> ORGANISM: Mus musculus
<220> FEATURE:
<221> NAME/KEY: CDS
<222> LOCATION: (104)...(1231)

<400> SEQUENCE: 11
gtctctcgga cggtacatgc actaatattt cacttggcat tactcaaaag caaaagaag      60 aaataagaac aagggaaaaa aaaagattgt gctgattttt aaa atg atg caa aaa     115
                                              Met Met Gln Lys
                                                1 ctg caa atg tat gtt tat att tac ctg ttc atg ctg att gct gct ggc     163
Leu Gln Met Tyr Val Tyr Ile Tyr Leu Phe Met Leu Ile Ala Ala Gly
```

-continued

| | 5 | | | 10 | | | 15 | | | 20 | | |
|---|---|---|---|---|---|---|---|---|---|---|---|---|

| cca | gtg | gat | cta | aat | gag | ggc | agt | gag | aga | gaa | gaa | aat | gtg | gaa | aaa | 211 |
| Pro | Val | Asp | Leu | Asn | Glu | Gly | Ser | Glu | Arg | Glu | Glu | Asn | Val | Glu | Lys | |
| | | | 25 | | | | | 30 | | | | | 35 | | | |

| gag | ggg | ctg | tgt | aat | gca | tgt | gcg | tgg | aga | caa | aac | acg | agg | tac | tcc | 259 |
| Glu | Gly | Leu | Cys | Asn | Ala | Cys | Ala | Trp | Arg | Gln | Asn | Thr | Arg | Tyr | Ser | |
| | | | 40 | | | | | 45 | | | | | 50 | | | |

| aga | ata | gaa | gcc | ata | aaa | att | caa | atc | ctc | agt | aag | ctg | cgc | ctg | gaa | 307 |
| Arg | Ile | Glu | Ala | Ile | Lys | Ile | Gln | Ile | Leu | Ser | Lys | Leu | Arg | Leu | Glu | |
| | | 55 | | | | | 60 | | | | | 65 | | | | |

| aca | gct | cct | aac | atc | agc | aaa | gat | gct | ata | aga | caa | ctt | ctg | cca | aga | 355 |
| Thr | Ala | Pro | Asn | Ile | Ser | Lys | Asp | Ala | Ile | Arg | Gln | Leu | Leu | Pro | Arg | |
| | 70 | | | | | 75 | | | | | 80 | | | | | |

| gcg | cct | cca | ctc | cgg | gaa | ctg | atc | gat | cag | tac | gac | gtc | cag | agg | gat | 403 |
| Ala | Pro | Pro | Leu | Arg | Glu | Leu | Ile | Asp | Gln | Tyr | Asp | Val | Gln | Arg | Asp | |
| 85 | | | | | 90 | | | | | 95 | | | | | 100 | |

| gac | agc | agt | gat | ggc | tct | ttg | gaa | gat | gac | gat | tat | cac | gct | acc | acg | 451 |
| Asp | Ser | Ser | Asp | Gly | Ser | Leu | Glu | Asp | Asp | Asp | Tyr | His | Ala | Thr | Thr | |
| | | | | 105 | | | | | 110 | | | | | 115 | | |

| gaa | aca | atc | att | acc | atg | cct | aca | gag | tct | gac | ttt | cta | atg | caa | gcg | 499 |
| Glu | Thr | Ile | Ile | Thr | Met | Pro | Thr | Glu | Ser | Asp | Phe | Leu | Met | Gln | Ala | |
| | | | 120 | | | | | 125 | | | | | 130 | | | |

| gat | ggc | aag | ccc | aaa | tgt | tgc | ttt | ttt | aaa | ttt | agc | tct | aaa | ata | cag | 547 |
| Asp | Gly | Lys | Pro | Lys | Cys | Cys | Phe | Phe | Lys | Phe | Ser | Ser | Lys | Ile | Gln | |
| | | 135 | | | | | 140 | | | | | 145 | | | | |

| tac | aac | aaa | gta | gta | aaa | gcc | caa | ctg | tgg | ata | tat | ctc | aga | ccc | gtc | 595 |
| Tyr | Asn | Lys | Val | Val | Lys | Ala | Gln | Leu | Trp | Ile | Tyr | Leu | Arg | Pro | Val | |
| | 150 | | | | | 155 | | | | | 160 | | | | | |

| aag | act | cct | aca | aca | gtg | ttt | gtg | caa | atc | ctg | aga | ctc | atc | aaa | ccc | 643 |
| Lys | Thr | Pro | Thr | Thr | Val | Phe | Val | Gln | Ile | Leu | Arg | Leu | Ile | Lys | Pro | |
| 165 | | | | | 170 | | | | | 175 | | | | | 180 | |

| atg | aaa | gac | ggt | aca | agg | tat | act | gga | atc | cga | tct | ctg | aaa | ctt | gac | 691 |
| Met | Lys | Asp | Gly | Thr | Arg | Tyr | Thr | Gly | Ile | Arg | Ser | Leu | Lys | Leu | Asp | |
| | | | | 185 | | | | | 190 | | | | | 195 | | |

| atg | agc | cca | ggc | act | ggt | att | tgg | cag | agt | att | gat | gtg | aag | aca | gtg | 739 |
| Met | Ser | Pro | Gly | Thr | Gly | Ile | Trp | Gln | Ser | Ile | Asp | Val | Lys | Thr | Val | |
| | | | 200 | | | | | 205 | | | | | 210 | | | |

| ttg | caa | aat | tgg | ctc | aaa | cag | cct | gaa | tcc | aac | tta | ggc | att | gaa | atc | 787 |
| Leu | Gln | Asn | Trp | Leu | Lys | Gln | Pro | Glu | Ser | Asn | Leu | Gly | Ile | Glu | Ile | |
| | | 215 | | | | | 220 | | | | | 225 | | | | |

| aaa | gct | ttg | gat | gag | aat | ggc | cat | gat | ctt | gct | gta | acc | ttc | cca | gga | 835 |
| Lys | Ala | Leu | Asp | Glu | Asn | Gly | His | Asp | Leu | Ala | Val | Thr | Phe | Pro | Gly | |
| | 230 | | | | | 235 | | | | | 240 | | | | | |

| cca | gga | gaa | gat | ggg | ctg | aat | ccc | ttt | tta | gaa | gtc | aag | gtg | aca | gac | 883 |
| Pro | Gly | Glu | Asp | Gly | Leu | Asn | Pro | Phe | Leu | Glu | Val | Lys | Val | Thr | Asp | |
| 245 | | | | | 250 | | | | | 255 | | | | | 260 | |

| aca | ccc | aag | agg | tcc | cgg | aga | gac | ttt | ggg | ctt | gac | tgc | gat | gag | cac | 931 |
| Thr | Pro | Lys | Arg | Ser | Arg | Arg | Asp | Phe | Gly | Leu | Asp | Cys | Asp | Glu | His | |
| | | | | 265 | | | | | 270 | | | | | 275 | | |

| tcc | acg | gaa | tcc | cgg | tgc | tgc | cgc | tac | ccc | ctc | acg | gtc | gat | ttt | gaa | 979 |
| Ser | Thr | Glu | Ser | Arg | Cys | Cys | Arg | Tyr | Pro | Leu | Thr | Val | Asp | Phe | Glu | |
| | | | 280 | | | | | 285 | | | | | 290 | | | |

| gcc | ttt | gga | tgg | gac | tgg | att | atc | gca | ccc | aaa | aga | tat | aag | gcc | aat | 1027 |
| Ala | Phe | Gly | Trp | Asp | Trp | Ile | Ile | Ala | Pro | Lys | Arg | Tyr | Lys | Ala | Asn | |
| | | 295 | | | | | 300 | | | | | 305 | | | | |

| tac | tgc | tca | gga | gag | tgt | gaa | ttt | gtg | ttt | tta | caa | aaa | tat | ccg | cat | 1075 |
| Tyr | Cys | Ser | Gly | Glu | Cys | Glu | Phe | Val | Phe | Leu | Gln | Lys | Tyr | Pro | His | |
| | 310 | | | | | 315 | | | | | 320 | | | | | |

| act | cat | ctt | gtg | cac | caa | gca | aac | ccc | aga | ggc | tca | gca | ggc | cct | tgc | 1123 |

```
                Thr His Leu Val His Gln Ala Asn Pro Arg Gly Ser Ala Gly Pro Cys
                325                 330                 335                 340 tgc act ccg aca aaa atg tct ccc att aat atg cta tat ttt aat ggc           1171
Cys Thr Pro Thr Lys Met Ser Pro Ile Asn Met Leu Tyr Phe Asn Gly
                    345                 350                 355 aaa gaa caa ata ata tat ggg aaa att cca gcc atg gta gta gac cgc           1219
Lys Glu Gln Ile Ile Tyr Gly Lys Ile Pro Ala Met Val Val Asp Arg
                360                 365                 370 tgt ggg tgc tca tgagctttgc attaggttag aaacttccca agtcatggaa              1271
Cys Gly Cys Ser
        375 ggtcttcccc tcaatttcga aactgtgaat tcaagcacca caggctgtag gccttgagta        1331
tgctctagta acgtaagcac aagctacagt gtatgaacta aaagagagaa tagatgcaat        1391
ggttggcatt caaccaccaa aataaaccat actataggat gttgtatgat ttccagagtt        1451
tttgaaatag atggagatca aattacattt atgtccatat atgtatatta caactacaat        1511
ctaggcaagg aagtgagagc acatcttgtg gtctgctgag ttaggagggt atgattaaaa        1571
ggtaaagtct tatttcctaa cagtttcact taatatttac agaagaatct atatgtagcc        1631
tttgtaaagt gtaggattgt tatcatttaa aaacatcatg tacacttata tttgtattgt        1691
atacttggta agataaaatt ccacaaagta ggaatggggc ctcacataca cattgccatt        1751
cctattataa ttggacaatc caccacggtg ctaatgcagt gctgaatggc tcctactgga        1811
cctctcgata gaacactcta caaagtacga gtctctctct cccttccagg tgcatctcca        1871
cacacacagc actaagtgtt caatgcattt tctttaagga agaagaatc ttttttttcta        1931
gaggtcaact ttcagtcaac tctagcacag cgggagtgac tgctgcatct taaaaggcag        1991
ccaaacagta ttcatttttt aatctaaatt tcaaaatcac tgtctgcctt tatcacatgg        2051
caattttgtg gtaaaataat ggaaatgact ggttctatca atattgtata aaagactctg        2111
aaacaattac atttatataa tatgtataca atattgtttt gtaaataagt gtctcctttt        2171
atatttactt tggtatattt ttacactaat gaaatttcaa atcattaaag tacaaagaca        2231
tgtcatgtat cacaaaaaag gtgactgctt ctatttcaga gtgaattagc agattcaata        2291
gtggtcttaa aactctgtat gttaagatta gaaggttata ttacaatcaa tttatgtatt        2351
ttttacatta tcaacttatg gtttcatggt ggctgtatct atgaatgtgg ctcccagtca        2411
aatttcaatg ccccaccatt ttaaaaatta caagcattac taaacatacc aacatgtatc        2471
taaagaaata caaatatggt atctcaataa cagctacttt tttattttat aatttgacaa        2531
tgaatacatt tcttttattt acttcagttt tataaattgg aactttgttt atcaaatgta        2591
ttgtactcat agctaaatga aattatttct tacataaaaa tgtgtagaaa ctataaatta        2651
aagtgttttc acattttga aaggc                                               2676

<210> SEQ ID NO 12
<211> LENGTH: 376
<212> TYPE: PRT
<213> ORGANISM: Mus musculus

<400> SEQUENCE: 12

Met Met Gln Lys Leu Gln Met Tyr Val Tyr Ile Tyr Leu Phe Met Leu
1               5                   10                  15

Ile Ala Ala Gly Pro Val Asp Leu Asn Glu Gly Ser Glu Arg Glu Glu
            20                  25                  30

Asn Val Glu Lys Glu Gly Leu Cys Asn Ala Cys Ala Trp Arg Gln Asn
        35                  40                  45
```

```
Thr Arg Tyr Ser Arg Ile Glu Ala Ile Lys Ile Gln Ile Leu Ser Lys
    50                  55                  60

Leu Arg Leu Glu Thr Ala Pro Asn Ile Ser Lys Asp Ala Ile Arg Gln
 65                  70                  75                  80

Leu Leu Pro Arg Ala Pro Pro Leu Arg Glu Leu Ile Asp Gln Tyr Asp
                 85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
                180                 185                 190

Leu Lys Leu Asp Met Ser Pro Gly Thr Gly Ile Trp Gln Ser Ile Asp
            195                 200                 205

Val Lys Thr Val Leu Gln Asn Trp Leu Lys Gln Pro Glu Ser Asn Leu
210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
                260                 265                 270

Cys Asp Glu His Ser Thr Glu Ser Arg Cys Cys Arg Tyr Pro Leu Thr
            275                 280                 285

Val Asp Phe Glu Ala Phe Gly Trp Asp Trp Ile Ile Ala Pro Lys Arg
290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
370                 375

<210> SEQ ID NO 13
<211> LENGTH: 2743
<212> TYPE: DNA
<213> ORGANISM: Homo sapiens
<220> FEATURE:
<221> NAME/KEY: CDS
<222> LOCATION: (59)...(1183)

<400> SEQUENCE: 13
aagaaaagta aaaggaagaa acaagaacaa gaaaaaagat tatattgatt ttaaaatc        58 atg caa aaa ctg caa ctc tgt gtt tat att tac ctg ttt atg ctg att       106
Met Gln Lys Leu Gln Leu Cys Val Tyr Ile Tyr Leu Phe Met Leu Ile
```

```
                                                         -continued 1               5                   10                  15
gtt gct ggt cca gtg gat cta aat gag aac agt gag caa aaa gaa aat       154
Val Ala Gly Pro Val Asp Leu Asn Glu Asn Ser Glu Gln Lys Glu Asn
                20                  25                  30 gtg gaa aaa gag ggg ctg tgt aat gca tgt act tgg aga caa aac act       202
Val Glu Lys Glu Gly Leu Cys Asn Ala Cys Thr Trp Arg Gln Asn Thr
            35                  40                  45 aaa tct tca aga ata gaa gcc att aag ata caa atc ctc agt aaa ctt       250
Lys Ser Ser Arg Ile Glu Ala Ile Lys Ile Gln Ile Leu Ser Lys Leu
        50                  55                  60 cgt ctg gaa aca gct cct aac atc agc aaa gat gtt ata aga caa ctt       298
Arg Leu Glu Thr Ala Pro Asn Ile Ser Lys Asp Val Ile Arg Gln Leu
    65                  70                  75                  80 tta ccc aaa gct cct cca ctc cgg gaa ctg att gat cag tat gat gtc       346
Leu Pro Lys Ala Pro Pro Leu Arg Glu Leu Ile Asp Gln Tyr Asp Val
                85                  90                  95 cag agg gat gac agc agc gat ggc tct ttg gaa gat gac gat tat cac       394
Gln Arg Asp Asp Ser Ser Asp Gly Ser Leu Glu Asp Asp Asp Tyr His
                100                 105                 110 gct aca acg gaa aca atc att acc atg cct aca gag tct gat ttt cta       442
Ala Thr Thr Glu Thr Ile Ile Thr Met Pro Thr Glu Ser Asp Phe Leu
        115                 120                 125 atg caa gtg gat gga aaa ccc aaa tgt tgc ttc ttt aaa ttt agc tct       490
Met Gln Val Asp Gly Lys Pro Lys Cys Cys Phe Phe Lys Phe Ser Ser
    130                 135                 140 aaa ata caa tac aat aaa gta gta aag gcc caa cta tgg ata tat ttg       538
Lys Ile Gln Tyr Asn Lys Val Val Lys Ala Gln Leu Trp Ile Tyr Leu
145                 150                 155                 160 aga ccc gtc gag act cct aca aca gtg ttt gtg caa atc ctg aga ctc       586
Arg Pro Val Glu Thr Pro Thr Thr Val Phe Val Gln Ile Leu Arg Leu
                165                 170                 175 atc aaa cct atg aaa gac ggt aca agg tat act gga atc cga tct ctg       634
Ile Lys Pro Met Lys Asp Gly Thr Arg Tyr Thr Gly Ile Arg Ser Leu
            180                 185                 190 aaa ctt gac atg aac cca ggc act ggt att tgg cag agc att gat gtg       682
Lys Leu Asp Met Asn Pro Gly Thr Gly Ile Trp Gln Ser Ile Asp Val
        195                 200                 205 aag aca gtg ttg caa aat tgg ctc aaa caa cct gaa tcc aac tta ggc       730
Lys Thr Val Leu Gln Asn Trp Leu Lys Gln Pro Glu Ser Asn Leu Gly
    210                 215                 220 att gaa ata aaa gct tta gat gag aat ggt cat gat ctt gct gta acc       778
Ile Glu Ile Lys Ala Leu Asp Glu Asn Gly His Asp Leu Ala Val Thr
225                 230                 235                 240 ttc cca gga cca gga gaa gat ggg ctg aat ccg ttt tta gag gtc aag       826
Phe Pro Gly Pro Gly Glu Asp Gly Leu Asn Pro Phe Leu Glu Val Lys
                245                 250                 255 gta aca gac aca cca aaa aga tcc aga agg gat ttt ggt ctt gac tgt       874
Val Thr Asp Thr Pro Lys Arg Ser Arg Arg Asp Phe Gly Leu Asp Cys
            260                 265                 270 gat gag cac tca aca gaa tca cga tgc tgt cgt tac cct cta act gtg       922
Asp Glu His Ser Thr Glu Ser Arg Cys Cys Arg Tyr Pro Leu Thr Val
        275                 280                 285 gat ttt gaa gct ttt gga tgg gat tgg att atc gct cct aaa aga tat       970
Asp Phe Glu Ala Phe Gly Trp Asp Trp Ile Ile Ala Pro Lys Arg Tyr
    290                 295                 300 aag gcc aat tac tgc tct gga gag tgt gaa ttt gta ttt tta caa aaa      1018
Lys Ala Asn Tyr Cys Ser Gly Glu Cys Glu Phe Val Phe Leu Gln Lys
305                 310                 315                 320 tat cct cat act cat ctg gta cac caa gca aac ccc aga ggt tca gca      1066
```

```
Tyr Pro His Thr His Leu Val His Gln Ala Asn Pro Arg Gly Ser Ala
            325                 330                 335 ggc cct tgc tgt act ccc aca aag atg tct cca att aat atg cta tat     1114
Gly Pro Cys Cys Thr Pro Thr Lys Met Ser Pro Ile Asn Met Leu Tyr
        340                 345                 350 ttt aat ggc aaa gaa caa ata ata tat ggg aaa att cca gcg atg gta     1162
Phe Asn Gly Lys Glu Gln Ile Ile Tyr Gly Lys Ile Pro Ala Met Val
    355                 360                 365 gta gac cgc tgt ggg tgc tca tgagatttat attaagcgtt cataacttcc        1213
Val Asp Arg Cys Gly Cys Ser
    370             375 taaaacatgg aagttttcc cctcaacaat tttgaagctg tgaaattaag taccacaggc    1273
tataggccta gagtatgcta cagtcactta agcataagct acagtatgta aactaaaagg   1333
gggaatatat gcaatggttg gcatttaacc atccaaacaa atcatacaag aaagttttat   1393
gatttccaga gttttttgagc tagaaggaga tcaaattaca tttatgttcc tatatattac  1453
aacatcggcg aggaaatgaa agcgattctc cttgagttct gatgaattaa aggagtatgc   1513
tttaaagtct atttctttaa agttttgttt aatatttaca gaaaaatcca catacagtat   1573
tggtaaaatg caggattgtt ataccatc attcgaatca tccttaaaca cttgaattta    1633
tattgtatgg tagtatactt ggtaagataa aattccacaa aaatagggat ggtgcagcat   1693
atgcaatttc cattcctatt ataattgaca cagtacatta acaatccatg ccaacggtgc   1753
taatacgata ggctgaatgt ctgaggctac caggtttatc acataaaaaa cattcagtaa   1813
aatagtaagt ttctcttttc ttcaggtgca ttttcctaca cctccaaatg aggaatggat   1873 tttcttaat gtaagaagaa tcattttct agaggttggc tttcaattct gtagcatact    1933
tggagaaact gcattatctt aaaaggcagt caaatggtgt ttgttttat caaaatgtca   1993 aaataacata cttggagaag tatgtaattt tgtctttgga aaattacaac actgcctttg   2053
caacactgca gttttatgg taaataata gaaatgatcg actctatcaa tattgtataa    2113
aaagactgaa acaatgcatt tatataatat gtatacaata ttgttttgta ataagtgtc   2173 tccttttta tttactttgg tatattttta cactaaggac atttcaaatt aagtactaag   2233
gcacaaagac atgtcatgca tcacagaaaa gcaactactt atatttcaga gcaaattagc   2293
agattaaata gtggtcttaa aactccatat gttaatgatt agatggttat attacaatca   2353
ttttatattt ttttcatga ttaacattca cttatggatt catgatggct gtataaagtg   2413
aatttgaaat ttcaatggtt tactgtcatt gtgtttaaat ctcaacgttc cattatttta  2473
atacttgcaa aaacattact aagtatacca aataattga ctctattatc tgaaatgaag   2533
aataaactga tgctatctca acaataactg ttactttat tttataattt gataatgaat   2593
atatttctgc atttatttac ttctgttttg taaattggga ttttgttaat caaatttatt   2653
gtactatgac taaatgaaat tatttcttac atctaatttg tagaaacagt ataagttata   2713
ttaaagtgtt ttcacatttt tttgaaagac                                    2743

<210> SEQ ID NO 14
<211> LENGTH: 375
<212> TYPE: PRT
<213> ORGANISM: Homo sapiens

<400> SEQUENCE: 14

Met Gln Lys Leu Gln Leu Cys Val Tyr Ile Tyr Leu Phe Met Leu Ile
 1               5                   10                  15

Val Ala Gly Pro Val Asp Leu Asn Glu Asn Ser Glu Gln Lys Glu Asn
```

```
            20                  25                  30
Val Glu Lys Glu Gly Leu Cys Asn Ala Cys Thr Trp Arg Gln Asn Thr
             35                  40                  45
Lys Ser Ser Arg Ile Glu Ala Ile Lys Ile Gln Ile Leu Ser Lys Leu
 50                  55                  60
Arg Leu Glu Thr Ala Pro Asn Ile Ser Lys Asp Val Ile Arg Gln Leu
 65                  70                  75                  80
Leu Pro Lys Ala Pro Pro Leu Arg Glu Leu Ile Asp Gln Tyr Asp Val
                 85                  90                  95
Gln Arg Asp Asp Ser Ser Asp Gly Ser Leu Glu Asp Asp Asp Tyr His
                100                 105                 110
Ala Thr Thr Glu Thr Ile Ile Thr Met Pro Thr Glu Ser Asp Phe Leu
             115                 120                 125
Met Gln Val Asp Gly Lys Pro Lys Cys Cys Phe Phe Lys Phe Ser Ser
         130                 135                 140
Lys Ile Gln Tyr Asn Lys Val Val Lys Ala Gln Leu Trp Ile Tyr Leu
145                 150                 155                 160
Arg Pro Val Glu Thr Pro Thr Thr Val Phe Val Gln Ile Leu Arg Leu
                165                 170                 175
Ile Lys Pro Met Lys Asp Gly Thr Arg Tyr Thr Gly Ile Arg Ser Leu
             180                 185                 190
Lys Leu Asp Met Asn Pro Gly Thr Gly Ile Trp Gln Ser Ile Asp Val
         195                 200                 205
Lys Thr Val Leu Gln Asn Trp Leu Lys Gln Pro Glu Ser Asn Leu Gly
     210                 215                 220
Ile Glu Ile Lys Ala Leu Asp Glu Asn Gly His Asp Leu Ala Val Thr
225                 230                 235                 240
Phe Pro Gly Pro Gly Glu Asp Gly Leu Asn Pro Phe Leu Glu Val Lys
                245                 250                 255
Val Thr Asp Thr Pro Lys Arg Ser Arg Arg Asp Phe Gly Leu Asp Cys
             260                 265                 270
Asp Glu His Ser Thr Glu Ser Arg Cys Cys Arg Tyr Pro Leu Thr Val
         275                 280                 285
Asp Phe Glu Ala Phe Gly Trp Asp Trp Ile Ile Ala Pro Lys Arg Tyr
     290                 295                 300
Lys Ala Asn Tyr Cys Ser Gly Glu Cys Glu Phe Val Phe Leu Gln Lys
305                 310                 315                 320
Tyr Pro His Thr His Leu Val His Gln Ala Asn Pro Arg Gly Ser Ala
                325                 330                 335
Gly Pro Cys Cys Thr Pro Thr Lys Met Ser Pro Ile Asn Met Leu Tyr
             340                 345                 350
Phe Asn Gly Lys Glu Gln Ile Ile Tyr Gly Lys Ile Pro Ala Met Val
         355                 360                 365
Val Asp Arg Cys Gly Cys Ser
     370                 375

<210> SEQ ID NO 15
<211> LENGTH: 34
<212> TYPE: DNA
<213> ORGANISM: Artificial Sequence
<220> FEATURE:
<223> OTHER INFORMATION: oligonucleotide for PCR

<400> SEQUENCE: 15
cgcggatccg tggatctaaa tgagaacagt gagc                           34
```

<210> SEQ ID NO 16
<211> LENGTH: 37
<212> TYPE: DNA
<213> ORGANISM: Artificial Sequence
<220> FEATURE:
<223> OTHER INFORMATION: oligonucleotide for PCR

<400> SEQUENCE: 16
cgcgaattct caggtaatga ttgtttccgt tgtagcg         37

<210> SEQ ID NO 17
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 17
acactaaatc ttcaagaata         20

<210> SEQ ID NO 18
<211> LENGTH: 1128
<212> TYPE: DNA
<213> ORGANISM: Baboon
<220> FEATURE:
<221> NAME/KEY: CDS
<222> LOCATION: (1)...(1125)

<400> SEQUENCE: 18

| | | | | | | | | | | | | | | | | |
|---|---|---|---|---|---|---|---|---|---|---|---|---|---|---|---|---|---|
| atg | caa | aaa | ctg | caa | ctc | tgt | gtt | tat | att | tac | ctg | ttt | atg | ctg | att | | 48 |
| Met | Gln | Lys | Leu | Gln | Leu | Cys | Val | Tyr | Ile | Tyr | Leu | Phe | Met | Leu | Ile | | |
| 1 | | | | 5 | | | | | 10 | | | | | 15 | | | |
| gtt | gct | ggt | cca | gtg | gat | cta | aat | gag | aac | agt | gag | caa | aaa | gaa | aat | | 96 |
| Val | Ala | Gly | Pro | Val | Asp | Leu | Asn | Glu | Asn | Ser | Glu | Gln | Lys | Glu | Asn | | |
| | | | 20 | | | | | 25 | | | | | 30 | | | | |
| gtg | gaa | aaa | gag | ggg | ctg | tgt | aat | gca | tgt | act | tgg | aga | caa | aac | act | | 144 |
| Val | Glu | Lys | Glu | Gly | Leu | Cys | Asn | Ala | Cys | Thr | Trp | Arg | Gln | Asn | Thr | | |
| | 35 | | | | | 40 | | | | | 45 | | | | | | |
| aaa | tct | tca | aga | ata | gaa | gcc | att | aaa | ata | caa | atc | ctc | agt | aaa | ctt | | 192 |
| Lys | Ser | Ser | Arg | Ile | Glu | Ala | Ile | Lys | Ile | Gln | Ile | Leu | Ser | Lys | Leu | | |
| | 50 | | | | | 55 | | | | | 60 | | | | | | |
| cgt | ctg | gaa | aca | gct | cct | aac | atc | agc | aaa | gat | gct | ata | aga | caa | ctt | | 240 |
| Arg | Leu | Glu | Thr | Ala | Pro | Asn | Ile | Ser | Lys | Asp | Ala | Ile | Arg | Gln | Leu | | |
| 65 | | | | 70 | | | | | 75 | | | | | 80 | | | |
| tta | ccc | aaa | gcg | cct | cca | ctc | cgg | gaa | ctg | att | gat | cag | tat | gat | gtc | | 288 |
| Leu | Pro | Lys | Ala | Pro | Pro | Leu | Arg | Glu | Leu | Ile | Asp | Gln | Tyr | Asp | Val | | |
| | | | 85 | | | | | 90 | | | | | 95 | | | | |
| cag | agg | gat | gac | agc | agc | gat | ggc | tct | ttg | gaa | gat | gac | gat | tat | cac | | 336 |
| Gln | Arg | Asp | Asp | Ser | Ser | Asp | Gly | Ser | Leu | Glu | Asp | Asp | Asp | Tyr | His | | |
| | | | | 100 | | | | | 105 | | | | | 110 | | | |
| gct | aca | acg | gaa | aca | atc | att | acc | atg | cct | aca | gag | tct | gat | ttt | tta | | 384 |
| Ala | Thr | Thr | Glu | Thr | Ile | Ile | Thr | Met | Pro | Thr | Glu | Ser | Asp | Phe | Leu | | |
| | | 115 | | | | | 120 | | | | | 125 | | | | | |
| atg | caa | gtg | gat | gga | aaa | ccc | aaa | tgt | tgc | ttc | ttt | aaa | ttt | agc | tct | | 432 |
| Met | Gln | Val | Asp | Gly | Lys | Pro | Lys | Cys | Cys | Phe | Phe | Lys | Phe | Ser | Ser | | |
| | 130 | | | | | 135 | | | | | 140 | | | | | | |
| aaa | ata | caa | tac | aat | aaa | gtg | gta | aag | gcc | caa | cta | tgg | ata | tat | ttg | | 480 |
| Lys | Ile | Gln | Tyr | Asn | Lys | Val | Val | Lys | Ala | Gln | Leu | Trp | Ile | Tyr | Leu | | |
| 145 | | | | 150 | | | | | 155 | | | | | 160 | | | |
| aga | ccc | gtc | gag | act | cct | aca | aca | gtg | ttt | gtg | caa | atc | ctg | aga | ctc | | 528 |
| Arg | Pro | Val | Glu | Thr | Pro | Thr | Thr | Val | Phe | Val | Gln | Ile | Leu | Arg | Leu | | |
| | | | | 165 | | | | | 170 | | | | | 175 | | | |

```
atc aaa cct atg aaa gac ggt aca agg tat act gga atc cga tct ctg        576
Ile Lys Pro Met Lys Asp Gly Thr Arg Tyr Thr Gly Ile Arg Ser Leu
        180                 185                 190 aaa ctt gac atg aac cca ggc act ggt att tgg cag agc att gat gtg        624
Lys Leu Asp Met Asn Pro Gly Thr Gly Ile Trp Gln Ser Ile Asp Val
    195                 200                 205 aag aca gtg ttg caa aat tgg ctc aaa caa cct gaa tcc aac tta ggc        672
Lys Thr Val Leu Gln Asn Trp Leu Lys Gln Pro Glu Ser Asn Leu Gly
210                 215                 220 att gaa ata aaa gct tta gat gag aat ggt cat gat ctt gct gta acc        720
Ile Glu Ile Lys Ala Leu Asp Glu Asn Gly His Asp Leu Ala Val Thr
225                 230                 235                 240 ttc cca gga cca gga gaa gat ggg ctg aat ccc ttt tta gag gtc aag        768
Phe Pro Gly Pro Gly Glu Asp Gly Leu Asn Pro Phe Leu Glu Val Lys
            245                 250                 255 gta aca gac aca ccc aaa aga tcc aga agg gat ttt ggt ctt gac tgt        816
Val Thr Asp Thr Pro Lys Arg Ser Arg Arg Asp Phe Gly Leu Asp Cys
        260                 265                 270 gat gag cac tca aca gaa tcg cga tgc tgt cgt tac cct cta act gtg        864
Asp Glu His Ser Thr Glu Ser Arg Cys Cys Arg Tyr Pro Leu Thr Val
    275                 280                 285 gat ttt gaa gct ctt gga tgg gat tgg att atc gct cct aaa aga tat        912
Asp Phe Glu Ala Leu Gly Trp Asp Trp Ile Ile Ala Pro Lys Arg Tyr
290                 295                 300 aag gcc aat tac tgc tct gga gag tgt gaa ttt gta ttt tta caa aaa        960
Lys Ala Asn Tyr Cys Ser Gly Glu Cys Glu Phe Val Phe Leu Gln Lys
305                 310                 315                 320 tat cct cat act cat ctg gta cac caa gca aac ccc aga ggt tca gca       1008
Tyr Pro His Thr His Leu Val His Gln Ala Asn Pro Arg Gly Ser Ala
            325                 330                 335 ggc cct tgc tgt act ccc aca aag atg tct cca att aat atg cta tat       1056
Gly Pro Cys Cys Thr Pro Thr Lys Met Ser Pro Ile Asn Met Leu Tyr
        340                 345                 350 ttt aat ggc aaa gaa caa ata ata tat ggg aaa att cca gcc atg gta       1104
Phe Asn Gly Lys Glu Gln Ile Ile Tyr Gly Lys Ile Pro Ala Met Val
    355                 360                 365 gta gac cgc tgc ggg tgc tca tga                                       1128
Val Asp Arg Cys Gly Cys Ser
370                 375
```

<210> SEQ ID NO 19
<211> LENGTH: 375
<212> TYPE: PRT
<213> ORGANISM: Baboon

<400> SEQUENCE: 19

```
Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Arg Glu Leu Ile Asp Gln Tyr Asp Val
                85                  90                  95
```

-continued

```
Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Lys Ala Gln Leu Trp Ile Tyr Leu
145                 150                 155                 160

Arg Pro Val Glu Thr Pro Thr Val Phe Val Gln Ile Leu Arg Leu
            165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
            245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Leu Gly Trp Asp Trp Ile Ile Ala Pro Lys Arg Tyr
            290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
            325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
            370                 375

<210> SEQ ID NO 20
<211> LENGTH: 1128
<212> TYPE: DNA
<213> ORGANISM: Bovine
<220> FEATURE:
<221> NAME/KEY: CDS
<222> LOCATION: (1)...(1125)

<400> SEQUENCE: 20 atg caa aaa ctg caa atc tct gtt tat att tac cta ttt atg ctg att      48
Met Gln Lys Leu Gln Ile Ser Val Tyr Ile Tyr Leu Phe Met Leu Ile
1               5                   10                  15 gtt gct ggc cca gtg gat ctg aat gag aac agc gag cag aag gaa aat      96
Val Ala Gly Pro Val Asp Leu Asn Glu Asn Ser Glu Gln Lys Glu Asn
                20                  25                  30 gtg gaa aaa gag ggg ctg tgt aat gca tgt ttg tgg agg gaa aac act     144
Val Glu Lys Glu Gly Leu Cys Asn Ala Cys Leu Trp Arg Glu Asn Thr
            35                  40                  45 aca tcg tca aga cta gaa gcc ata aaa atc caa atc ctc agt aaa ctt     192
Thr Ser Ser Arg Leu Glu Ala Ile Lys Ile Gln Ile Leu Ser Lys Leu
```

| | | | | | | | | | | | | | | | |
|---|---|---|---|---|---|---|---|---|---|---|---|---|---|---|---|
| | | 50 | | | | 55 | | | | 60 | | | | | |
| cgc | ctg | gaa | aca | gct | cct | aac | atc | agc | aaa | gat | gct | atc | aga | caa | ctt | 240 |
| Arg | Leu | Glu | Thr | Ala | Pro | Asn | Ile | Ser | Lys | Asp | Ala | Ile | Arg | Gln | Leu |
| 65 | | | | 70 | | | | 75 | | | | 80 | ttg ccc aag gct cct cca ctc ctg gaa ctg att gat cag ttc gat gtc  288
Leu Pro Lys Ala Pro Pro Leu Leu Glu Leu Ile Asp Gln Phe Asp Val
         85                  90                  95 cag aga gat gcc agc agt gac ggc tcc ttg gaa gac gat gac tac cac  336
Gln Arg Asp Ala Ser Ser Asp Gly Ser Leu Glu Asp Asp Asp Tyr His
            100                 105                 110 gcc agg acg gaa acg gtc att acc atg ccc acg gag tct gat ctt cta  384
Ala Arg Thr Glu Thr Val Ile Thr Met Pro Thr Glu Ser Asp Leu Leu
        115                 120                 125 acg caa gtg gaa gga aaa ccc aaa tgt tgc ttc ttt aaa ttt agc tct  432
Thr Gln Val Glu Gly Lys Pro Lys Cys Cys Phe Phe Lys Phe Ser Ser
    130                 135                 140 aag ata caa tac aat aaa cta gta aag gcc caa ctg tgg ata tat ctg  480
Lys Ile Gln Tyr Asn Lys Leu Val Lys Ala Gln Leu Trp Ile Tyr Leu
145                 150                 155                 160 agg cct gtc aag act cct gcg aca gtg ttt gtg caa atc ctg aga ctc  528
Arg Pro Val Lys Thr Pro Ala Thr Val Phe Val Gln Ile Leu Arg Leu
                165                 170                 175 atc aaa ccc atg aaa gac ggt aca agg tat act gga atc cga tct ctg  576
Ile Lys Pro Met Lys Asp Gly Thr Arg Tyr Thr Gly Ile Arg Ser Leu
            180                 185                 190 aaa ctt gac atg aac cca ggc act ggt att tgg cag agc att gat gtg  624
Lys Leu Asp Met Asn Pro Gly Thr Gly Ile Trp Gln Ser Ile Asp Val
        195                 200                 205 aag aca gtg ttg cag aac tgg ctc aaa caa cct gaa tcc aac tta ggc  672
Lys Thr Val Leu Gln Asn Trp Leu Lys Gln Pro Glu Ser Asn Leu Gly
    210                 215                 220 att gaa atc aaa gct tta gat gag aat ggc cat gat ctt gct gta acc  720
Ile Glu Ile Lys Ala Leu Asp Glu Asn Gly His Asp Leu Ala Val Thr
225                 230                 235                 240 ttc cca gaa cca gga gaa gat gga ctg act ccc ttt tta gaa gtc aag  768
Phe Pro Glu Pro Gly Glu Asp Gly Leu Thr Pro Phe Leu Glu Val Lys
                245                 250                 255 gta aca gac aca cca aaa aga tct agg aga gat ttt ggg ctt gat tgt  816
Val Thr Asp Thr Pro Lys Arg Ser Arg Arg Asp Phe Gly Leu Asp Cys
            260                 265                 270 gat gaa cac tcc aca gaa tct cga tgc tgt cgt tac cct cta act gtg  864
Asp Glu His Ser Thr Glu Ser Arg Cys Cys Arg Tyr Pro Leu Thr Val
        275                 280                 285 gat ttt gaa gct ttt gga tgg gat tgg att att gca cct aaa aga tat  912
Asp Phe Glu Ala Phe Gly Trp Asp Trp Ile Ile Ala Pro Lys Arg Tyr
    290                 295                 300 aag gcc aat tac tgc tct gga gaa tgt gaa ttt gta ttt ttg caa aag  960
Lys Ala Asn Tyr Cys Ser Gly Glu Cys Glu Phe Val Phe Leu Gln Lys
305                 310                 315                 320 tat cct cat acc cat ctt gtg cac caa gca aac ccc aga ggt tca gcc  1008
Tyr Pro His Thr His Leu Val His Gln Ala Asn Pro Arg Gly Ser Ala
                325                 330                 335 ggc ccc tgc tgt act cct aca aag atg tct cca att aat atg cta tat  1056
Gly Pro Cys Cys Thr Pro Thr Lys Met Ser Pro Ile Asn Met Leu Tyr
            340                 345                 350 ttt aat ggc gaa gga caa ata ata tac ggg aag att cca gcc atg gta  1104
Phe Asn Gly Glu Gly Gln Ile Ile Tyr Gly Lys Ile Pro Ala Met Val
        355                 360                 365 gta gat cgc tgt ggg tgt tca tga                                   1128

```
Val Asp Arg Cys Gly Cys Ser
    370             375

<210> SEQ ID NO 21
<211> LENGTH: 375
<212> TYPE: PRT
<213> ORGANISM: Bovine

<400> SEQUENCE: 21

Met Gln Lys Leu Gln Ile Ser Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Leu Trp Arg Glu Asn Thr
        35                  40                  45

Thr Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Leu Glu Leu Ile Asp Gln Phe Asp Val
                85                  90                  95

Gln Arg Asp Ala Ser Ser Asp Gly Ser Leu Glu Asp Asp Asp Tyr His
            100                 105                 110

Ala Arg Thr Glu Thr Val Ile Thr Met Pro Thr Glu Ser Asp Leu Leu
        115                 120                 125

Thr Gln Val Glu Gly Lys Pro Lys Cys Cys Phe Phe Lys Phe Ser Ser
    130                 135                 140

Lys Ile Gln Tyr Asn Lys Leu Val Lys Ala Gln Leu Trp Ile Tyr Leu
145                 150                 155                 160

Arg Pro Val Lys Thr Pro Ala Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Asp Gly Leu Thr Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Glu Gly Gln Ile Ile Tyr Gly Lys Ile Pro Ala Met Val
        355                 360                 365
```

```
Val Asp Arg Cys Gly Cys Ser
    370             375
```

```
<210> SEQ ID NO 22
<211> LENGTH: 1128
<212> TYPE: DNA
<213> ORGANISM: Gallus gallus
<220> FEATURE:
<221> NAME/KEY: CDS
<222> LOCATION: (1)...(1125)

<400> SEQUENCE: 22
```

| | | | | | | | | | | | | | | | | |
|---|---|---|---|---|---|---|---|---|---|---|---|---|---|---|---|---|
| atg | caa | aag | ctg | gca | gtc | tat | gtt | tat | att | tac | ctg | ttc | atg | cag | atc | 48 |
| Met | Gln | Lys | Leu | Ala | Val | Tyr | Val | Tyr | Ile | Tyr | Leu | Phe | Met | Gln | Ile | |
| 1 | | | | 5 | | | | | 10 | | | | | 15 | | |
| gcg | gtt | gat | ccg | gtg | gct | ctg | gat | ggc | agt | agt | cag | ccc | aca | gag | aac | 96 |
| Ala | Val | Asp | Pro | Val | Ala | Leu | Asp | Gly | Ser | Ser | Gln | Pro | Thr | Glu | Asn | |
| | | | 20 | | | | | 25 | | | | | 30 | | | |
| gct | gaa | aaa | gac | gga | ctg | tgc | aat | gct | tgt | acg | tgg | aga | cag | aat | aca | 144 |
| Ala | Glu | Lys | Asp | Gly | Leu | Cys | Asn | Ala | Cys | Thr | Trp | Arg | Gln | Asn | Thr | |
| | | 35 | | | | | 40 | | | | | 45 | | | | |
| aaa | tcc | tcc | aga | ata | gaa | gcc | ata | aaa | att | caa | atc | ctc | agc | aaa | ctg | 192 |
| Lys | Ser | Ser | Arg | Ile | Glu | Ala | Ile | Lys | Ile | Gln | Ile | Leu | Ser | Lys | Leu | |
| | 50 | | | | | 55 | | | | | 60 | | | | | |
| cgc | ctg | gaa | caa | gca | cct | aac | att | agc | agg | gac | gtt | att | aag | cag | ctt | 240 |
| Arg | Leu | Glu | Gln | Ala | Pro | Asn | Ile | Ser | Arg | Asp | Val | Ile | Lys | Gln | Leu | |
| 65 | | | | | 70 | | | | | 75 | | | | | 80 | |
| tta | ccc | aaa | gct | cct | cca | ctg | cag | gaa | ctg | att | gat | cag | tat | gat | gtc | 288 |
| Leu | Pro | Lys | Ala | Pro | Pro | Leu | Gln | Glu | Leu | Ile | Asp | Gln | Tyr | Asp | Val | |
| | | | | 85 | | | | | 90 | | | | | 95 | | |
| cag | agg | gac | gac | agt | agc | gat | ggc | tct | ttg | gaa | gac | gat | gac | tat | cat | 336 |
| Gln | Arg | Asp | Asp | Ser | Ser | Asp | Gly | Ser | Leu | Glu | Asp | Asp | Asp | Tyr | His | |
| | | | | 100 | | | | | 105 | | | | | 110 | | |
| gcc | aca | acc | gag | acg | att | atc | aca | atg | cct | acg | gag | tct | gat | ttt | ctt | 384 |
| Ala | Thr | Thr | Glu | Thr | Ile | Ile | Thr | Met | Pro | Thr | Glu | Ser | Asp | Phe | Leu | |
| | | | 115 | | | | | 120 | | | | | 125 | | | |
| gta | caa | atg | gag | gga | aaa | cca | aaa | tgt | tgc | ttc | ttt | aag | ttt | agc | tct | 432 |
| Val | Gln | Met | Glu | Gly | Lys | Pro | Lys | Cys | Cys | Phe | Phe | Lys | Phe | Ser | Ser | |
| | | 130 | | | | | 135 | | | | | 140 | | | | |
| aaa | ata | caa | tat | aac | aaa | gta | gta | aag | gca | caa | tta | tgg | ata | tac | ttg | 480 |
| Lys | Ile | Gln | Tyr | Asn | Lys | Val | Val | Lys | Ala | Gln | Leu | Trp | Ile | Tyr | Leu | |
| 145 | | | | | 150 | | | | | 155 | | | | | 160 | |
| agg | caa | gtc | caa | aaa | cct | aca | acg | gtg | ttt | gtg | cag | atc | ctg | aga | ctc | 528 |
| Arg | Gln | Val | Gln | Lys | Pro | Thr | Thr | Val | Phe | Val | Gln | Ile | Leu | Arg | Leu | |
| | | | | 165 | | | | | 170 | | | | | 175 | | |
| att | aag | ccc | atg | aaa | gac | ggt | aca | aga | tat | act | gga | att | cga | tct | ttg | 576 |
| Ile | Lys | Pro | Met | Lys | Asp | Gly | Thr | Arg | Tyr | Thr | Gly | Ile | Arg | Ser | Leu | |
| | | | | 180 | | | | | 185 | | | | | 190 | | |
| aaa | ctt | gac | atg | aac | cca | ggc | act | ggt | atc | tgg | cag | agt | att | gat | gtg | 624 |
| Lys | Leu | Asp | Met | Asn | Pro | Gly | Thr | Gly | Ile | Trp | Gln | Ser | Ile | Asp | Val | |
| | | | 195 | | | | | 200 | | | | | 205 | | | |
| aag | aca | gtg | ctg | caa | aat | tgg | ctc | aaa | cag | cct | gaa | tcc | aat | tta | ggc | 672 |
| Lys | Thr | Val | Leu | Gln | Asn | Trp | Leu | Lys | Gln | Pro | Glu | Ser | Asn | Leu | Gly | |
| | | 210 | | | | | 215 | | | | | 220 | | | | |
| atc | gaa | ata | aaa | gct | ttt | gat | gag | act | gga | cga | gat | ctt | gct | gtc | aca | 720 |
| Ile | Glu | Ile | Lys | Ala | Phe | Asp | Glu | Thr | Gly | Arg | Asp | Leu | Ala | Val | Thr | |
| 225 | | | | | 230 | | | | | 235 | | | | | 240 | |
| ttc | cca | gga | cca | gga | gaa | gat | gga | ttg | aac | cca | ttt | tta | gag | gtc | aga | 768 |
| Phe | Pro | Gly | Pro | Gly | Glu | Asp | Gly | Leu | Asn | Pro | Phe | Leu | Glu | Val | Arg | |
| | | | | 245 | | | | | 250 | | | | | 255 | | |

```
gtt aca gac aca ccg aaa cgg tcc cgc aga gat ttt ggc ctt gac tgt      816
Val Thr Asp Thr Pro Lys Arg Ser Arg Arg Asp Phe Gly Leu Asp Cys
        260                 265                 270 gat gag cac tca acg gaa tcc cga tgt tgt cgc tac ccg ctg aca gtg      864
Asp Glu His Ser Thr Glu Ser Arg Cys Cys Arg Tyr Pro Leu Thr Val
            275                 280                 285 gat ttc gaa gct ttt gga tgg gac tgg att ata gca cct aaa aga tac      912
Asp Phe Glu Ala Phe Gly Trp Asp Trp Ile Ile Ala Pro Lys Arg Tyr
    290                 295                 300 aaa gcc aat tac tgc tcc gga gaa tgc gaa ttt gtg ttt cta cag aaa      960
Lys Ala Asn Tyr Cys Ser Gly Glu Cys Glu Phe Val Phe Leu Gln Lys
305                 310                 315                 320 tac ccg cac act cac ctg gta cac caa gca aat ccc aga ggc tca gca     1008
Tyr Pro His Thr His Leu Val His Gln Ala Asn Pro Arg Gly Ser Ala
                325                 330                 335 ggc cct tgc tgc aca ccc acc aag atg tcc cct ata aac atg ctg tat     1056
Gly Pro Cys Cys Thr Pro Thr Lys Met Ser Pro Ile Asn Met Leu Tyr
            340                 345                 350 ttc aat gga aaa gaa caa ata ata tat gga aag ata cca gcc atg gtt     1104
Phe Asn Gly Lys Glu Gln Ile Ile Tyr Gly Lys Ile Pro Ala Met Val
    355                 360                 365 gta gat cgt tgc ggg tgc tca tga                                      1128
Val Asp Arg Cys Gly Cys Ser
    370             375
```

<210> SEQ ID NO 23
<211> LENGTH: 375
<212> TYPE: PRT
<213> ORGANISM: Gallus gallus

<400> SEQUENCE: 23

```
Met Gln Lys Leu Ala Val Tyr Val Tyr Ile Tyr Leu Phe Met Gln Ile
 1               5                  10                  15

Ala Val Asp Pro Val Ala Leu Asp Gly Ser Ser Gln Pro Thr Glu Asn
            20                  25                  30

Ala Glu Lys Asp Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Gln Ala Pro Asn Ile Ser Arg Asp Val Ile Lys Gln Leu
65                  70                  75                  80

Leu Pro Lys Ala Pro Pro Leu Gln Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Val Gln Met Glu Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Gln Val Gln Lys Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205
```

```
Lys Thr Val Leu Gln Asn Trp Leu Lys Gln Pro Glu Ser Asn Leu Gly
        210                 215                 220

Ile Glu Ile Lys Ala Phe Asp Glu Thr Gly Arg Asp Leu Ala Val Thr
225                 230                 235                 240

Phe Pro Gly Pro Gly Glu Asp Gly Leu Asn Pro Phe Leu Glu Val Arg
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
            355                 360                 365

Val Asp Arg Cys Gly Cys Ser
        370                 375

<210> SEQ ID NO 24
<211> LENGTH: 1131
<212> TYPE: DNA
<213> ORGANISM: Rattus norvegicus
<220> FEATURE:
<221> NAME/KEY: CDS
<222> LOCATION: (1)...(1128)

<400> SEQUENCE: 24 atg att caa aaa ccg caa atg tat gtt tat att tac ctg ttt gtg ctg      48
Met Ile Gln Lys Pro Gln Met Tyr Val Tyr Ile Tyr Leu Phe Val Leu
1               5                   10                  15 att gct gct ggc cca gtg gat cta aat gag gac agt gag aga gag gcg      96
Ile Ala Ala Gly Pro Val Asp Leu Asn Glu Asp Ser Glu Arg Glu Ala
            20                  25                  30 aat gtg gaa aaa gag ggg ctg tgt aat gcg tgt gcg tgg aga caa aac     144
Asn Val Glu Lys Glu Gly Leu Cys Asn Ala Cys Ala Trp Arg Gln Asn
        35                  40                  45 aca agg tac tcc aga ata gaa gcc ata aaa att caa atc ctc agt aaa     192
Thr Arg Tyr Ser Arg Ile Glu Ala Ile Lys Ile Gln Ile Leu Ser Lys
    50                  55                  60 ctc cgc ctg gaa aca gcg cct aac atc agc aaa gat gct ata aga caa     240
Leu Arg Leu Glu Thr Ala Pro Asn Ile Ser Lys Asp Ala Ile Arg Gln
65                  70                  75                  80 ctt ctg ccc aga gcg cct cca ctc cgg gaa ctg atc gat cag tac gac     288
Leu Leu Pro Arg Ala Pro Pro Leu Arg Glu Leu Ile Asp Gln Tyr Asp
                85                  90                  95 gtc cag agg gat gac agc agt gac ggc tct ttg gaa gat gac gat tat     336
Val Gln Arg Asp Asp Ser Ser Asp Gly Ser Leu Glu Asp Asp Asp Tyr
            100                 105                 110 cac gct acc acg gaa aca atc att acc atg cct acc gag tct gac ttt     384
His Ala Thr Thr Glu Thr Ile Ile Thr Met Pro Thr Glu Ser Asp Phe
        115                 120                 125 cta atg caa gcg gat gga aag ccc aaa tgt tgc ttt ttt aaa ttt agc     432
Leu Met Gln Ala Asp Gly Lys Pro Lys Cys Cys Phe Phe Lys Phe Ser
    130                 135                 140
```

-continued

```
tct aaa ata cag tac aac aaa gtg gta aag gcc cag ctg tgg ata tat      480
Ser Lys Ile Gln Tyr Asn Lys Val Val Lys Ala Gln Leu Trp Ile Tyr
145                 150                 155                 160 ctg aga gcc gtc aag act cct aca aca gtg ttt gtg caa atc ctg aga      528
Leu Arg Ala Val Lys Thr Pro Thr Thr Val Phe Val Gln Ile Leu Arg
                165                 170                 175 ctc atc aaa ccc atg aaa gac ggt aca agg tat acc gga atc cga tct      576
Leu Ile Lys Pro Met Lys Asp Gly Thr Arg Tyr Thr Gly Ile Arg Ser
            180                 185                 190 ctg aaa ctt gac atg agc cca ggc act ggt att tgg cag agt att gat      624
Leu Lys Leu Asp Met Ser Pro Gly Thr Gly Ile Trp Gln Ser Ile Asp
        195                 200                 205 gtg aag aca gtg ttg caa aat tgg ctc aaa cag cct gaa tcc aac tta      672
Val Lys Thr Val Leu Gln Asn Trp Leu Lys Gln Pro Glu Ser Asn Leu
    210                 215                 220 ggc att gaa atc aaa gct ttg gat gag aat ggg cat gat ctt gct gta      720
Gly Ile Glu Ile Lys Ala Leu Asp Glu Asn Gly His Asp Leu Ala Val
225                 230                 235                 240 acc ttc cca gga cca gga gaa gat ggg ctg aat ccc ttt tta gaa gtc      768
Thr Phe Pro Gly Pro Gly Glu Asp Gly Leu Asn Pro Phe Leu Glu Val
                245                 250                 255 aaa gta aca gac aca ccc aag agg tcc cgg aga gac ttt ggg ctt gac      816
Lys Val Thr Asp Thr Pro Lys Arg Ser Arg Arg Asp Phe Gly Leu Asp
            260                 265                 270 tgc gat gaa cac tcc acg gaa tcg cgg tgc tgt cgc tac ccc ctc acg      864
Cys Asp Glu His Ser Thr Glu Ser Arg Cys Cys Arg Tyr Pro Leu Thr
        275                 280                 285 gtc gat ttc gaa gcc ttt gga tgg gac tgg att att gca ccc aaa aga      912
Val Asp Phe Glu Ala Phe Gly Trp Asp Trp Ile Ile Ala Pro Lys Arg
    290                 295                 300 tat aag gct aat tac tgc tct gga gag tgt gaa ttt gtg ttc tta caa      960
Tyr Lys Ala Asn Tyr Cys Ser Gly Glu Cys Glu Phe Val Phe Leu Gln
305                 310                 315                 320 aaa tat ccg cat act cat ctt gtg cac caa gca aac ccc aga ggc tcg     1008
Lys Tyr Pro His Thr His Leu Val His Gln Ala Asn Pro Arg Gly Ser
                325                 330                 335 gca ggc cct tgc tgc acg cca aca aaa atg tct ccc att aat atg cta     1056
Ala Gly Pro Cys Cys Thr Pro Thr Lys Met Ser Pro Ile Asn Met Leu
            340                 345                 350 tat ttt aat ggc aaa gaa caa ata ata tat ggg aaa att cca gcc atg     1104
Tyr Phe Asn Gly Lys Glu Gln Ile Ile Tyr Gly Lys Ile Pro Ala Met
        355                 360                 365 gta gta gac cgg tgt ggg tgc tcg tga                                 1131
Val Val Asp Arg Cys Gly Cys Ser
    370                 375
```

<210> SEQ ID NO 25
<211> LENGTH: 376
<212> TYPE: PRT
<213> ORGANISM: Rattus norvegicus

<400> SEQUENCE: 25

```
Met Ile Gln Lys Pro Gln Met Tyr Val Tyr Ile Tyr Leu Phe Val Leu
 1               5                  10                  15

Ile Ala Ala Gly Pro Val Asp Leu Asn Glu Asp Ser Glu Arg Glu Ala
            20                  25                  30

Asn Val Glu Lys Glu Gly Leu Cys Asn Ala Cys Ala Trp Arg Gln Asn
        35                  40                  45

Thr Arg Tyr Ser Arg Ile Glu Ala Ile Lys Ile Gln Ile Leu Ser Lys
```

```
              50                  55                  60
Leu Arg Leu Glu Thr Ala Pro Asn Ile Ser Lys Asp Ala Ile Arg Gln
 65                  70                  75                  80

Leu Leu Pro Arg Ala Pro Pro Leu Arg Glu Leu Ile Asp Gln Tyr Asp
                 85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
130                 135                 140

Ser Lys Ile Gln Tyr Asn Lys Val Val Lys Ala Gln Leu Trp Ile Tyr
145                 150                 155                 160

Leu Arg Ala Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
                180                 185                 190

Leu Lys Leu Asp Met Ser Pro Gly Thr Gly Ile Trp Gln Ser Ile Asp
            195                 200                 205

Val Lys Thr Val Leu Gln Asn Trp Leu Lys Gln Pro Glu Ser Asn Leu
        210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
                260                 265                 270

Cys Asp Glu His Ser Thr Glu Ser Arg Cys Cys Arg Tyr Pro Leu Thr
            275                 280                 285

Val Asp Phe Glu Ala Phe Gly Trp Asp Trp Ile Ile Ala Pro Lys Arg
        290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
                340                 345                 350

Tyr Phe Asn Gly Lys Glu Gln Ile Ile Tyr Gly Lys Ile Pro Ala Met
            355                 360                 365

Val Val Asp Arg Cys Gly Cys Ser
        370                 375

<210> SEQ ID NO 26
<211> LENGTH: 1128
<212> TYPE: DNA
<213> ORGANISM: Meleagris gallopavo
<220> FEATURE:
<221> NAME/KEY: CDS
<222> LOCATION: (1)...(1125)

<400> SEQUENCE: 26 atg caa aag cta gca gtc tat gtt tat att tac ctg ttc atg cag att       48
Met Gln Lys Leu Ala Val Tyr Val Tyr Ile Tyr Leu Phe Met Gln Ile
 1               5                  10                  15 tta gtt cat ccg gtg gct ctt gat ggc agt agt cag ccc aca gag aac       96
Leu Val His Pro Val Ala Leu Asp Gly Ser Ser Gln Pro Thr Glu Asn
```

| | |
|---|---|
| gct gaa aaa gac gga ctg tgc aat gct tgc acg tgg aga cag aat act<br>Ala Glu Lys Asp Gly Leu Cys Asn Ala Cys Thr Trp Arg Gln Asn Thr<br>35                    40                    45 | 144 |
| aaa tcc tcc aga ata gaa gcc ata aaa att caa atc ctc agc aaa ctg<br>Lys Ser Ser Arg Ile Glu Ala Ile Lys Ile Gln Ile Leu Ser Lys Leu<br>50                    55                    60 | 192 |
| cgc ctg gaa caa gca cct aac att agc agg gac gtt att aaa caa ctt<br>Arg Leu Glu Gln Ala Pro Asn Ile Ser Arg Asp Val Ile Lys Gln Leu<br>65                    70                    75                    80 | 240 |
| tta ccc aaa gct cct ccg ctg cag gaa ctg att gat cag tat gac gtc<br>Leu Pro Lys Ala Pro Pro Leu Gln Glu Leu Ile Asp Gln Tyr Asp Val<br>                    85                    90                    95 | 288 |
| cag aga gac gac agt agc gat ggc tct ttg gaa gac gat gac tat cat<br>Gln Arg Asp Asp Ser Ser Asp Gly Ser Leu Glu Asp Asp Asp Tyr His<br>                        100                  105                110 | 336 |
| gcc aca acc gaa acg att atc aca atg cct acg gag tct gat ttt ctt<br>Ala Thr Thr Glu Thr Ile Ile Thr Met Pro Thr Glu Ser Asp Phe Leu<br>115                   120                 125 | 384 |
| gta caa atg gag gga aaa cca aaa tgt tgc ttc ttt aag ttt agc tct<br>Val Gln Met Glu Gly Lys Pro Lys Cys Cys Phe Phe Lys Phe Ser Ser<br>130                   135                 140 | 432 |
| aaa ata caa tat aac aaa gta gta aag gca caa tta tgg ata tac ttg<br>Lys Ile Gln Tyr Asn Lys Val Val Lys Ala Gln Leu Trp Ile Tyr Leu<br>145                   150                 155                160 | 480 |
| agg caa gtc caa aaa cct aca acg gtg ttt gtg cag atc ctg aga ctc<br>Arg Gln Val Gln Lys Pro Thr Thr Val Phe Val Gln Ile Leu Arg Leu<br>                        165                  170                175 | 528 |
| att aaa ccc atg aaa gac ggt aca aga tat act gga att cga tct ttg<br>Ile Lys Pro Met Lys Asp Gly Thr Arg Tyr Thr Gly Ile Arg Ser Leu<br>                  180                  185                190 | 576 |
| aaa ctt gac atg aac cca ggc act ggt atc tgg cag agt att gat gtg<br>Lys Leu Asp Met Asn Pro Gly Thr Gly Ile Trp Gln Ser Ile Asp Val<br>                  195                  200                205 | 624 |
| aag aca gtg ttg caa aat tgg ctc aaa cag cct gaa tcc aat tta ggc<br>Lys Thr Val Leu Gln Asn Trp Leu Lys Gln Pro Glu Ser Asn Leu Gly<br>            210                  215                220 | 672 |
| atc gaa ata aaa gct ttt gat gag aat gga cga gat ctt gct gta aca<br>Ile Glu Ile Lys Ala Phe Asp Glu Asn Gly Arg Asp Leu Ala Val Thr<br>225                   230                 235                240 | 720 |
| ttc cca gga cca ggt gaa gat gga ctg aac cca ttt tta gag gtc aga<br>Phe Pro Gly Pro Gly Glu Asp Gly Leu Asn Pro Phe Leu Glu Val Arg<br>                  245                  250                255 | 768 |
| gtt aca gac aca cca aaa cgg tcc cgc aga gat ttt ggc ctt gac tgc<br>Val Thr Asp Thr Pro Lys Arg Ser Arg Arg Asp Phe Gly Leu Asp Cys<br>            260                  265                270 | 816 |
| gac gag cac tca acg gaa tct cga tgt tgt cgc tac ccg ctg aca gtg<br>Asp Glu His Ser Thr Glu Ser Arg Cys Cys Arg Tyr Pro Leu Thr Val<br>            275                  280                285 | 864 |
| gat ttt gaa gct ttt gga tgg gac tgg att ata gca cct aaa aga tac<br>Asp Phe Glu Ala Phe Gly Trp Asp Trp Ile Ile Ala Pro Lys Arg Tyr<br>290                   295                 300 | 912 |
| aaa gcc aat tac tgc tct gga gaa tgt gaa ttc gta ttt cta cag aaa<br>Lys Ala Asn Tyr Cys Ser Gly Glu Cys Glu Phe Val Phe Leu Gln Lys<br>305                   310                 315                320 | 960 |
| tac ccg cac act cac ctg gta cac caa gca aat cca aga ggc tca gca<br>Tyr Pro His Thr His Leu Val His Gln Ala Asn Pro Arg Gly Ser Ala<br>                  325                  330                335 | 1008 |
| ggc cct tgc tgc aca ccc acc aag atg tcc cct ata aac atg ctg tat | 1056 |

```
Gly Pro Cys Cys Thr Pro Thr Lys Met Ser Pro Ile Asn Met Leu Tyr
            340                 345                 350 ttc aat gga aaa gaa caa ata ata tat gga aag ata cca gcc atg gtt      1104
Phe Asn Gly Lys Glu Gln Ile Ile Tyr Gly Lys Ile Pro Ala Met Val
            355                 360                 365 gta gat cgt tgc ggg tgc tca tga                                      1128
Val Asp Arg Cys Gly Cys Ser
    370                 375
```

<210> SEQ ID NO 27
<211> LENGTH: 375
<212> TYPE: PRT
<213> ORGANISM: Meleagris gallopavo

<400> SEQUENCE: 27

```
Met Gln Lys Leu Ala Val Tyr Val Tyr Ile Tyr Leu Phe Met Gln Ile
 1               5                  10                  15

Leu Val His Pro Val Ala Leu Asp Gly Ser Ser Gln Pro Thr Glu Asn
                20                  25                  30

Ala Glu Lys Asp Gly Leu Cys Asn Ala Cys Thr Trp Arg Gln Asn Thr
            35                  40                  45

Lys Ser Ser Arg Ile Glu Ala Ile Lys Ile Gln Ile Leu Ser Lys Leu
    50                  55                  60

Arg Leu Glu Gln Ala Pro Asn Ile Ser Arg Asp Val Ile Lys Gln Leu
65                  70                  75                  80

Leu Pro Lys Ala Pro Pro Leu Gln Glu Leu Ile Asp Gln Tyr Asp Val
                85                  90                  95

Gln Arg Asp Asp Ser Ser Asp Gly Ser Leu Glu Asp Asp Tyr His
                100                 105                 110

Ala Thr Thr Glu Thr Ile Ile Thr Met Pro Thr Glu Ser Asp Phe Leu
            115                 120                 125

Val Gln Met Glu Gly Lys Pro Lys Cys Cys Phe Phe Lys Phe Ser Ser
    130                 135                 140

Lys Ile Gln Tyr Asn Lys Val Lys Ala Gln Leu Trp Ile Tyr Leu
145                 150                 155                 160

Arg Gln Val Gln Lys Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
    195                 200                 205

Lys Thr Val Leu Gln Asn Trp Leu Lys Gln Pro Glu Ser Asn Leu Gly
210                 215                 220

Ile Glu Ile Lys Ala Phe Asp Glu Asn Gly Arg Asp Leu Ala Val Thr
225                 230                 235                 240

Phe Pro Gly Pro Gly Glu Asp Gly Leu Asn Pro Phe Leu Glu Val Arg
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
    275                 280                 285

Asp Phe Glu Ala Phe Gly Trp Asp Trp Ile Ile Ala Pro Lys Arg Tyr
290                 295                 300

Lys Ala Asn Tyr Cys Ser Gly Cys Glu Phe Val Phe Leu Gln Lys
305                 310                 315                 320
```

```
Tyr Pro His Thr His Leu Val His Gln Ala Asn Pro Arg Gly Ser Ala
            325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
            370             375

<210> SEQ ID NO 28
<211> LENGTH: 1128
<212> TYPE: DNA
<213> ORGANISM: Porcine
<220> FEATURE:
<221> NAME/KEY: CDS
<222> LOCATION: (1)...(1125)

<400> SEQUENCE: 28 atg caa aaa ctg caa atc tat gtt tat att tac ctg ttt atg ctg att     48
Met Gln Lys Leu Gln Ile Tyr Val Tyr Ile Tyr Leu Phe Met Leu Ile
 1               5                  10                  15 gtt gct ggt ccc gtg gat ctg aat gag aac agc gag caa aag gaa aat     96
Val Ala Gly Pro Val Asp Leu Asn Glu Asn Ser Glu Gln Lys Glu Asn
             20                  25                  30 gtg gaa aaa gag ggg ctg tgt aat gca tgt atg tgg aga caa aac act    144
Val Glu Lys Glu Gly Leu Cys Asn Ala Cys Met Trp Arg Gln Asn Thr
         35                  40                  45 aaa tct tca aga cta gaa gcc ata aaa att caa atc ctc agt aaa ctt    192
Lys Ser Ser Arg Leu Glu Ala Ile Lys Ile Gln Ile Leu Ser Lys Leu
     50                  55                  60 cgc ctg gaa aca gct cct aac att agc aaa gat gct ata aga caa ctt    240
Arg Leu Glu Thr Ala Pro Asn Ile Ser Lys Asp Ala Ile Arg Gln Leu
 65                  70                  75                  80 ttg ccc aaa gct cct cca ctc cgg gaa ctg att gat cag tac gat gtc    288
Leu Pro Lys Ala Pro Pro Leu Arg Glu Leu Ile Asp Gln Tyr Asp Val
                 85                  90                  95 cag aga gat gac agc agt gat ggc tcc ttg gaa gat gat gat tat cac    336
Gln Arg Asp Asp Ser Ser Asp Gly Ser Leu Glu Asp Asp Asp Tyr His
            100                 105                 110 gct acg acg gaa acg atc att acc atg cct aca gag tct gat ctt cta    384
Ala Thr Thr Glu Thr Ile Ile Thr Met Pro Thr Glu Ser Asp Leu Leu
        115                 120                 125 atg caa gtg gaa gga aaa ccc aaa tgc tgc ttc ttt aaa ttt agc tct    432
Met Gln Val Glu Gly Lys Pro Lys Cys Cys Phe Phe Lys Phe Ser Ser
    130                 135                 140 aaa ata caa tac aat aaa gta gta aag gcc caa ctg tgg ata tat ctg    480
Lys Ile Gln Tyr Asn Lys Val Val Lys Ala Gln Leu Trp Ile Tyr Leu
145                 150                 155                 160 aga ccc gtc aag act cct aca aca gtg ttt gtg caa atc ctg aga ctc    528
Arg Pro Val Lys Thr Pro Thr Thr Val Phe Val Gln Ile Leu Arg Leu
                165                 170                 175 atc aaa ccc atg aaa gac ggt aca agg tat act gga atc cga tct ctg    576
Ile Lys Pro Met Lys Asp Gly Thr Arg Tyr Thr Gly Ile Arg Ser Leu
            180                 185                 190 aaa ctt gac atg aac cca ggc act ggt att tgg cag agc att gat gtg    624
Lys Leu Asp Met Asn Pro Gly Thr Gly Ile Trp Gln Ser Ile Asp Val
        195                 200                 205 aag aca gtg ttg caa aat tgg ctc aaa caa cct gaa tcc aac tta ggc    672
Lys Thr Val Leu Gln Asn Trp Leu Lys Gln Pro Glu Ser Asn Leu Gly
    210                 215                 220
```

```
                                                         -continued att gaa atc aaa gct tta gat gag aat ggt cat gat ctt gct gta acc      720
Ile Glu Ile Lys Ala Leu Asp Glu Asn Gly His Asp Leu Ala Val Thr
225             230                 235                 240 ttc cca gga cca gga gaa gat ggg ctg aat ccc ttt tta gaa gtc aag      768
Phe Pro Gly Pro Gly Glu Asp Gly Leu Asn Pro Phe Leu Glu Val Lys
        245                 250                 255 gta aca gac aca cca aaa aga tcc agg aga gat ttt gga ctc gac tgt      816
Val Thr Asp Thr Pro Lys Arg Ser Arg Arg Asp Phe Gly Leu Asp Cys
    260                 265                 270 gat gag cac tca aca gaa tct cga tgc tgt cgt tac cct cta act gtg      864
Asp Glu His Ser Thr Glu Ser Arg Cys Cys Arg Tyr Pro Leu Thr Val
275                 280                 285 gat ttt gaa gct ttt gga tgg gac tgg att att gca ccc aaa aga tat      912
Asp Phe Glu Ala Phe Gly Trp Asp Trp Ile Ile Ala Pro Lys Arg Tyr
    290                 295                 300 aag gcc aat tac tgc tct gga gag tgt gaa ttt gta ttt tta caa aaa      960
Lys Ala Asn Tyr Cys Ser Gly Glu Cys Glu Phe Val Phe Leu Gln Lys
305                 310                 315                 320 tac cct cac act cat ctt gtg cac caa gca aac ccc aga ggt tca gca     1008
Tyr Pro His Thr His Leu Val His Gln Ala Asn Pro Arg Gly Ser Ala
                325                 330                 335 ggc ccc tgc tgt act ccc aca aag atg tct cca atc aat atg cta tat     1056
Gly Pro Cys Cys Thr Pro Thr Lys Met Ser Pro Ile Asn Met Leu Tyr
            340                 345                 350 ttt aat ggc aaa gaa caa ata ata tat ggg aaa att cca gcc atg gta     1104
Phe Asn Gly Lys Glu Gln Ile Ile Tyr Gly Lys Ile Pro Ala Met Val
        355                 360                 365 gta gat cgc tgt ggg tgc tca tga                                     1128
Val Asp Arg Cys Gly Cys Ser
    370                 375

<210> SEQ ID NO 29
<211> LENGTH: 375
<212> TYPE: PRT
<213> ORGANISM: Porcine

<400> SEQUENCE: 29

Met Gln Lys Leu Gln Ile Tyr Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Met Trp Arg Gln Asn Thr
        35                  40                  45

Lys Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Leu Leu
        115                 120                 125

Met Gln Val Glu Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Lys Thr Pro Thr Thr Val Phe Val Gln Ile Leu Arg Leu
```

-continued

```
                165                 170                 175
Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
            210                 215                 220

Ile Glu Ile Lys Ala Leu Asp Glu Asn Gly His Asp Leu Ala Val Thr
225                 230                 235                 240

Phe Pro Gly Pro Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
                355                 360                 365

Val Asp Arg Cys Gly Cys Ser
370                 375

<210> SEQ ID NO 30
<211> LENGTH: 1128
<212> TYPE: DNA
<213> ORGANISM: Ovine
<220> FEATURE:
<221> NAME/KEY: CDS
<222> LOCATION: (1)...(1125)

<400> SEQUENCE: 30 atg caa aaa ctg caa atc ttt gtt tat att tac cta ttt atg ctg ctt      48
Met Gln Lys Leu Gln Ile Phe Val Tyr Ile Tyr Leu Phe Met Leu Leu
  1               5                  10                  15 gtt gct ggc cca gtg gat ctg aat gag aac agc gag cag aag gaa aat      96
Val Ala Gly Pro Val Asp Leu Asn Glu Asn Ser Glu Gln Lys Glu Asn
                 20                  25                  30 gtg gaa aaa aag ggg ctg tgt aat gca tgc ttg tgg aga caa aac aat     144
Val Glu Lys Lys Gly Leu Cys Asn Ala Cys Leu Trp Arg Gln Asn Asn
         35                  40                  45 aaa tcc tca aga cta gaa gcc ata aaa atc caa atc ctc agt aag ctt     192
Lys Ser Ser Arg Leu Glu Ala Ile Lys Ile Gln Ile Leu Ser Lys Leu
     50                  55                  60 cgc ctg gaa aca gct cct aac atc agc aaa gat gct ata aga caa ctt     240
Arg Leu Glu Thr Ala Pro Asn Ile Ser Lys Asp Ala Ile Arg Gln Leu
 65                  70                  75                  80 ttg ccc aag gct cct cca ctc cgg gaa ctg att gat cag tac gat gtc     288
Leu Pro Lys Ala Pro Pro Leu Arg Glu Leu Ile Asp Gln Tyr Asp Val
                 85                  90                  95 cag aga gat gac agc agc gac ggc tcc ttg gaa gac gat gac tac cac     336
Gln Arg Asp Asp Ser Ser Asp Gly Ser Leu Glu Asp Asp Asp Tyr His
                100                 105                 110
```

```
gtt acg acg gaa acg gtc att acc atg ccc acg gag tct gat ctt cta      384
Val Thr Thr Glu Thr Val Ile Thr Met Pro Thr Glu Ser Asp Leu Leu
        115                 120                 125 gca gaa gtg caa gaa aaa ccc aaa tgt tgc ttc ttt aaa ttt agc tct      432
Ala Glu Val Gln Glu Lys Pro Lys Cys Cys Phe Phe Lys Phe Ser Ser
130                 135                 140 aag ata caa cac aat aaa gta gta aag gcc caa ctg tgg ata tat ctg      480
Lys Ile Gln His Asn Lys Val Val Lys Ala Gln Leu Trp Ile Tyr Leu
145                 150                 155                 160 aga cct gtc aag act cct aca aca gtg ttt gtg caa atc ctg aga ctc      528
Arg Pro Val Lys Thr Pro Thr Thr Val Phe Val Gln Ile Leu Arg Leu
                165                 170                 175 atc aaa ccc atg aaa gac ggt aca agg tat act gga atc cga tct ctg      576
Ile Lys Pro Met Lys Asp Gly Thr Arg Tyr Thr Gly Ile Arg Ser Leu
            180                 185                 190 aaa ctt gac atg aac cca ggc act ggt att tgg cag agc att gat gtg      624
Lys Leu Asp Met Asn Pro Gly Thr Gly Ile Trp Gln Ser Ile Asp Val
        195                 200                 205 aag aca gtg ttg caa aac tgg ctc aaa caa cct gaa tcc aac tta ggc      672
Lys Thr Val Leu Gln Asn Trp Leu Lys Gln Pro Glu Ser Asn Leu Gly
210                 215                 220 att gaa atc aaa gct tta gat gag aat ggt cat gat ctt gct gta acc      720
Ile Glu Ile Lys Ala Leu Asp Glu Asn Gly His Asp Leu Ala Val Thr
225                 230                 235                 240 ttc cca gaa cca gga gaa gaa gga ctg aat cct ttt tta gaa gtc aag      768
Phe Pro Glu Pro Gly Glu Glu Gly Leu Asn Pro Phe Leu Glu Val Lys
                245                 250                 255 gta aca gac aca cca aaa aga tct agg aga gat ttt ggg ctt gat tgt      816
Val Thr Asp Thr Pro Lys Arg Ser Arg Arg Asp Phe Gly Leu Asp Cys
            260                 265                 270 gat gag cac tcc aca gaa tct cga tgc tgt cgt tac cct cta act gtg      864
Asp Glu His Ser Thr Glu Ser Arg Cys Cys Arg Tyr Pro Leu Thr Val
        275                 280                 285 gat ttt gaa gct ttt gga tgg gat tgg att att gca cct aaa aga tat      912
Asp Phe Glu Ala Phe Gly Trp Asp Trp Ile Ile Ala Pro Lys Arg Tyr
    290                 295                 300 aag gcc aat tac tgc tct gga gaa tgt gaa ttt tta ttt ttg caa aag      960
Lys Ala Asn Tyr Cys Ser Gly Glu Cys Glu Phe Leu Phe Leu Gln Lys
305                 310                 315                 320 tat cct cat acc cat ctt gtg cac caa gca aac ccc aaa ggt tca gcc     1008
Tyr Pro His Thr His Leu Val His Gln Ala Asn Pro Lys Gly Ser Ala
                325                 330                 335 ggc cct tgc tgt act cct aca aag atg tct cca att aat atg cta tat     1056
Gly Pro Cys Cys Thr Pro Thr Lys Met Ser Pro Ile Asn Met Leu Tyr
            340                 345                 350 ttt aat ggc aaa gaa caa ata ata tat ggg aag att cca ggc atg gta     1104
Phe Asn Gly Lys Glu Gln Ile Ile Tyr Gly Lys Ile Pro Gly Met Val
        355                 360                 365 gta gat cgc tgt ggg tgc tca tga                                     1128
Val Asp Arg Cys Gly Cys Ser
    370                 375

<210> SEQ ID NO 31
<211> LENGTH: 375
<212> TYPE: PRT
<213> ORGANISM: Ovine

<400> SEQUENCE: 31

Met Gln Lys Leu Gln Ile Phe Val Tyr Ile Tyr Leu Phe Met Leu Leu
1               5                   10                  15
```

Val Ala Gly Pro Val Asp Leu Asn Glu Asn Ser Glu Gln Lys Glu Asn
            20                  25                  30

Val Glu Lys Lys Gly Leu Cys Asn Ala Cys Leu Trp Arg Gln Asn Asn
            35                  40                  45

Lys Ser Ser Arg Leu Glu Ala Ile Lys Ile Gln Ile Leu Ser Lys Leu
            50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Val Thr Thr Glu Thr Val Ile Thr Met Pro Thr Glu Ser Asp Leu Leu
            115                 120                 125

Ala Glu Val Gln Glu Lys Pro Lys Cys Cys Phe Phe Lys Phe Ser Ser
            130                 135                 140

Lys Ile Gln His Asn Lys Val Val Lys Ala Gln Leu Trp Ile Tyr Leu
145                 150                 155                 160

Arg Pro Val Lys Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
            210                 215                 220

Ile Glu Ile Lys Ala Leu Asp Glu Asn Gly His Asp Leu Ala Val Thr
225                 230                 235                 240

Phe Pro Glu Pro Gly Glu Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
            290                 295                 300

Lys Ala Asn Tyr Cys Ser Gly Glu Cys Glu Phe Leu Phe Leu Gln Lys
305                 310                 315                 320

Tyr Pro His Thr His Leu Val His Gln Ala Asn Pro Lys Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Gly Met Val
            355                 360                 365

Val Asp Arg Cys Gly Cys Ser
            370                 375

<210> SEQ ID NO 32
<211> LENGTH: 480
<212> TYPE: DNA
<213> ORGANISM: Rattus norvegicus
<220> FEATURE:
<221> NAME/KEY: CDS
<222> LOCATION: (1)...(390)

<400> SEQUENCE: 32

```
gaa gat ggg ctg aat ccc ttt tta gaa gtc aaa gta aca gac aca ccc         48
Glu Asp Gly Leu Asn Pro Phe Leu Glu Val Lys Val Thr Asp Thr Pro
1               5                   10                  15 aag agg tcc cgg aga gac ttt ggg ctt gac tgc gat gaa cac tcc acg         96
Lys Arg Ser Arg Arg Asp Phe Gly Leu Asp Cys Asp Glu His Ser Thr
                20                  25                  30 gaa tcg cgg tgc tgt cgc tac ccc ctc acg gtc gat ttc gaa gcc ttt        144
Glu Ser Arg Cys Cys Arg Tyr Pro Leu Thr Val Asp Phe Glu Ala Phe
            35                  40                  45 gga tgg gac tgg att att gca ccc aaa aga tat aag gct aat tac tgc        192
Gly Trp Asp Trp Ile Ile Ala Pro Lys Arg Tyr Lys Ala Asn Tyr Cys
        50                  55                  60 tct gga gag tgt gaa ttt gtg ttc tta caa aaa tat ccg cat act cat        240
Ser Gly Glu Cys Glu Phe Val Phe Leu Gln Lys Tyr Pro His Thr His
65                  70                  75                  80 ctt gtg cac caa gca aac ccc aga ggc tcg gca ggc cct tgc tgc acg        288
Leu Val His Gln Ala Asn Pro Arg Gly Ser Ala Gly Pro Cys Cys Thr
                85                  90                  95 cca aca aaa atg tct ccc att aat atg cta tat ttt aat ggc aaa gaa        336
Pro Thr Lys Met Ser Pro Ile Asn Met Leu Tyr Phe Asn Gly Lys Glu
                100                 105                 110 caa ata ata tat ggg aaa att cca gcc atg gta gta gac cgg tgt ggg        384
Gln Ile Ile Tyr Gly Lys Ile Pro Ala Met Val Val Asp Arg Cys Gly
            115                 120                 125 tgc tcg tgagctttgc attagcttta aaatttccca atcgtggaa ggtcttcccc         440
Cys Ser
    130 tcgatttcga aactgtgaat ttatgtacca caggctgtag                            480
```

<210> SEQ ID NO 33
<211> LENGTH: 130
<212> TYPE: PRT
<213> ORGANISM: Rattus norvegicus

<400> SEQUENCE: 33

```
Glu Asp Gly Leu Asn Pro Phe Leu Glu Val Lys Val Thr Asp Thr Pro
1               5                   10                  15

Lys Arg Ser Arg Arg Asp Phe Gly Leu Asp Cys Asp Glu His Ser Thr
                20                  25                  30

Glu Ser Arg Cys Cys Arg Tyr Pro Leu Thr Val Asp Phe Glu Ala Phe
            35                  40                  45

Gly Trp Asp Trp Ile Ile Ala Pro Lys Arg Tyr Lys Ala Asn Tyr Cys
        50                  55                  60

Ser Gly Glu Cys Glu Phe Val Phe Leu Gln Lys Tyr Pro His Thr His
65                  70                  75                  80

Leu Val His Gln Ala Asn Pro Arg Gly Ser Ala Gly Pro Cys Cys Thr
                85                  90                  95

Pro Thr Lys Met Ser Pro Ile Asn Met Leu Tyr Phe Asn Gly Lys Glu
                100                 105                 110

Gln Ile Ile Tyr Gly Lys Ile Pro Ala Met Val Val Asp Arg Cys Gly
            115                 120                 125

Cys Ser
    130
```

<210> SEQ ID NO 34
<211> LENGTH: 790
<212> TYPE: DNA

<210> ORGANISM: Gallus gallus
<220> FEATURE:
<221> NAME/KEY: CDS
<222> LOCATION: (1)...(678)

<400> SEQUENCE: 34

```
tta gta gta aag gca caa tta tgg ata tac ttg agg caa gtc caa aaa        48
Leu Val Val Lys Ala Gln Leu Trp Ile Tyr Leu Arg Gln Val Gln Lys
 1               5                  10                  15 cct aca acg gtg ttt gtg cag atc ctg aga ctc att aag ccc atg aaa        96
Pro Thr Thr Val Phe Val Gln Ile Leu Arg Leu Ile Lys Pro Met Lys
             20                  25                  30 gac ggt aca aga tat act gga att cga tct ttg aaa ctt gac atg aac       144
Asp Gly Thr Arg Tyr Thr Gly Ile Arg Ser Leu Lys Leu Asp Met Asn
         35                  40                  45 cca ggc act ggt atc tgg cag agt att gat gtg aag aca gtg ctg caa       192
Pro Gly Thr Gly Ile Trp Gln Ser Ile Asp Val Lys Thr Val Leu Gln
     50                  55                  60 aat tgg ctc aaa cag cct gaa tcc aat tta ggc atc gaa ata aaa gct       240
Asn Trp Leu Lys Gln Pro Glu Ser Asn Leu Gly Ile Glu Ile Lys Ala
 65                  70                  75                  80 ttt gat gag act gga cga gat ctt gct gtc aca ttc cca gga cca gga       288
Phe Asp Glu Thr Gly Arg Asp Leu Ala Val Thr Phe Pro Gly Pro Gly
                 85                  90                  95 gaa gat gga ttg aac cca ttt tta gag gtc aga gtt aca gac aca ccg       336
Glu Asp Gly Leu Asn Pro Phe Leu Glu Val Arg Val Thr Asp Thr Pro
            100                 105                 110 aaa cgg tcc cgc aga gat ttt ggc ctt gac tgt gat gag cac tca acg       384
Lys Arg Ser Arg Arg Asp Phe Gly Leu Asp Cys Asp Glu His Ser Thr
        115                 120                 125 gaa tcc cga tgt tgt cgc tac ccg ctg aca gtg gat ttc gaa gct ttt       432
Glu Ser Arg Cys Cys Arg Tyr Pro Leu Thr Val Asp Phe Glu Ala Phe
    130                 135                 140 gga tgg gac tgg att ata gca cct aaa aga tac aaa gcc aat tac tgc       480
Gly Trp Asp Trp Ile Ile Ala Pro Lys Arg Tyr Lys Ala Asn Tyr Cys
145                 150                 155                 160 tcc gga gaa tgc gaa ttt gtg ttt cta cag aaa tac ccg cac act cac       528
Ser Gly Glu Cys Glu Phe Val Phe Leu Gln Lys Tyr Pro His Thr His
                165                 170                 175 ctg gta cac caa gca aat ccc aga ggc tca gca ggc cct tgc tgc aca       576
Leu Val His Gln Ala Asn Pro Arg Gly Ser Ala Gly Pro Cys Cys Thr
            180                 185                 190 ccc acc aag atg tcc cct ata aac atg ctg tat ttc aat gga aaa gaa       624
Pro Thr Lys Met Ser Pro Ile Asn Met Leu Tyr Phe Asn Gly Lys Glu
        195                 200                 205 caa ata ata tat gga aag ata cca gcc atg gtt gta gat cgt tgc ggg       672
Gln Ile Ile Tyr Gly Lys Ile Pro Ala Met Val Val Asp Arg Cys Gly
    210                 215                 220 tgc tca tgaggctgtc gtgagatcca ccattcgata aattgtggaa gccaccaaaa       728
Cys Ser
225 aaaaagcta tatccctca tccatctttg aaactgtgaa attacgtacg ctaggcattg       788
cc                                                                    790
```

<210> SEQ ID NO 35
<211> LENGTH: 226
<212> TYPE: PRT
<213> ORGANISM: Gallus gallus

<400> SEQUENCE: 35

```
Leu Val Val Lys Ala Gln Leu Trp Ile Tyr Leu Arg Gln Val Gln Lys
  1               5                   10                  15

Pro Thr Thr Val Phe Val Gln Ile Leu Arg Leu Ile Lys Pro Met Lys
             20                  25                  30

Asp Gly Thr Arg Tyr Thr Gly Ile Arg Ser Leu Lys Leu Asp Met Asn
             35                  40                  45

Pro Gly Thr Gly Ile Trp Gln Ser Ile Asp Val Lys Thr Val Leu Gln
 50                  55                  60

Asn Trp Leu Lys Gln Pro Glu Ser Asn Leu Gly Ile Glu Ile Lys Ala
 65                  70                  75                  80

Phe Asp Glu Thr Gly Arg Asp Leu Ala Val Thr Phe Pro Gly Pro Gly
             85                  90                  95

Glu Asp Gly Leu Asn Pro Phe Leu Glu Val Arg Val Thr Asp Thr Pro
            100                 105                 110

Lys Arg Ser Arg Arg Asp Phe Gly Leu Asp Cys Asp Glu His Ser Thr
            115                 120                 125

Glu Ser Arg Cys Cys Arg Tyr Pro Leu Thr Val Asp Phe Glu Ala Phe
130                 135                 140

Gly Trp Asp Trp Ile Ile Ala Pro Lys Arg Tyr Lys Ala Asn Tyr Cys
145                 150                 155                 160

Ser Gly Glu Cys Glu Phe Val Phe Leu Gln Lys Tyr Pro His Thr His
            165                 170                 175

Leu Val His Gln Ala Asn Pro Arg Gly Ser Ala Gly Pro Cys Cys Thr
            180                 185                 190

Pro Thr Lys Met Ser Pro Ile Asn Met Leu Tyr Phe Asn Gly Lys Glu
            195                 200                 205

Gln Ile Ile Tyr Gly Lys Ile Pro Ala Met Val Val Asp Arg Cys Gly
            210                 215                 220

Cys Ser
225

<210> SEQ ID NO 36
<211> LENGTH: 123
<212> TYPE: PRT
<213> ORGANISM: Homo sapiens

<400> SEQUENCE: 36

Arg Pro Arg Arg Asp Ala Glu Pro Val Leu Gly Gly Pro Gly Gly Gly
  1               5                   10                  15

Ala Cys Arg Ala Arg Arg Leu Tyr Val Ser Phe Arg Glu Val Gly Trp
             20                  25                  30

His Arg Trp Val Ile Ala Pro Arg Gly Phe Leu Ala Asn Tyr Cys Gln
             35                  40                  45

Gly Gln Cys Ala Leu Pro Val Ala Leu Ser Gly Ser Gly Gly Pro Pro
 50                  55                  60

Ala Leu Asn His Ala Val Leu Arg Ala Leu Met His Ala Ala Ala Pro
 65                  70                  75                  80

Gly Ala Ala Asp Leu Pro Cys Cys Val Pro Ala Arg Leu Ser Pro Ile
             85                  90                  95

Ser Val Leu Phe Phe Asp Asn Ser Asp Asn Val Val Leu Arg Gln Tyr
            100                 105                 110

Glu Asp Met Val Val Asp Glu Cys Gly Cys Arg
            115                 120

<210> SEQ ID NO 37
```

<211> LENGTH: 118
<212> TYPE: PRT
<213> ORGANISM: Homo sapiens

<400> SEQUENCE: 37

Arg Glu Lys Arg Gln Ala Lys His Lys Gln Arg Lys Arg Leu Lys Ser
1               5                   10                  15

Ser Cys Lys Arg His Pro Leu Tyr Val Asp Phe Ser Asp Val Gly Trp
            20                  25                  30

Asn Asp Trp Ile Val Ala Pro Pro Gly Tyr His Ala Phe Tyr Cys His
                35                  40                  45

Gly Glu Cys Pro Phe Pro Leu Ala Asp His Leu Asn Ser Thr Asn His
        50                  55                  60

Ala Ile Val Gln Thr Leu Val Asn Ser Val Asn Ser Lys Ile Pro Lys
65                  70                  75                  80

Ala Cys Cys Val Pro Thr Glu Leu Ser Ala Ile Ser Met Leu Tyr Leu
                85                  90                  95

Asp Glu Asn Glu Lys Val Val Leu Lys Asn Tyr Gln Asp Met Val Val
                100                 105                 110

Glu Gly Cys Gly Cys Arg
        115

<210> SEQ ID NO 38
<211> LENGTH: 118
<212> TYPE: PRT
<213> ORGANISM: Homo sapiens

<400> SEQUENCE: 38

Lys Arg Ser Pro Lys His His Ser Gln Arg Ala Arg Lys Lys Asn Lys
1               5                   10                  15

Asn Cys Arg Arg His Ser Leu Tyr Val Asp Phe Ser Asp Val Gly Trp
            20                  25                  30

Asn Asp Trp Ile Val Ala Pro Pro Gly Tyr Gln Ala Phe Tyr Cys His
                35                  40                  45

Gly Asp Cys Pro Phe Pro Leu Ala Asp His Leu Asn Ser Thr Asn His
        50                  55                  60

Ala Ile Val Gln Thr Leu Val Asn Ser Val Asn Ser Ser Ile Pro Lys
65                  70                  75                  80

Ala Cys Cys Val Pro Thr Glu Leu Ser Ala Ile Ser Met Leu Tyr Leu
                85                  90                  95

Asp Glu Tyr Asp Lys Val Val Leu Lys Asn Tyr Gln Glu Met Val Val
                100                 105                 110

Glu Gly Cys Gly Cys Arg
        115

<210> SEQ ID NO 39
<211> LENGTH: 119
<212> TYPE: PRT
<213> ORGANISM: Homo sapiens

<400> SEQUENCE: 39

Ser Arg Gly Ser Gly Ser Ser Asp Tyr Asn Gly Ser Glu Leu Lys Thr
1               5                   10                  15

Ala Cys Lys Lys His Glu Leu Tyr Val Ser Phe Gln Asp Leu Gly Trp
            20                  25                  30

Gln Asp Trp Ile Ile Ala Pro Lys Gly Tyr Ala Ala Asn Tyr Cys Asp
                35                  40                  45

```
Gly Glu Cys Ser Phe Pro Leu Asn Ala His Met Asn Ala Thr Asn His
        50                  55                  60

Ala Ile Val Gln Thr Leu Val His Leu Met Asn Pro Glu Tyr Val Pro
 65                  70                  75                  80

Lys Pro Cys Cys Ala Pro Thr Lys Leu Asn Ala Ile Ser Val Leu Tyr
                85                  90                  95

Phe Asp Asp Asn Ser Asn Val Ile Leu Lys Lys Tyr Arg Asn Met Val
               100                 105                 110

Val Arg Ala Cys Gly Cys His
            115

<210> SEQ ID NO 40
<211> LENGTH: 119
<212> TYPE: PRT
<213> ORGANISM: Homo sapiens

<400> SEQUENCE: 40

Leu Arg Met Ala Asn Val Ala Glu Asn Ser Ser Asp Gln Arg Gln
 1               5                  10                  15

Ala Cys Lys Lys His Glu Leu Tyr Val Ser Phe Arg Asp Leu Gly Trp
                20                  25                  30

Gln Asp Trp Ile Ile Ala Pro Glu Gly Tyr Ala Ala Tyr Tyr Cys Glu
            35                  40                  45

Gly Glu Cys Ala Phe Pro Leu Asn Ser Tyr Met Asn Ala Thr Asn His
        50                  55                  60

Ala Ile Val Gln Thr Leu Val His Phe Ile Asn Pro Glu Thr Val Pro
 65                  70                  75                  80

Lys Pro Cys Cys Ala Pro Thr Gln Leu Asn Ala Ile Ser Val Leu Tyr
                85                  90                  95

Phe Asp Asp Ser Ser Asn Val Ile Leu Lys Lys Tyr Arg Asn Met Val
               100                 105                 110

Val Arg Ala Cys Gly Cys His
            115

<210> SEQ ID NO 41
<211> LENGTH: 119
<212> TYPE: PRT
<213> ORGANISM: Homo sapiens

<400> SEQUENCE: 41

Ser Arg Met Ser Ser Val Gly Asp Tyr Asn Thr Ser Glu Gln Lys Gln
 1               5                  10                  15

Ala Cys Lys Lys His Glu Leu Tyr Val Ser Phe Arg Asp Leu Gly Trp
                20                  25                  30

Gln Asp Trp Ile Ile Ala Pro Glu Gly Tyr Ala Ala Phe Tyr Cys Asp
            35                  40                  45

Gly Glu Cys Ser Phe Pro Leu Asn Ala His Met Asn Ala Thr Asn His
        50                  55                  60

Ala Ile Val Gln Thr Leu Val His Leu Met Phe Pro Asp His Val Pro
 65                  70                  75                  80

Lys Pro Cys Cys Ala Pro Thr Lys Leu Asn Ala Ile Ser Val Leu Tyr
                85                  90                  95

Phe Asp Asp Ser Ser Asn Val Ile Leu Lys Lys Tyr Arg Asn Met Val
               100                 105                 110

Val Arg Ser Cys Gly Cys His
            115
```

```
<210> SEQ ID NO 42
<211> LENGTH: 120
<212> TYPE: PRT
<213> ORGANISM: Homo sapiens

<400> SEQUENCE: 42

Glu Gln Thr Leu Lys Lys Ala Arg Arg Lys Gln Trp Ile Glu Pro Arg
  1               5                  10                  15

Asn Cys Ala Arg Arg Tyr Leu Lys Val Asp Phe Ala Asp Ile Gly Trp
                 20                  25                  30

Ser Glu Trp Ile Ile Ser Pro Lys Ser Phe Asp Ala Tyr Tyr Cys Ser
             35                  40                  45

Gly Ala Cys Gln Phe Pro Met Pro Lys Ser Leu Lys Pro Ser Asn His
         50                  55                  60

Ala Thr Ile Gln Ser Ile Val Arg Ala Val Gly Val Val Pro Gly Ile
 65                  70                  75                  80

Pro Glu Pro Cys Cys Val Pro Glu Lys Met Ser Ser Leu Ser Ile Leu
                 85                  90                  95

Phe Phe Asp Glu Asn Lys Asn Val Val Leu Lys Val Tyr Pro Asn Met
            100                 105                 110

Thr Val Glu Ser Cys Ala Cys Arg
            115                 120

<210> SEQ ID NO 43
<211> LENGTH: 116
<212> TYPE: PRT
<213> ORGANISM: Homo sapiens

<400> SEQUENCE: 43

Gly Pro Gly Arg Ala Gln Arg Ser Ala Gly Ala Thr Ala Ala Asp Gly
  1               5                  10                  15

Pro Cys Ala Leu Arg Glu Leu Ser Val Asp Leu Arg Ala Glu Arg Ser
                 20                  25                  30

Val Leu Ile Pro Glu Thr Tyr Gln Ala Asn Asn Cys Gln Gly Val Cys
             35                  40                  45

Gly Trp Pro Gln Ser Asp Arg Asn Pro Arg Tyr Gly Asn His Val Val
         50                  55                  60

Leu Leu Leu Lys Met Gln Ala Arg Gly Ala Ala Leu Ala Arg Pro Pro
 65                  70                  75                  80

Cys Cys Val Pro Thr Ala Tyr Ala Gly Lys Leu Leu Ile Ser Leu Ser
                 85                  90                  95

Glu Glu Arg Ile Ser Ala His His Val Pro Asn Met Val Ala Thr Glu
            100                 105                 110

Cys Gly Cys Arg
            115

<210> SEQ ID NO 44
<211> LENGTH: 122
<212> TYPE: PRT
<213> ORGANISM: Homo sapiens

<400> SEQUENCE: 44

Ala Leu Arg Leu Leu Gln Arg Pro Pro Glu Glu Pro Ala Ala His Ala
  1               5                  10                  15

Asn Cys His Arg Val Ala Leu Asn Ile Ser Phe Gln Glu Leu Gly Trp
                 20                  25                  30

Glu Arg Trp Ile Val Tyr Pro Pro Ser Phe Ile Phe His Tyr Cys His
```

```
                    35                  40                  45
Gly Gly Cys Gly Leu His Ile Pro Pro Asn Leu Ser Leu Pro Val Pro
         50                  55                  60

Gly Ala Pro Pro Thr Pro Ala Gln Pro Tyr Ser Leu Leu Pro Gly Ala
 65                  70                  75                  80

Gln Pro Cys Cys Ala Ala Leu Pro Gly Thr Met Arg Pro Leu His Val
                 85                  90                  95

Arg Thr Thr Ser Asp Gly Gly Tyr Ser Phe Lys Tyr Glu Thr Val Pro
                100                 105                 110

Asn Leu Leu Thr Gln His Cys Ala Cys Ile
                115                 120

<210> SEQ ID NO 45
<211> LENGTH: 122
<212> TYPE: PRT
<213> ORGANISM: Homo sapiens

<400> SEQUENCE: 45

His Arg Arg Arg Arg Gly Leu Glu Cys Asp Gly Lys Val Asn Ile
 1               5                  10                  15

Cys Cys Lys Lys Gln Phe Phe Val Ser Phe Lys Asp Ile Gly Trp Asn
                 20                  25                  30

Asp Trp Ile Ile Ala Pro Ser Gly Tyr His Ala Asn Tyr Cys Glu Gly
             35                  40                  45

Glu Cys Pro Ser His Ile Ala Gly Thr Ser Gly Ser Ser Leu Ser Phe
         50                  55                  60

His Ser Thr Val Ile Asn His Tyr Arg Met Arg Gly His Ser Pro Phe
 65                  70                  75                  80

Ala Asn Leu Lys Ser Cys Val Pro Thr Lys Leu Arg Pro Met Ser
                 85                  90                  95

Met Leu Tyr Tyr Asp Asp Gly Gln Asn Ile Ile Lys Lys Asp Ile Gln
                100                 105                 110

Asn Met Ile Val Glu Glu Cys Gly Cys Ser
            115                 120

<210> SEQ ID NO 46
<211> LENGTH: 121
<212> TYPE: PRT
<213> ORGANISM: Homo sapiens

<400> SEQUENCE: 46

His Arg Ile Arg Lys Arg Gly Leu Glu Cys Asp Gly Arg Thr Asn Leu
 1               5                  10                  15

Cys Cys Arg Gln Gln Phe Phe Ile Asp Phe Arg Leu Ile Gly Trp Asn
                 20                  25                  30

Asp Trp Ile Ile Ala Pro Thr Gly Tyr Tyr Gly Asn Tyr Cys Glu Gly
             35                  40                  45

Ser Cys Pro Ala Tyr Leu Ala Gly Val Pro Gly Ser Ala Ser Ser Phe
         50                  55                  60

His Thr Ala Val Val Asn Gln Tyr Arg Met Arg Gly Leu Asn Pro Gly
 65                  70                  75                  80

Thr Val Asn Ser Cys Cys Ile Pro Thr Lys Leu Ser Thr Met Ser Met
                 85                  90                  95

Leu Tyr Phe Asp Asp Glu Tyr Asn Ile Val Lys Arg Asp Val Pro Asn
                100                 105                 110

Met Ile Val Glu Glu Cys Gly Cys Ala
```

-continued

```
                 115                 120

<210> SEQ ID NO 47
<211> LENGTH: 115
<212> TYPE: PRT
<213> ORGANISM: Homo sapiens

<400> SEQUENCE: 47

His Arg Arg Ala Leu Asp Thr Asn Tyr Cys Phe Ser Ser Thr Glu Lys
  1               5                  10                  15

Asn Cys Cys Val Arg Gln Leu Tyr Ile Asp Phe Arg Lys Asp Leu Gly
             20                  25                  30

Trp Lys Trp Ile His Glu Pro Lys Gly Tyr His Ala Asn Phe Cys Leu
         35                  40                  45

Gly Pro Cys Pro Tyr Ile Trp Ser Leu Asp Thr Gln Tyr Ser Lys Val
     50                  55                  60

Leu Ala Leu Tyr Asn Gln His Asn Pro Gly Ala Ser Ala Ala Pro Cys
 65                  70                  75                  80

Cys Val Pro Gln Ala Leu Glu Pro Leu Pro Ile Val Tyr Tyr Val Gly
                 85                  90                  95

Arg Lys Pro Lys Val Glu Gln Leu Ser Asn Met Ile Val Arg Ser Cys
            100                 105                 110

Lys Cys Ser
        115

<210> SEQ ID NO 48
<211> LENGTH: 115
<212> TYPE: PRT
<213> ORGANISM: Homo sapiens

<400> SEQUENCE: 48

Lys Lys Arg Ala Leu Asp Ala Ala Tyr Cys Phe Arg Asn Val Gln Asp
  1               5                  10                  15

Asn Cys Cys Leu Arg Pro Leu Tyr Ile Asp Phe Lys Arg Asp Leu Gly
             20                  25                  30

Trp Lys Trp Ile His Glu Pro Lys Gly Tyr Asn Ala Asn Phe Cys Ala
         35                  40                  45

Gly Ala Cys Pro Tyr Leu Trp Ser Ser Asp Thr Gln His Ser Arg Val
     50                  55                  60

Leu Ser Leu Tyr Asn Thr Ile Asn Pro Glu Ala Ser Ala Ser Pro Cys
 65                  70                  75                  80

Cys Val Ser Gln Asp Leu Glu Pro Leu Thr Ile Leu Tyr Tyr Ile Gly
                 85                  90                  95

Lys Thr Pro Lys Ile Glu Gln Leu Ser Asn Met Ile Val Lys Ser Cys
            100                 105                 110

Lys Cys Ser
        115

<210> SEQ ID NO 49
<211> LENGTH: 115
<212> TYPE: PRT
<213> ORGANISM: Homo sapiens

<400> SEQUENCE: 49

Lys Lys Arg Ala Leu Asp Thr Asn Tyr Cys Phe Arg Asn Leu Glu Glu
  1               5                  10                  15

Asn Cys Cys Val Arg Pro Leu Tyr Ile Asp Phe Arg Gln Asp Leu Gly
             20                  25                  30
```

```
Trp Lys Trp Val His Glu Pro Lys Gly Tyr Tyr Ala Asn Phe Cys Ser
        35                  40                  45

Gly Pro Cys Pro Tyr Leu Arg Ser Ala Asp Thr Thr His Ser Thr Val
    50                  55                  60

Leu Gly Leu Tyr Asn Thr Leu Asn Pro Glu Ala Ser Ala Ser Pro Cys
65                  70                  75                  80

Cys Val Pro Gln Asp Leu Glu Pro Leu Thr Ile Leu Tyr Tyr Val Gly
                85                  90                  95

Arg Thr Pro Lys Val Glu Gln Leu Ser Asn Met Val Val Lys Ser Cys
                100                 105                 110

Leu Cys Ser
        115

<210> SEQ ID NO 50
<211> LENGTH: 4
<212> TYPE: PRT
<213> ORGANISM: Artificial Sequence
<220> FEATURE:
<223> OTHER INFORMATION: proteolytic cleavage site
<221> NAME/KEY: VARIANT
<222> LOCATION: (0)...(0)
<223> OTHER INFORMATION: Xaa = Any Amino Acid

<400> SEQUENCE: 50

Arg Xaa Xaa Arg
 1

<210> SEQ ID NO 51
<211> LENGTH: 4
<212> TYPE: PRT
<213> ORGANISM: Eukaryotes
<220> FEATURE:
<223> OTHER INFORMATION: proteolytic processing site

<400> SEQUENCE: 51

Arg Ser Arg Arg
 1
```